US011206972B2

(12) United States Patent
Bendory et al.

(10) Patent No.: US 11,206,972 B2
(45) Date of Patent: Dec. 28, 2021

(54) MODULAR BODY CAVITY ACCESS SYSTEM

(71) Applicant: 3NT MEDICAL LTD., Rosh Ha'ayin (IL)

(72) Inventors: Ehud Bendory, Herzliya (IL); Eran Bendory, Maccabin-Re'ut (IL); Gil Hefer, Shimshit (IL)

(73) Assignee: 3NT Medical Ltd., Rosh Ha'ayin (IL)

( * ) Notice: Subject to any disclaimer, the term of this patent is extended or adjusted under 35 U.S.C. 154(b) by 379 days.

(21) Appl. No.: 16/307,094

(22) PCT Filed: Jun. 6, 2017

(86) PCT No.: PCT/IB2017/000756
§ 371 (c)(1),
(2) Date: Dec. 4, 2018

(87) PCT Pub. No.: WO2017/212332
PCT Pub. Date: Dec. 14, 2017

(65) Prior Publication Data
US 2020/0046213 A1    Feb. 13, 2020

Related U.S. Application Data

(60) Provisional application No. 62/345,891, filed on Jun. 6, 2016.

(51) Int. Cl.
*A61B 1/233* (2006.01)
*A61B 1/005* (2006.01)
(Continued)

(52) U.S. Cl.
CPC .......... *A61B 1/233* (2013.01); *A61B 1/00016* (2013.01); *A61B 1/00032* (2013.01);
(Continued)

(58) Field of Classification Search
CPC ..... A61B 1/005; A61B 1/0051; A61B 1/0052; A61B 1/0053; A61B 1/0055;
(Continued)

(56) References Cited

U.S. PATENT DOCUMENTS 5,231,989 A    8/1993    Middleman et al.
5,318,528 A    6/1994    Heaven et al.
(Continued)

FOREIGN PATENT DOCUMENTS

CN    101351236    1/2009
CN    203408026 U    1/2014
(Continued)

OTHER PUBLICATIONS

International Search Report and Written Opinion of the International Searching Authority for International Patent Application No. PCT/IB2017/000756 dated Sep. 20, 2017, 13 pages.
(Continued)

*Primary Examiner* — Ryan N Henderson
(74) *Attorney, Agent, or Firm* — Merchant & Gould P.C.

(57) ABSTRACT

A system for accessing a body cavity, such as a paranasal sinus, may include a sinus access member and a handle. The sinus access member may include a rigid support tube, a curved shape memory member slidably disposed at least partially within the rigid support tube, a flexible tube slidably disposed over at least part of the curved shape memory member, and proximal coupling end. The handle may include an engagement mechanism at a distal end for releasably attaching to the proximal coupling end of the sinus access member, a housing for gripping with a hand, a curving slider for extending and retracting the curved shape memory member, and an extension slider for extending and retracting the flexible tube relative to the curved shape memory member and the rigid support tube. The handle may
(Continued)

be reusable, and the sinus access member may be disposable.

20 Claims, 36 Drawing Sheets

(51) Int. Cl.
| | |
|---|---|
| A61B 1/018 | (2006.01) |
| A61M 25/01 | (2006.01) |
| A61M 25/09 | (2006.01) |
| A61B 1/00 | (2006.01) |
| A61B 1/015 | (2006.01) |
| A61B 1/05 | (2006.01) |
| A61B 1/06 | (2006.01) |
| A61B 1/07 | (2006.01) |
| A61B 17/24 | (2006.01) |
| A61B 5/00 | (2006.01) |

(52) U.S. Cl.
CPC .......... *A61B 1/0056* (2013.01); *A61B 1/0058* (2013.01); *A61B 1/00066* (2013.01); *A61B 1/00078* (2013.01); *A61B 1/00124* (2013.01); *A61B 1/00154* (2013.01); *A61B 1/015* (2013.01); *A61B 1/018* (2013.01); *A61B 1/05* (2013.01); *A61B 1/0669* (2013.01); *A61B 1/0684* (2013.01); *A61B 1/07* (2013.01); *A61B 17/24* (2013.01); *A61B 5/6819* (2013.01); *A61B 2017/246* (2013.01); *A61M 25/0102* (2013.01); *A61M 25/09* (2013.01)

(58) Field of Classification Search
CPC ... A61B 1/0056; A61B 1/0057; A61B 1/0058; A61B 1/0008; A61B 1/00071; A61B 1/00078; A61B 1/00131; A61B 1/00154; A61B 2017/003; A61B 2017/00305; A61B 2017/00309; A61B 2017/00314; A61B 2017/00318; A61B 2017/00323; A61B 2017/00327; A61B 2017/00331; A61B 2017/00336; A61B 17/24; A61B 2017/246; A61M 25/0136; A61M 25/0138; A61M 25/0141; A61M 25/0144; A61M 25/0133; A61M 25/0152; A61M 1/01; A61M 1/0102; A61M 1/0105; A61M 1/09; A61M 2025/09058; A61M 2025/09066; A61M 2025/09075; A61M 2025/09083; A61M 2025/09091; A61M 2025/0175; A61M 2025/0177; A61M 2025/09133; A61M 2025/09141; A61M 2025/0915; A61M 2025/09158
See application file for complete search history.

(56) References Cited

U.S. PATENT DOCUMENTS

| | | | |
|---|---|---|---|
| 5,788,713 | A | 8/1998 | Dubach et al. |
| 6,146,373 | A | 11/2000 | Cragg et al. |
| 6,251,115 | B1 | 6/2001 | Williams et al. |
| 6,589,251 | B2 | 7/2003 | Yee et al. |
| 6,755,812 | B2 | 6/2004 | Peterson et al. |
| 7,625,356 | B2 | 12/2009 | Mickley |
| 7,993,351 | B2 | 8/2011 | Worley et al. |
| 8,715,226 | B2 | 5/2014 | Webster et al. |
| 10,258,225 | B2 | 4/2019 | Bendory |
| 2008/0167527 | A1 | 7/2008 | Slenker et al. |
| 2008/0183128 | A1 | 7/2008 | Morriss et al. |
| 2009/0171271 | A1 | 7/2009 | Webster et al. |
| 2010/0030113 | A1 | 2/2010 | Morriss et al. |
| 2010/0076403 | A1 | 3/2010 | Harris et al. |
| 2011/0257479 | A1 | 11/2011 | Adams et al. |
| 2012/0029334 | A1 | 2/2012 | Tegg |
| 2012/0053567 | A1 | 3/2012 | Schreck et al. |
| 2012/0071857 | A1* | 3/2012 | Goldfarb ......... A61M 25/09041 604/514 |
| 2014/0012075 | A1 | 1/2014 | Konstorum |
| 2014/0358177 | A1 | 12/2014 | Schreck et al. |
| 2014/0371532 | A1 | 12/2014 | Trovato |
| 2015/0141819 | A1 | 5/2015 | Linden et al. |
| 2015/0289754 | A1* | 10/2015 | Bendory .......... A61B 17/00234 600/104 |

FOREIGN PATENT DOCUMENTS

| | | | |
|---|---|---|---|
| CN | 105433896 | B | 2/2017 |
| CN | 108125666 | A | 6/2018 |
| DE | 4223897 | | 1/1994 |
| JP | H06-505188 | | 6/1994 |
| JP | 2001-520085 | | 10/2001 |
| JP | 2005-515830 | | 6/2005 |
| JP | 2007-202727 | | 8/2007 |
| JP | 2009-100929 | | 5/2009 |
| JP | 2011-239989 | | 12/2011 |
| WO | WO 1992014506 | | 9/1992 |
| WO | WO 2003063732 | | 8/2003 |
| WO | WO 2007059233 | | 5/2007 |
| WO | WO 2011064602 | | 6/2011 |
| WO | WO 2011141925 | | 11/2011 |
| WO | WO-2014072977 | A1 * | 5/2014 ............ A61B 17/24 |
| WO | WO 2017212332 | A1 | 12/2017 |
| WO | WO 2018080769 | A1 | 5/2018 |
| WO | WO 2020121138 | A2 | 6/2020 |

OTHER PUBLICATIONS

International Preliminary Report on Patentability for PCT/IB2017/000756, dated December dated Dec. 11, 2018, 9 pages.

* cited by examiner

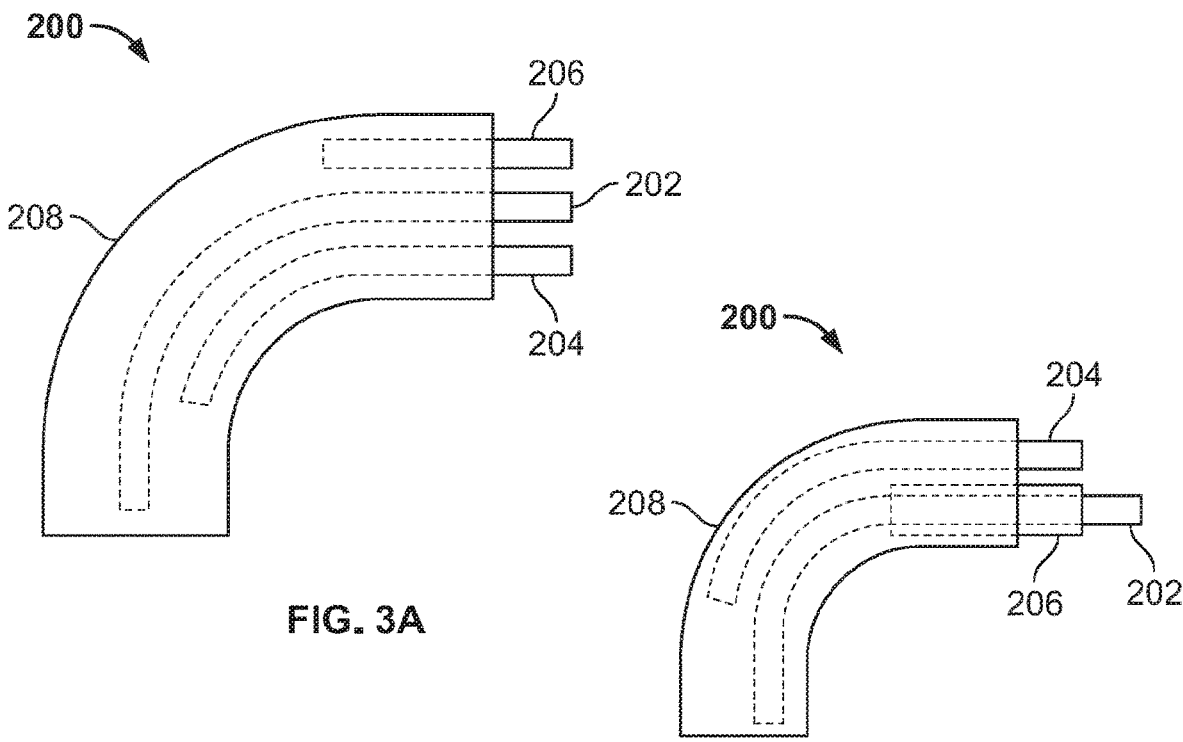
FIG. 3A
FIG. 3B
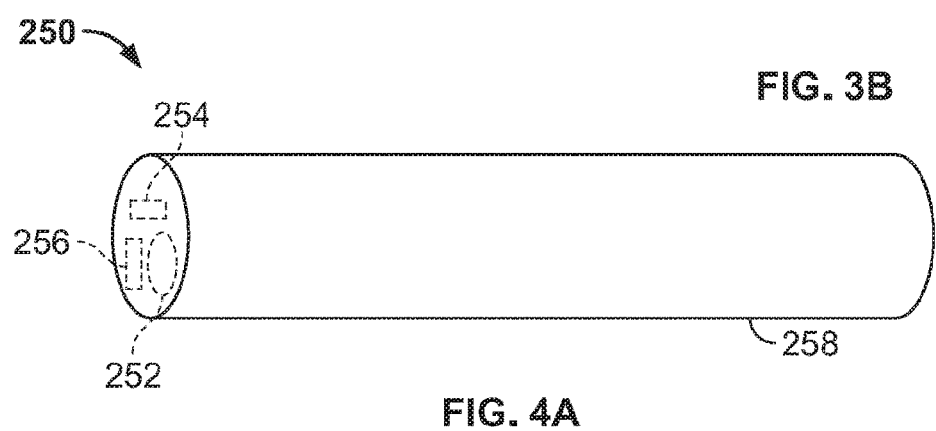
FIG. 4A
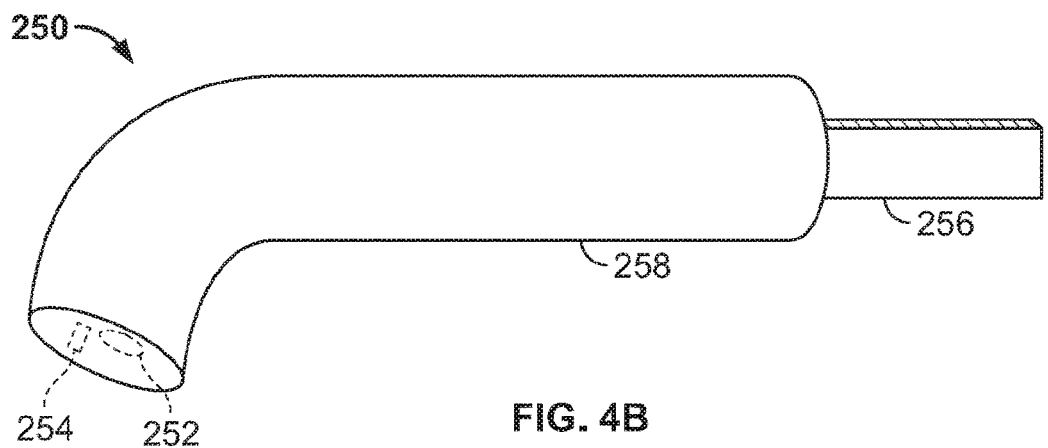
FIG. 4B

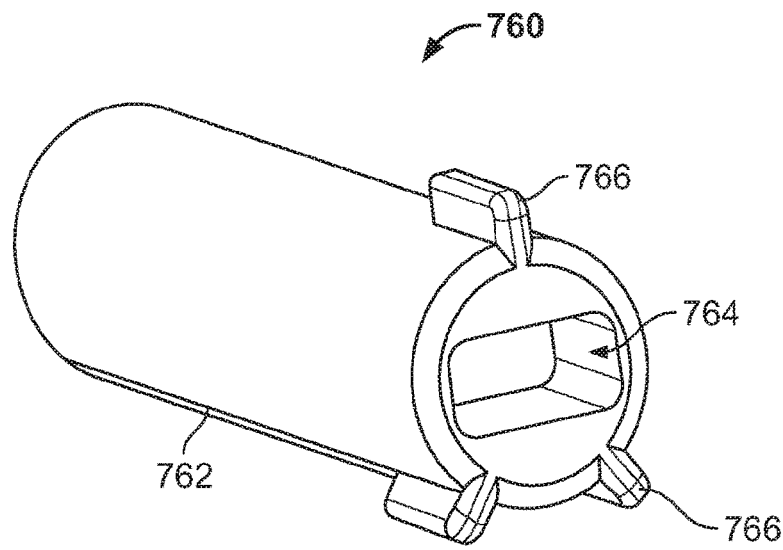
FIG. 18A
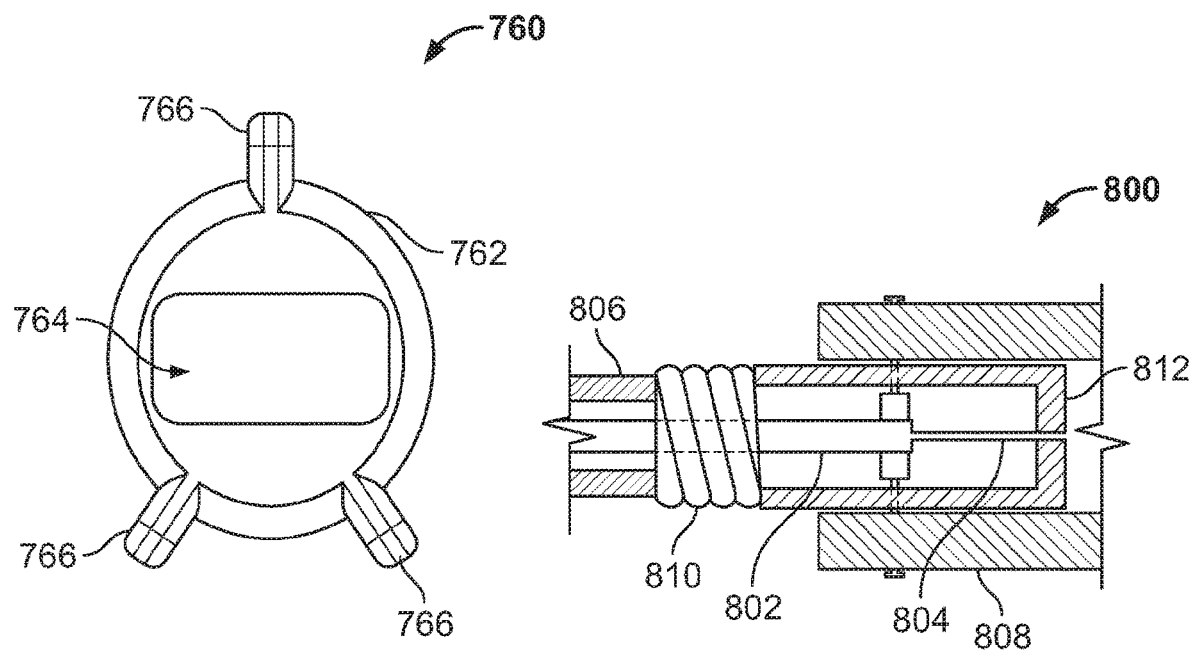
FIG. 18B
FIG. 19

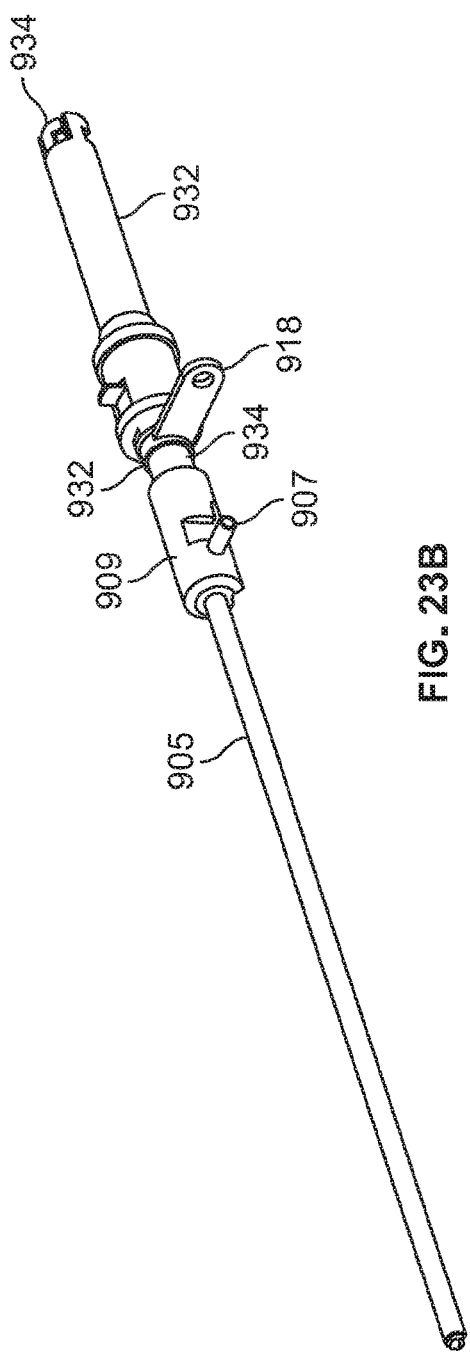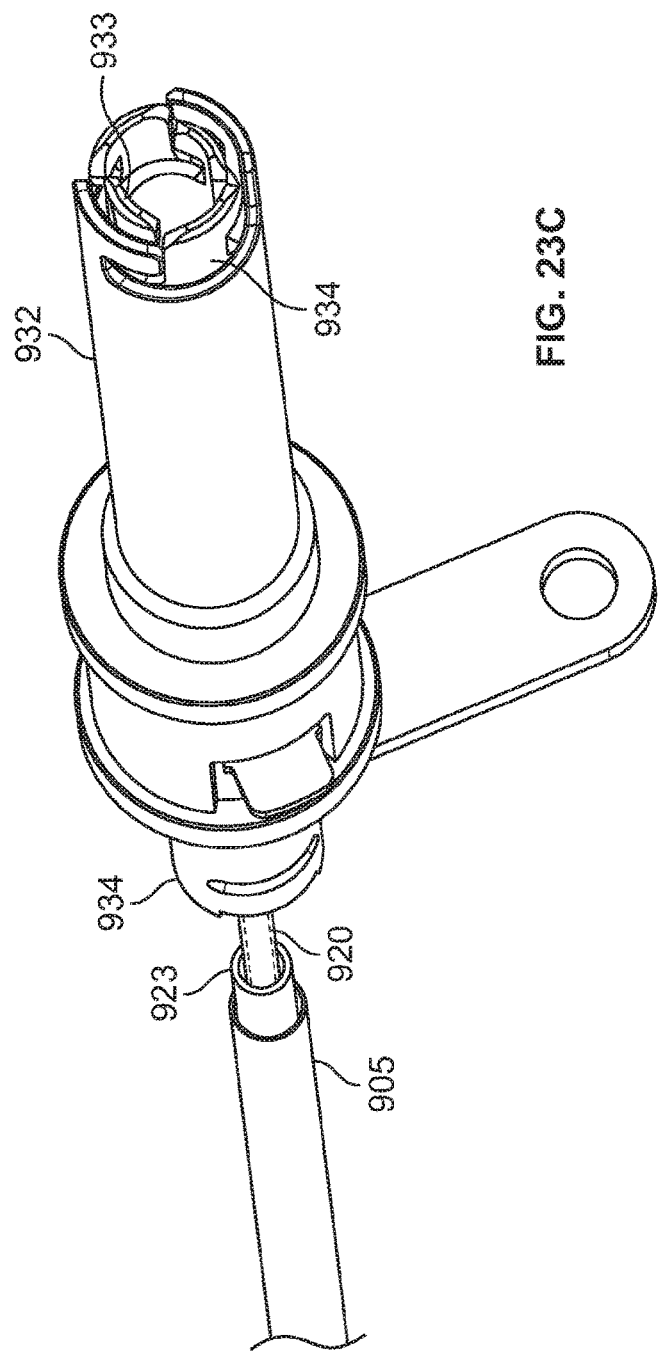

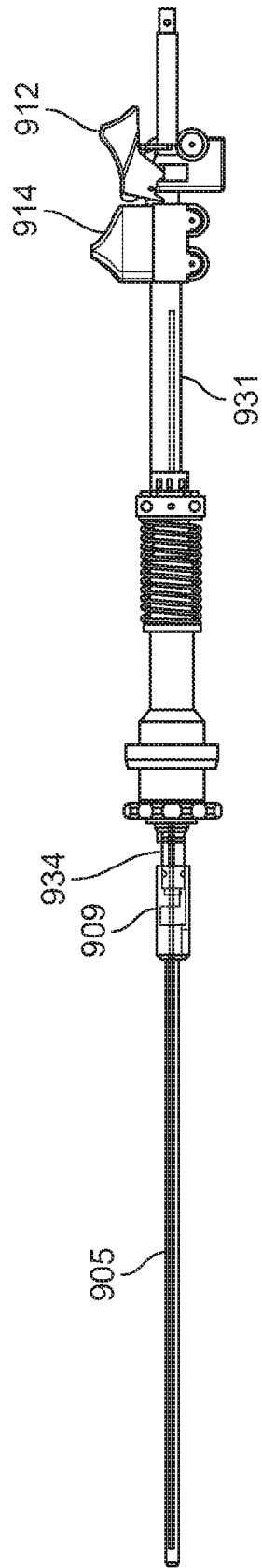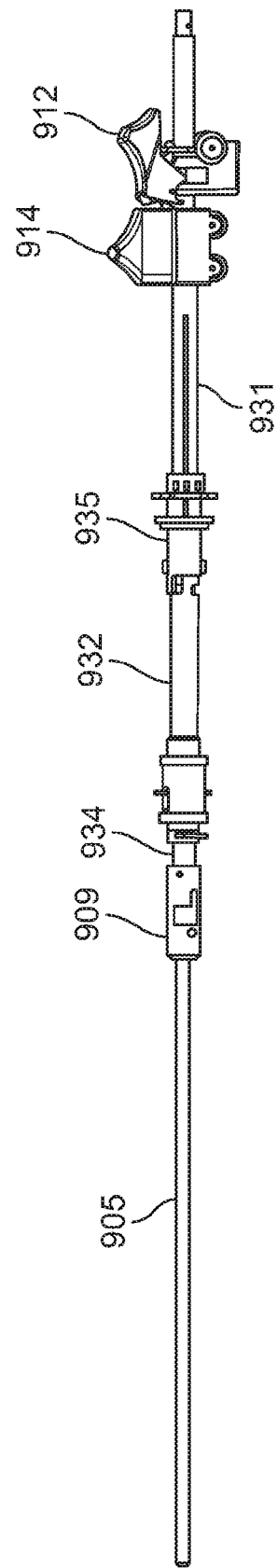

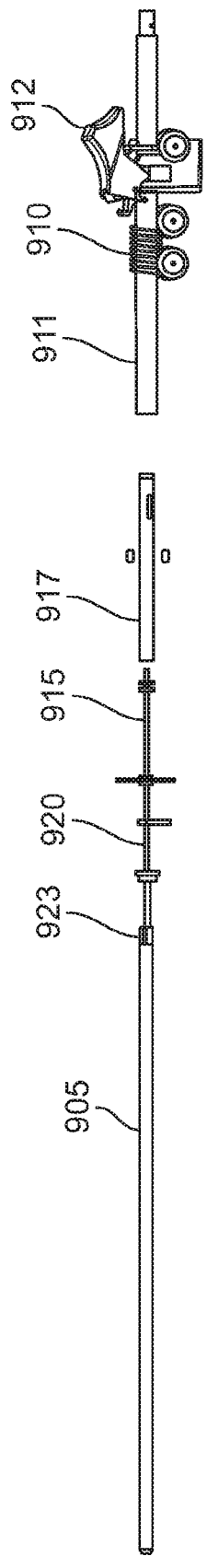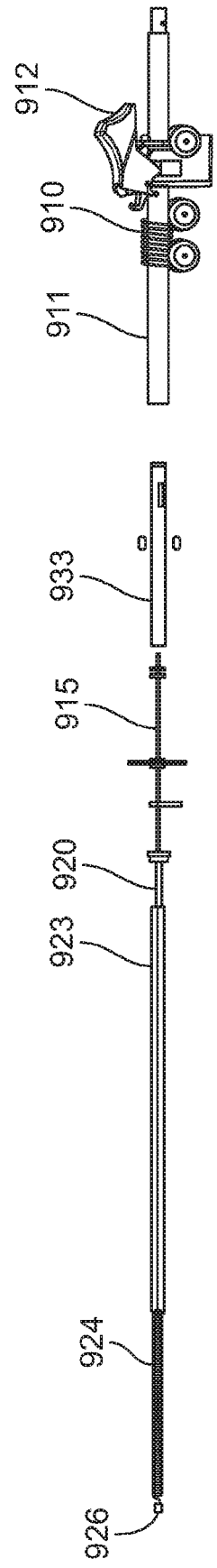
FIG. 24F
FIG. 24G

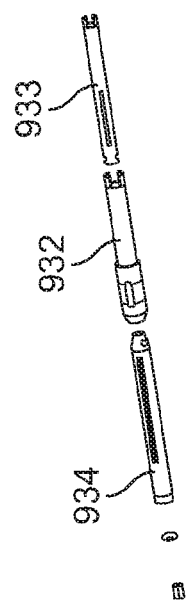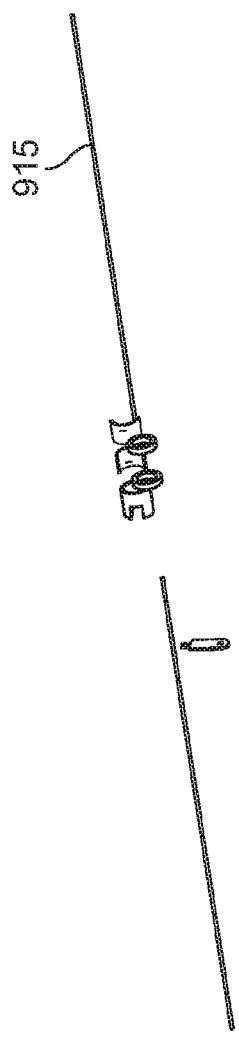
FIG. 28

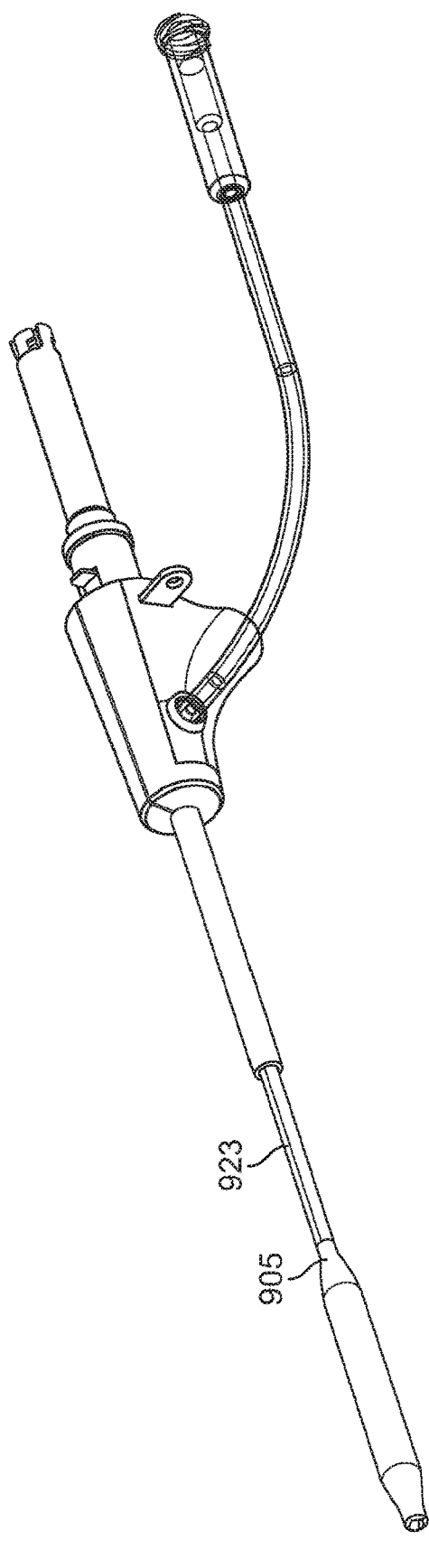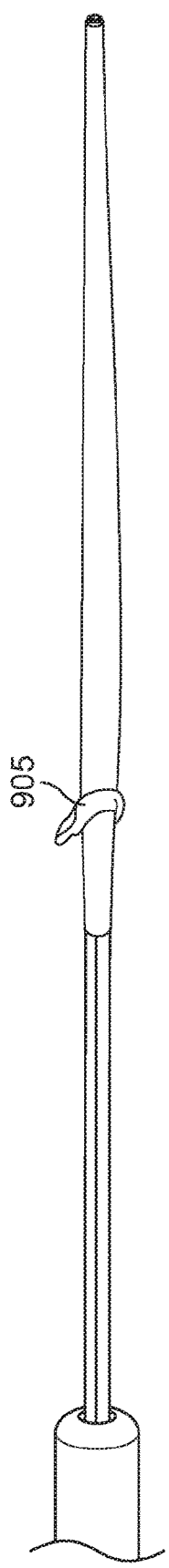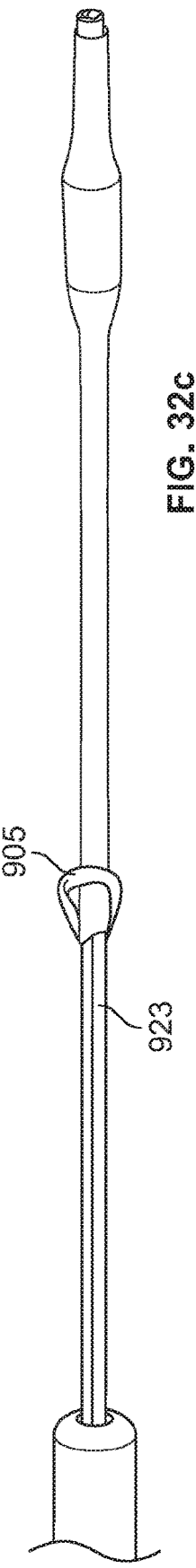

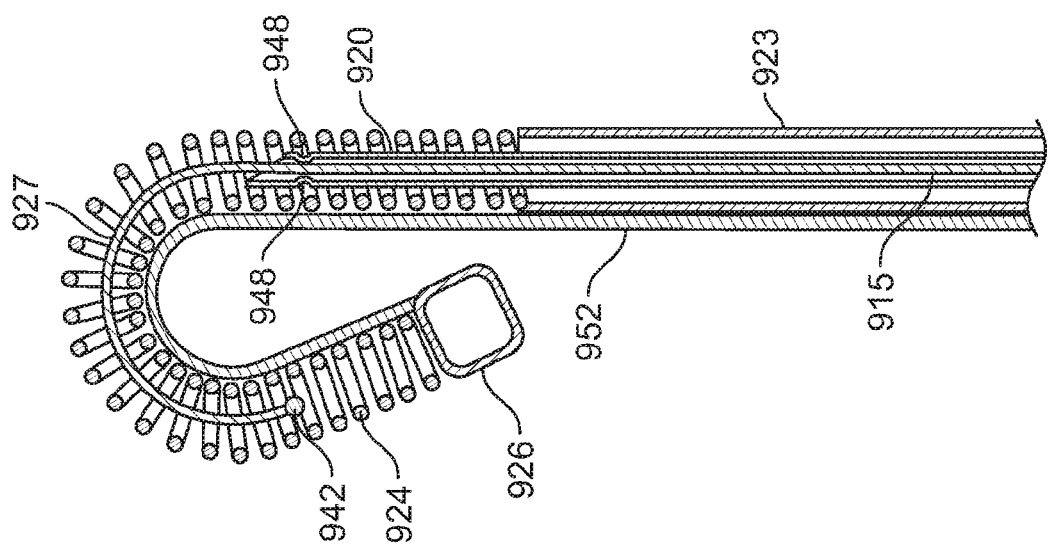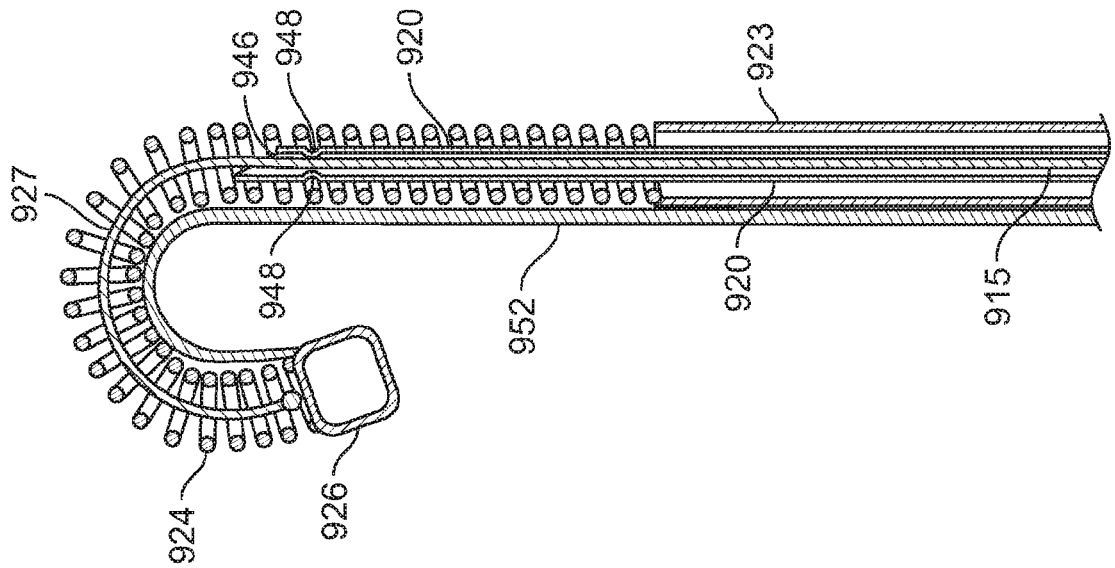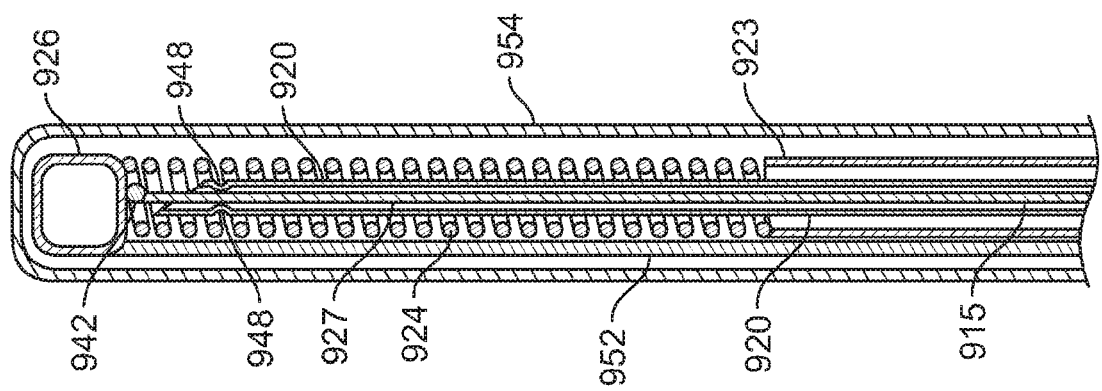

MODULAR BODY CAVITY ACCESS SYSTEM

This application is a National Stage Application of PCT/IB2017/000756, filed Jun. 6, 2017, which claims benefit of U.S. Provisional Patent Application No. 62/345,891, filed Jun. 6, 2016, the disclosures of which are hereby incorporated by reference herein in their entireties. To the extent appropriate, a claim of priority is made to each of the above disclosed applications.

TECHNICAL FIELD

This disclosure is related to medical devices and methods. More specifically, the disclosure is related to medical devices for accessing body cavities, such as paranasal sinuses.

BACKGROUND

Minimally invasive and less invasive surgical/medical procedures are becoming more and more prevalent, as physicians and inventors develop effective methods and devices to treat different diseases in ways that are less harmful to the body and require less recovery time. In many of these procedures, long thin endoscopes, catheters, access sheaths and the like are used to navigate through the patient's body to the operative site and then to perform the procedure. For example, long, flexible devices may be passed through blood vessels, nostrils, the gastrointestinal system, or the urinary tract to arrive at an operative site. In many cases, it can be very challenging to navigate such devices through sometimes very narrow, tortuous anatomical passageways, and it can be just as challenging to visualize the navigation as well as the procedure itself. Although great advances have been made in minimally invasive and less invasive surgical devices and techniques, additional improvements would still be desirable. Also, even some more invasive surgical procedures might benefit from improved visualization devices and/or access devices.

Functional endoscopic sinus surgery (FESS) is the most common type of surgery employed to treat chronic rhinosinusitis (CRS) and is one of the surgical procedures discussed in this application. In a typical FESS procedure, an endoscope is advanced into the nasal cavity along with one or more rigid surgical instruments. The surgical instruments are used to resect soft tissue and/or bone, ablate tissue and suction blood and debris. In most FESS procedures, the natural ostium of at least one paranasal sinus is surgically enlarged, to improve drainage from the sinus cavity. The endoscope provides direct visualization of most of the surgical field; however, certain anatomic structures (e.g., the uncinate process, ethmoidal cells, and the frontal recess) obstruct the line of sight to hidden parts of the surgical field. Moreover, anatomic variations (e.g., septal deviation) often further limit the access to the area that requires treatment. Therefore, to adequately view the entire surgical field through the endoscope and safely remove diseased or hypertrophic tissue or bone, the physician is often forced to remove or at least modify normal, healthy anatomic structures, thereby inflicting substantial collateral damage and trauma.

FESS is only one example of a procedure that would benefit from an endoscope that could more easily navigate through and around anatomical structures. Several other examples of minimally invasive or less invasive devices and methods for their use are described in U.S. Pat. Nos. 6,251,115; 5,788,713; and 7,625,356. Although many advances have been made, there is still a need for improved devices and methods for minimally invasive and less invasive surgical procedures.

BRIEF SUMMARY

This disclosure describes various embodiments of a device, system and method for accessing anatomical structures in a human or animal body, such as body cavities, one example of which is the paranasal sinuses. Generally, the embodiments include a steering mechanism coupled with an endoscope, catheter, sheath or any other suitable tool (or generally referred to as a "substrate"). The steering mechanism includes three components—a rigid member, a curved member and a flexible member. The rigid member has a default straight configuration and is the most rigid of the three components. The curved member has a default curved configuration and is more rigid than the flexible member but less rigid than the rigid member. The flexible member has a default straight configuration and is the least rigid of the three members. Details regarding these components and their function are described further below.

In one aspect of the disclosure, a system for accessing a paranasal sinus cavity of a patient includes a sinus access member coupled with a handle. The sinus access member includes: a rigid support tube; a curved shape memory member slidably disposed at least partially within the rigid support tube, where the curved shape memory member assumes a default curved shape when advanced out of a distal end of the rigid support tube; a flexible tube slidably disposed over at least part of the curved shape memory member, where the flexible tube assumes the default curved shape of the curved shape memory member when the flexible tube resides over the curved shape memory member; and a proximal coupling end. The handle includes: an engagement mechanism at a distal end for releasably attaching to the proximal coupling end of the sinus access member; a housing; a curving slider coupled with the housing and releasably coupled to a proximal end of the curved shape memory member for extending and retracting the curved shape memory member through the distal end of the rigid support tube; and an extension slider coupled with the housing and releasably coupled to a proximal end of the flexible tube for extending and retracting the flexible tube relative to the curved shape memory member and the rigid support tube. The rigid support tube is fixed to the handle when the sinus access member is attached to the handle.

In some embodiments, the handle may further include a spring clutch coupled with the curving slider and the extension slider. Optionally, the sinus access member may further include an electronics port for providing at least one of power or data transfer to the handle. In some embodiments, the handle further includes a grip member extending from an outer surface of the housing to facilitate holding the handle. In some embodiments, the sinus access member may further include a battery housing, a wireless data transmitter, a fluid delivery port and/or a light source. In some embodiments, the curving slider and the extension slider may be combined into one sliding button, such that the curving slider is actuated when the sliding button is depressed when advanced or retracted, and the extension slider is actuated when the sliding button is not depressed when advanced or retracted.

The proximal coupling end of the sinus access member may couple with the engagement member of the handle in such a way that the sinus access member can rotate relative to the handle about a longitudinal axis drawn through the sinus access member and the handle. In some embodiments, the handle may further include a rotational indexing port for detachably receiving and engaging a working tool, whereby the working tool is steerable and extendable by actuating the curving slider and the extension slider when the working tool is received in and engaged with the indexing port. In some embodiments, the sinus access member may further include a working tool channel configured for passage of a working tool therethrough. For example, the working tool may include, but is not limited to, one or more cameras, optical fibers, textile threads, metal threads, light sources, swabs, tweezers, sample collection containers, sample collection devices, suction tubes, irrigation tubes, injection tubes, balloons, dilation tools, ultrasound probes, ultrasound waveguides, infrared imaging devices, probes, sensors, stylets, and/or guide wires. In some embodiments, the working tool(s) may be included as part of the system. In some embodiments, the working tool channel may be a lumen in the flexible tube.

In various embodiments, a radius of curvature of the curved member in the default curved shape may be between 2 millimeters and 5 millimeters. In some embodiments, the flexible tube may be made of a shape memory material. In some embodiments, the flexible tube may be disposed over at least part of the rigid tube. In one embodiment, the flexible tube may be a spring wrapped in polytetrafluoroethylene (PTFE) perpendicularly to a longitudinal axis of the flexible tube. Optionally, a distal head may be coupled with a distal end of the flexible tube, and the distal head may include a working tool. For example, the working tool may be a camera, and the system may also include wires coupled with the camera for transferring image signals. The wires may be positioned along the inner curvature of the flexible tube when the flexible tube is curved by the curved shape memory member. Some embodiments may further include illuminating fibers coupled with the distal head and positioned along the inner curvature of the flexible tube.

In some embodiments, the curved shape memory member may include a rounded distal tip and a curve immediately proximal to the rounded distal tip. For example, the rounded distal tip may have a shape such as a bead or a ball. In some embodiments, the rigid tube may include a slanted distal tip, where a tallest point of the slanted distal tip faces into an inner curvature of the curved shape memory member. In some embodiments, the system may further include a control unit removably coupled with the handle and/or the sinus access member for providing power and/or data signals to the system.

In another aspect of the present disclosure, a method for accessing a treatment area in a patient may involve: advancing a distal end of a sinus access device in a straight configuration through a nostril into a nasal cavity; sliding a first slider on a handle of the sinus access device to advance a curved shape memory member out of a distal end of a rigid tube of the sinus access device, thus allowing the curved shape memory member to assume a default curved shape outside of the rigid tube; and sliding a second slider on the handle to advance a flexible tube of the sinus access device over the curved shape memory member and to the treatment area, where the flexible tube is sufficiently flexible to assume the default curved shape when it resides over the curved shape memory member.

In some embodiments, sliding the second slider may involve advancing the flexible tube beyond a distal end of the curved shape memory member, the flexible tube has a default straight shape, and a portion of the flexible member that extends beyond the distal end of the curved shape memory member assumes the default straight shape. In various embodiments, the treatment area may be any suitable treatment area, such as but not limited to a maxillary paranasal sinus, a frontal paranasal sinus, a sphenoid paranasal sinus, an ethmoid paranasal sinus, a Eustachian tube and/or a skull base structure. The method may also involve: sliding the second slider to retract the flexible tube over the curved shape memory member so that a distal end of the flexible tube is at or near a distal end of the curved shape memory member; sliding the first slider and the second slider to retract the curved shape memory member into the rigid tube and the flexible tube over the rigid tube; and removing the sinus access device from the nasal cavity in the straight configuration. In some embodiments, sliding the first slider to retract the curved shape memory member comprises retracting the curved shape memory member until a ball-shaped distal tip at the distal end of the curved shape memory member contacts a slanted distal tip of the rigid tube. In some embodiments, the first and second sliders are combined into one sliding button, and the first slider is actuated by depressing the sliding button and advancing or retracting it, and the second slider is actuated by not depressing the sliding button and advancing or retracting it.

In some embodiments, the method may further involve operating a working tool in the treatment area, where the working tool extends through a working channel in the sinus access device, and where the working tool may include, but is not limited to, a camera, one or more optical fibers, one or more fiber bundles, a light source, a swab, a pair of tweezers, a suction tube, an irrigation tube, an injection tube, a balloon, a dilation tool, an ultrasound probe, an ultra-sound waveguide, an infrared imaging device, a probe, a sensor, a stylet, and/or a guide wire. Optionally, the method may also include introducing fluid into the treatment area through a fluid channel in the sinus access device and in some cases suctioning the fluid out of the treatment area through the fluid channel or a suction channel in the sinus access device. In some embodiments, the method may also involve illuminating at least one of the nasal cavity or the treatment area, using an illumination device coupled with the sinus access device, and acquiring an image of the nasal cavity and/or the treatment area, using a camera coupled with the sinus access device.

In another aspect of the present disclosure, a device for accessing a paranasal sinus cavity of a patient may include a sinus access member and a handle. The sinus access member may include: a straight rigid support tube; a curved shape memory member slidably disposed at least partially within the rigid support tube, where the curved shape memory member assumes a default curved shape when advanced out of a distal end of the rigid support tube; and a flexible tube slidably disposed over at least part of the curved shape memory member and at least part of the rigid tube and having a default straight shape. The flexible tube is less rigid than the curved shape memory member, and the curved shape memory member is less rigid than the rigid support tube. The handle may include: a housing; a first slider coupled with the housing and a proximal end of the curved shape memory member for extending and retracting the curved shape memory member through the distal end of the rigid support tube; and a second slider coupled with the housing and a proximal end of the flexible tube for extending and retracting the flexible tube relative to the curved shape memory member and the rigid support tube.

In some embodiments, the first and second sliders may be combined into one sliding button. The sliding button may be pushed down/depressed to actuate the first slider and may be not pushed down/depressed to actuate the second slider. In alternative embodiments the opposite method of actuation is possible as well. In some embodiments, the handle may further include a spring clutch coupled with the first slider and the second slider. Some embodiments may further include an electronics port on the sinus access member for providing at least one of power or data transfer to the handle. The sinus access member may optionally include further include a battery housing, a wireless data transmitter, a fluid delivery port and/or a light source. In some embodiments, the sinus access member may rotate relative to the handle about a longitudinal axis drawn through the sinus access member and the handle.

In some embodiments, the sinus access member may also include a working tool channel configured for passage of a working tool therethrough. Examples of working tools include, but are not limited to cameras, optical fibers, textile threads, metal threads, light sources, swabs, tweezers, sample collection containers, sample collection devices, suction tubes, irrigation tubes, injection tubes, balloons, dilation tools, ultrasound probes, ultrasound waveguides, infrared imaging devices, probes, sensors, stylets, and guide wires. In some embodiments the working tool channel is a lumen in the flexible tube.

In various embodiments, a radius of curvature of the curved shape memory member may be between 2 millimeters and 5 millimeters. In some embodiments, the flexible tube may be a spring wrapped in polytetrafluoroethylene (PTFE) perpendicularly to a longitudinal axis of the flexible tube. Some embodiments may also include a distal head coupled with a distal end of the flexible tube, where the distal head includes a working tool. The working tool of the distal head may be, for example, a camera, and the device may further include wires coupled with the camera for transferring image signals, where the wires are positioned along inner curvature of the flexible tube when the flexible tube is curved by the curved shape memory member. In some embodiments, the device may further include illuminating fibers coupled with the distal head and positioned along the inner curvature of the flexible tube.

In some embodiments, the curved shape memory member includes a rounded distal tip and a curve immediately proximal to the rounded distal tip. For example, the rounded distal tip may have a ball or bead shape. The rigid tube may optionally include a slanted distal tip, where a tallest point of the slanted distal tip faces into an inner curvature of the curved shape memory member.

These and other aspects and embodiments are described in further detail below, in relation to the attached drawing figures.

BRIEF DESCRIPTION OF THE DRAWINGS

FIGS. 3A and 3B are side views of two different co-linear configurations of an articulating portion of an access device, such as a device for accessing a paranasal sinus cavity of a patient, according to two alternative embodiments;

FIGS. 4A-4C are side perspective views of three different configurations of an articulating portion of an access device, such as a device for accessing a paranasal sinus cavity of a patient, according to an alternative embodiment;

FIGS. 18A and 18B are perspective and front views, respectively, of a distal end of a rigid member, according to another embodiment;

FIG. 19 is side, cross-sectional view of an actuation portion of an access device, according to one embodiment;

FIG. 23B is a perspective view of a portion the steerable worktool positioning member of FIG. 23A;

FIG. 23C is a perspective view of a proximal portion the steerable worktool positioning member of FIGS. 23A and 23B;

FIGS. 24A-24G are detailed perspective and elevation views of the coupled components of the access device of FIGS. 20-23C, coupled with the handle with housing coverings and other additional components removed from both modules;

FIG. 28 is an exploded view of the distal support member portions of the access device of FIGS. 20-27;

FIGS. 32A-32C are perspective, side and side views, respectively, of a distal portion of a worktool including a balloon, according to two different embodiments;

FIGS. 33A-33C are partial cross-sectional views of an articulating distal portion of an access device, according to one embodiment;

DETAILED DESCRIPTION

Figure 1A:
FIGS. 1A-1D are schematic illustrations of an articulating portion of an access device, such as a device for accessing a paranasal sinus cavity of a patient, according to one embodiment.

The following detailed description is organized into two main sections: (1) FIGS. 1A-19 and their corresponding description, which describe general principles, mechanisms and embodiments for articulating (or "steering") any of a number of different embodiments of an access device, endoscopes, catheters, working tool or the like; and (2) FIGS. 20-35 and their corresponding description, which describe one embodiment of a paranasal sinus access system in detail, as well as several optional features and/or modification that may be made to the system, according to alternative embodiments.

In general, the embodiments described herein include an articulating or steering mechanism, which may be incorporated into a steerable endoscope, access device, catheter, working tool or the like. The articulating mechanism includes three parts or components: (1) a rigid member; (2) a curved member; and (3) a flexible member. The rigid member and the flexible member have default configurations that are straight, and the curved member has a default configuration that is curved. At least two of the members are moveable longitudinally (or "translatable") relative to one another and to the third member. In some embodiments, all three members are translatable, while in others, one of the members is fixed. For example, in some embodiments the rigid member is fixedly attached to a handle, and the curved member and flexible member translate longitudinally relative to each other and to the fixed rigid member. Additionally, the curved member has an amount of rigidity that is in between that of the rigid member and the flexible member. By translating two or more of the members relative to one another, the curved member can be moved from a straight shape (inside the rigid member) to a curved shape, and in doing so, it can cause the flexible member to curve along with it. The combination of all three members can be used to alter a curvature and length of an endoscope, access device or the like, as will be described in more detail below.

The terms "rigid member" and "flexible member" are used to describe their relative flexibilities, compared to one another and to the curved member. The rigid member, in some embodiments, may be very rigid, such as a rigid metal tube. In other embodiments, however the rigid member may be relatively flexible, such as in a flexible catheter. In such an embodiment, the rigid member will still be more rigid than the curved member and the flexible member, but it may still have a degree of flexibility. Similarly, the flexible member may have a range of flexibilities, according to different embodiments. In general, therefore, these terms are used for descriptive purposes, and in any given embodiment the rigid member will be more rigid than the curved member, and the curved member will be more rigid than the flexible member. Aside from those specifications, the three members may have any suitable amounts of flexibility and rigidity, including different rigidities/flexibilities along their lengths.

In this Detailed Description, various terms are used to describe the rigid member, the curved member and the flexible member. For example, the three members are often referred to as "support members" or "supporters" below. In some of the descriptions, the rigid member may be called a "strong support member" or "strong straight support member," the curved member may be called a "curved flexible support member" or a "curving semi-rigid support member," and the flexible member may be called a "flexible straight support member" or "weak straight support member." Furthermore, the word "strong" may be used interchangeably with the words "stiff," "rigid" and "inflexible," and "strong" may be used to mean "relatively stronger or more rigid than" one or both of the other two support members. The words "curved" and "curving" are used to describe the curved support member, in that it has a default shape that is curved, in other words having a bend or curve that is at an angle greater than zero degrees, relative to a longitudinal axis of the curved support member. Whatever terminology is used below to describe the three support members of the various embodiments, the terminology itself should not be interpreted as limiting the scope of the invention as it is defined in the claims.

Additionally, this Detailed Description focuses on one particular use of an access system—i.e., for accessing, visualizing and/or passing tools into paranasal sinuses through the nasal cavities. In some embodiments, however, the devices, systems and methods described herein may be used or modified for use in any of a number of other anatomical areas of a human or animal body, for any of a number of suitable procedures and uses. For example, the articulation mechanisms described herein may be used in endoscopes, catheters and other access device for cardiovascular procedures, urological procedures and gastroenterological procedures, just to name a few. For the sake of brevity, this application will not repeat this fact of potential additional uses each time a paranasal sinus embodiment is described. The use of the paranasal sinus example, however, should not be interpreted as limiting the scope of the invention as it is defined in the claims. Also, the terms "sinus", "sinus cavity" and "paranasal sinus" may be used interchangeably herein.

Exemplary embodiments described herein provide an access system including a rigid member, a curved member, and a flexible member. The rigidity of the support members is graded in an escalating manner from the flexible member, which is the least rigid or most flexible, through the curved member and to the rigid member, which is the most rigid of the three. The curved member and/or the flexible member may be made of a shape memory material, such that it regains its original shape after being temporarily deformed. The three supporters are slidably coupled with each other, whether directly (e.g., by sliding rails, or by being arranged in a concentric configuration), or indirectly by another component (e.g., a multilumen sheath).

In one embodiment, an operator of the access system advances the three supporters, together, toward the sinus of a patient. At one point, the rigid member stops moving forward (for example, if it is attached to a handle, the user stops advancing the handle). The curved member and the flexible member are then advanced further, thus causing the flexible member and the curved member to assume a curved shape. The flexible member may then be advanced even further, beyond the distal end of the curved member, and it will follow the curve but straighten out when advanced beyond the curved member.

Reference is now made to FIGS. 1A-1D, which are schematic illustrations of an articulation or steering system 100, which in one embodiment may be incorporated into a paranasal sinus access device. (In some places in this disclosure the articulation system 100 may be referred to generally as an "access system.") Articulation system 100 includes a flexible member 102, a curved member 104 and a rigid member 106 (also referred to as "supporters 102, 104, 106"). The flexible member 102 is straight unless forced to flex, for example by encountering a rigid tissue wall or due to coupling with only unrestrained curved member 104. In the examples set forth in FIGS. 1A-1D, each of flexible member 102, curved member 104 and rigid member 106 is schematically depicted as a line for explanatory purposes. However, the supporters 102, 104, 106 can be of any suitable shape, such as bar shaped or tube shaped. In addition, the cross-sectional shape of each of the supporters 102, 104, 106 can be any closed shape, such as a rectangle, a circle, an ellipse, a crescent and the like.

Each of the three supporters 102, 104, 106 has different rigidity. The flexible member 102 is the least rigid, the curved member 104 is the next most rigid, and the rigid member 106 is the most rigid. Therefore, the flexible member 102 is also referred to as flexible member 102 (i.e., or simply as weak supporter), and rigid member 106 is also referred to as rigid member 106 (i.e., or simply as rigid member). Curved member 104 is also referred to herein as a curved member.

The three supporters 102, 104, 106 are mechanically slidably coupled with each other. The supporters can either be coupled directly, for example by sliding rails or by being arranged in a concentric configuration, or coupled via another element (e.g., by being arranged in a co-linear configuration, or in a mix of concentric and co-linear configuration, enfolded within a sheath or a sleeve). An operator of articulation system 100 can advance each of the supporters separately or advance all or some of the supporters together.

Flexible member 102 and/or curved member 104 may be made of a shape memory material (e.g., shape memory alloy or polymer). Thus, when either one of flexible member 102 or curved member 104 is forced to change from its default shape to another shape, such as when curved member 104 is constrained within rigid member 106 or when flexible member 102 is caused to curve by curved member 104, it will return to its default shape when released from physical constraint. As mentioned above, the default shape of flexible member 102 is straight, and the default shape of curved member 104 is curved.

Alternatively, flexible member 104 is made of a flexible or deflectable material. For example, the flexible member can be formed from a coil enfolded by a polymeric layer (e.g., PTFE film), for preventing fluids to pass through the coil and into the access system. In this manner, the flexible member is rigid enough to push its way along the tissues of the surrounding anatomy, and is soft enough to not damage the surrounding tissues.

Rigid member 106 is made of a material which is more rigid than that of curved member 104, such as a metal or metal alloy (e.g., steal), a rigid polymer, or the like. While the rigid member 106 is more rigid than the curved member 104 and the flexible member 102, according to some embodiments, it can be somewhat flexible or deflectable. Thereby, when the rigid member 106 is being pushed through the anatomy of the patient, it may be able to bend at least slightly, to facilitate passage through the nasal canal while minimizing damage to surrounding tissues. Alternatively, the rigid member 106 can be malleable, such that the operator can form a bend along the rigid member 106 prior to insertion into the patient, so that the rigid member 106 would fit the anatomy of the patient better. For example, a somewhat flexible, or malleable, rigid member 106 can be employed for overcoming a deviated nasal septum anatomy.

Figure 1B:
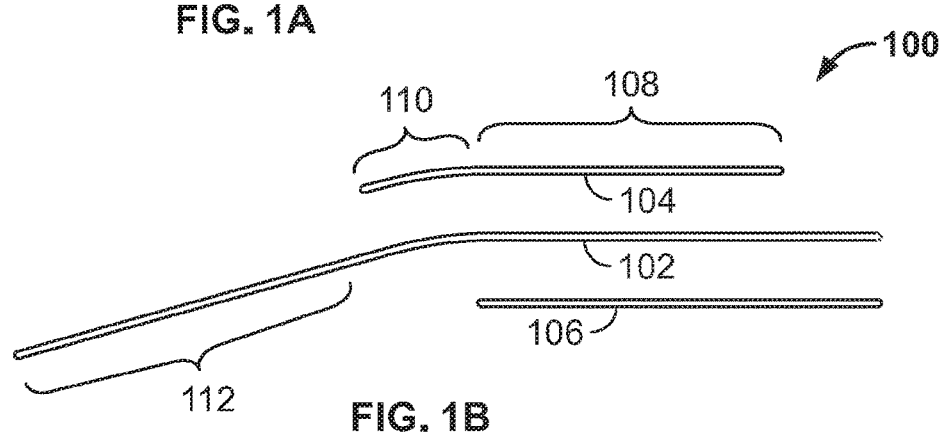
Figure 1C:
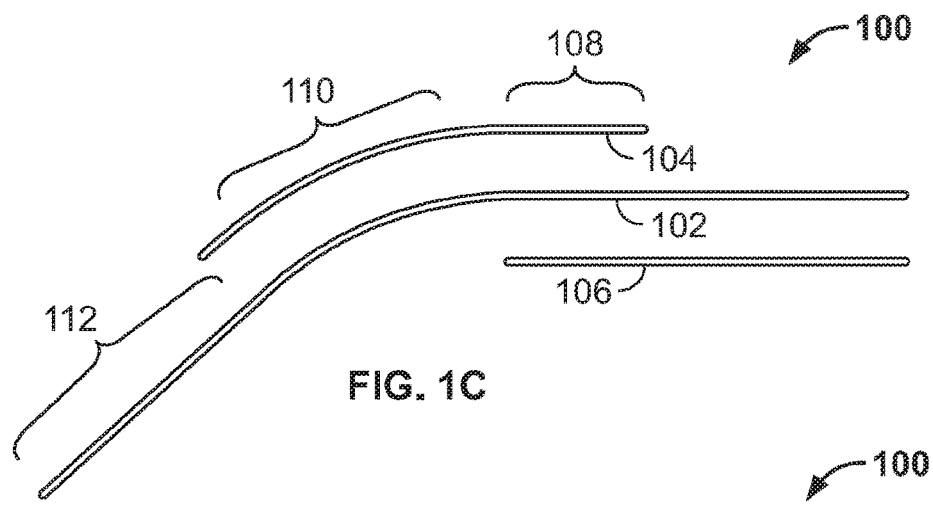
Figure 1D:
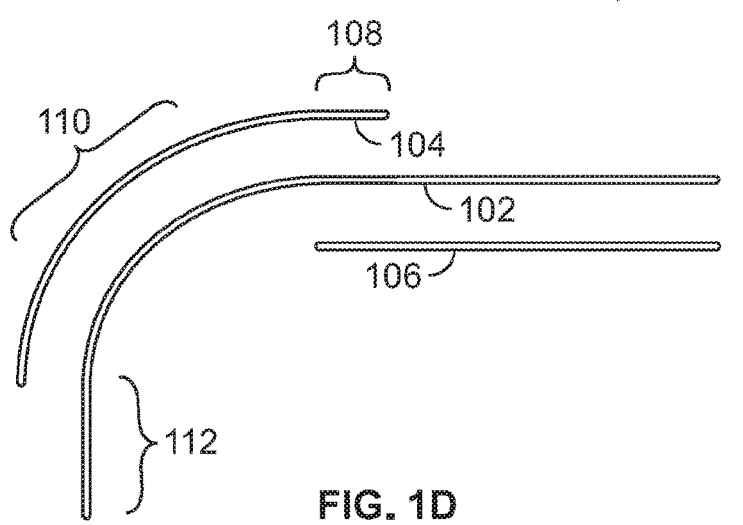

In particular, when curved member 104 overlaps a portion of (i.e., or all of) flexible member 102, curved member 104 forces the overlapped portion of flexible member 102 (e.g., the portion of flexible member 102 which overlaps portion 110 of curved member 104, in FIGS. 1B-1D) to conform to the curved shape of curved member 104. However, when a portion of flexible member 102 extends beyond the length of curved member 104, that portion of flexible member 102 (e.g., portion 112 of flexible member 102, of FIGS. 1B-1D) regains its straight shape.

Furthermore, when rigid member 106 overlaps a portion of (i.e., or all of) curved member 104 (or vice versa), rigid member 106 forces the overlapped portion of curved member 104 (e.g., portion 108 of curved member 104, in FIGS. 1B-1D) to conform to the straight shape of rigid member 106. However, when a portion of curved member 104 is slidably extended beyond the length of rigid member 106, that portion of curved member 104 (e.g., portion 110 of curved member 104, of FIGS. 1B-1D) regains its curved shape (also imposing curvature on flexible member in that overlap region).

As shown in FIG. 1A, rigid member 106 and curved member 104 are fully overlapping, and therefore rigid member 106 forces curved member 104 to conform to a straight shape. As can be seen in FIGS. 1B-1D, the curve angle of the path of articulation system 100 is determined by the radius of curvature of curved member 104, and by the length of portion 110 of curved member 104, which does not overlap rigid member 106.

The curve angle (i.e., also referred to as the curvature angle) of articulation system 100 is defined by the angle between rigid member 106 (i.e., or the portion of flexible member 102, which is parallel thereto) and portion 112 of flexible member 102. The radius of curvature of curved member 104 can be defined as the radius of an imaginary circular arc that best approximates the curve of curved member 104. Thus, the radius of curvature is a structural property of curved member 104.

Put another way, the radius of curvature of the access system is a measure of the acuteness of the bending of the access system. In particular, a small value of radius of curvature (e.g., about 2 mm) of the access system relates to an acute bend, and a larger radius of curvature value (e.g., about 5 mm) relates to a less acute bend. The curvature of the access system does not necessarily fit a circular arc, and can fit a circular, elliptical or other non-linear arc. Thus, different sections of the curved member can have different radii of curvatures.

The radius of curvature of curved member 104, and therefore of articulation system 100, is predetermined and constant. On the other hand, the curve angle of articulation system 100 is determined by the length of curved member that does not overlap rigid member 106. The length of portion 110 of curved member 104, which does not overlap rigid member 106, is controlled by the operator of articulation system 100 (i.e., who can either push curved member 104 distally with respect to rigid member 106, or pull rigid member 106 proximally). For example, the curve angle of articulation system 100 is increased with the increase in the length of non-overlapping portion 110 from the length depicted in FIG. 1B, to the length depicted in FIG. 1C, and further to the length in depicted in FIG. 1D. In summary, the curve angle of articulation system 100 is a function of the predetermined radius of curvature of curved member 104, and of the length of portion 110 of curved member 104, as controlled by the operator. Thus, the curve angle can be dynamically determined to fit the anatomy of a specific patient.

In this manner, the operator of articulation system 100 controls the curve angle of articulation system 100 by controlling the length of portion 110 of curved member 104, which extends beyond rigid member 106. During insertion of articulation system 100 into the paranasal sinus of the patient, the operator of the access system pushes all supporters together distally (i.e., in the examples set forth in FIGS. 1A-1D, the distal direction is toward the left hand side of the figure) until reaching a first point, in which a curved movement is required for accessing the sinus. The operator pushes distally both curved member 104 and flexible member 102 (i.e., while holding rigid member 106 in place) until reaching the desired curve angle. Alternatively, the operator first pushes curved member 104 distally until reaching the desired curve angle, and then pushes flexible member 102. Finally, the operator pushes distally only flexible member 102 (i.e., while holding both rigid member 106 and curved member 104 in place) until accessing the sinus or until reaching the required location within the sinus.

As the curved member conforms to the straight shape of the rigid member when both are overlapping, the access system exhibits substantially no bulges or protrusions during insertion into the nasal cavity. Only when the access system is positioned in the desired location near the paranasal sinuses, the curved member is extended from the rigid member and the access system forms a bending path. Thus, the damage to the tissues surrounding the access system on the way to the sinus cavity is reduced as the access system maintains a small cross section with no protrusions or bulges (unless desired as will be described further herein below).

In accordance with another embodiment, an access system includes several curved members each having a different radius of curvature. For example, an access system kit includes several access systems, each having curved member of different curvature, such that the operator can choose the access system curvature which best fits the anatomy of the patient. Alternatively, the access system kit includes several curved members that can be coupled with the other supporters of the access system (i.e., the strong and the flexible members). Additionally, the operator can couple several curved members for forming together a single continuous curved member having several sections of different curvatures. Thereby, the operator can determine the radius of curvature of the curved member, and thus the radius of curvature of the access system. Thereby, the operator can adjust the radius of curvature of the access system to the anatomy of the patient.

In accordance with a further embodiment, the radius of curvature of the curved member can vary along the length of the curved member. For example, the radius of curvature can be very small at the distal end of the curved member such that even when a short section thereof extends beyond the rigid member, the curvature angle of the access system is large. That is, the first few millimeters from the distal end of the curved member have a very small radius of curvature, while the rest of the curved member has a longer radius of curvature.

Referring now to FIGS. 2A-2F, side views of a distal, articulating portion of several alternative embodiments of an access device 150 are provided. As with the previous embodiment, access device 150 may be configured for use in accessing a paranasal sinus cavity of a patient. Access device 150 includes three concentric tubes: an external tube, a middle tube, and an internal tube. The three tubes have different characteristics in terms of their rigidity and shape memory (i.e., similar to the supporters 102, 104, 106 of FIGS. 1A-1D). In particular, one of the tubes serves as a straight semi-rigid tube (i.e., flexible tube or weak straight tube), another tube serves as a curved semi-rigid tube (i.e., curved tube), and the third tube serves as a straight rigid tube (i.e., rigid tube or strong straight tube).

In all of the configurations presented in FIGS. 2A-2F, a tube 152 is straight and is semi-rigid (i.e., similarly to flexible member 102 of FIGS. 1A-1D). That is, tube 152 is straight and regains its straight shape when not constrained. The rigidity of tube 152 is the lowest of the three tubes. A tube 154 is curved and is semi-rigid (i.e., similarly to curved member 104 of FIGS. 1A-1D). Tube 154 is curved and regains its curved shape when not constrained. The rigidity of tube 154 is higher than that of weak straight tube 152. A tube 156 is straight and is rigid (i.e., similarly to rigid member 106 of FIGS. 1A-1D). The rigidity of tube 156 is the highest of the three tubes.

Figure 2A:
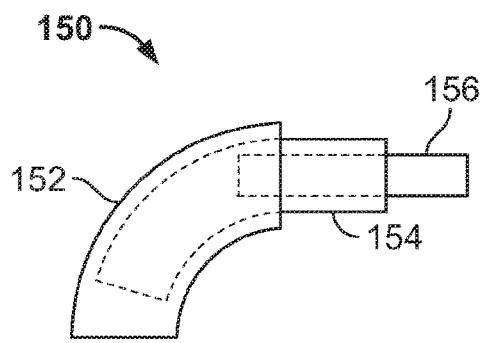
FIGS. 2A-2F are side views of different concentric configurations of an articulating portion of an access device, such as a device for accessing a paranasal sinus cavity of a patient, according to various alternative embodiments.

With reference to FIG. 2A, access device 150 includes a weak straight external tube 152, a curved middle tube 154, and a strong straight internal tube 156. Internal tube 156 slidably passes via middle tube 154, which in turn slidably passes via external tube 152. In the example set forth in FIGS. 2A-2F the distal direction is toward the left hand side of the Figure.

Access device 150 provides a route (i.e., a work channel) through which at least one tool (not shown) can reach areas within the paranasal sinus of a patient. In other words, the work channel is defined as a passage within access device 150 for enabling a work tool to access to the sinus cavity. The work channel can be a dedicated passage, such as a dedicated lumen within a multilumen sheath enfolding access device 150. The work channel can be incorporated into one of the supporters. For example, the lumen of rigid member 156 of FIG. 2A is defined as the work channel of access device 150. Alternatively, the work channel can be defined as the lumen within the flexible member. Once the access system accesses the sinus cavity, the strong and the curved members of the access system are retracted, and the lumen of the remaining flexible member functions as the work channel. The work channel can be embodied as an external sleeve or sheath enfolding the access system. Once the access system enters the sinus cavity, the supporters of the access system are retracted, and the remaining enfolding sheath functions as the work channel. The work channel can be embodied as the intra-volume between the external sheath and the supporters, or the outer most supporter.

The tube shaped supporters of FIGS. 2A-2F are merely examples, and as would be detailed further herein below, the supporters can assume any elongated shape, whether tubular or non-tubular, and have any cross-section (e.g., circular, oval, rectangular, hexagonal and the like). Thus, for example, the work channel can pass via any supporter having a lumen running therein regardless of the cross-section of the supporter. Similarly, every feature of the invention that is described herein with reference to tubular supporters, can also be employed in case of other supporters as well.

The work tool is employed for performing an action within the accessed paranasal sinus. The at least one tool can be for example, a camera, one or more optical fibers, one or more optical bundles, a swab for collecting tissue samples, a suction tube for draining the accessed paranasal sinus, an irrigation tube or an injecting tube for injecting fluids for cleaning the sinus (e.g., saline water) or for injecting other fluids into the sinus (e.g., localized drug delivery), a surgery tool for performing surgical operation in the sinus, a balloon for dilating the ostium of a sinus or opening a sinus blockage, a diagnostic tool such as an ultrasound or an infrared imaging device, a probe, a sensor, a stylet, a guide wire, and the like. Alternatively, the tool (e.g., a swab) is coupled with external tube 152. Further alternatively, the joint lumen of 152, 154 and 156 constitutes a tube through which fluids can be passed into the sinus, obviating the need for a dedicated tube to be inserted therethrough.

The access system thus provides access into the sinus cavity for at least one working tool via the work channel. By enabling all required tools to access the sinus cavity through a single access system, the operator can operate the access system and the working tools with only a single hand (i.e., single handed operation). For example, instead of maneuvering a first device (e.g., a camera endoscope) into the sinus cavity with a first hand, and maneuvering a second separate device (e.g., a tissue sampling tool) into the sinus cavity with the other hand, the operator of the access system of the invention, guides the access system into the sinus cavity single handedly, and once within can operate a tissue sampling tool while viewing the images acquired by a camera fixed to the distal end of the access system.

The route of access device 150 includes a turn or a curve in order to bypass physical or anatomical obstacles (e.g., due to anatomy of the nasal cavity and paranasal sinuses). The position of the curve along the route of access device 150 and the angle of the curve (i.e., curve angle) are controlled by the shape-memory designed into the system and by the operator of access device 150 (as will be related further hereinbelow with reference to FIGS. 20 et seq., a modular system provides a way for sinus access members 908 having different shape memory profiles to be used with the same handle 900). As mentioned above with reference to FIGS. 1B-1D, the angle of the curve (i.e., also referred to as a bend) is determined by the relative positions of strong straight tube 156 and curved semi-rigid tube 154, and by the radius of curvature of curved semi-rigid tube 154. In particular, the further that curved tube 154 extends beyond strong straight tube 156, the larger the angle of the curve. Once the operator of access device 150 sets the angle of the curve, the operator pushes weak straight tube 152 further distally in the set direction towards a selected area within the paranasal sinus of the patient. The operator can than push the tool via the work channel created by the lumens inside tubes 152, 154 and 156 towards the selected area.

Figure 2B:
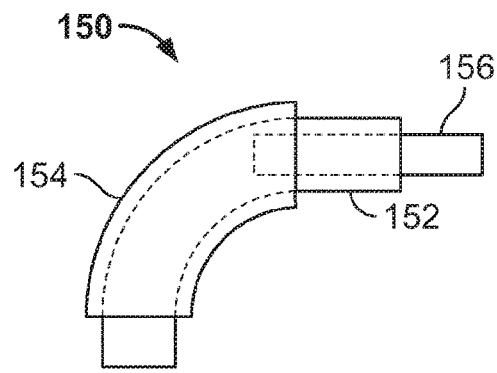
Figure 2C:
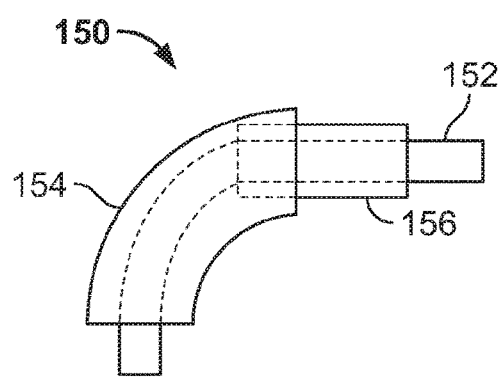
Figure 2D:
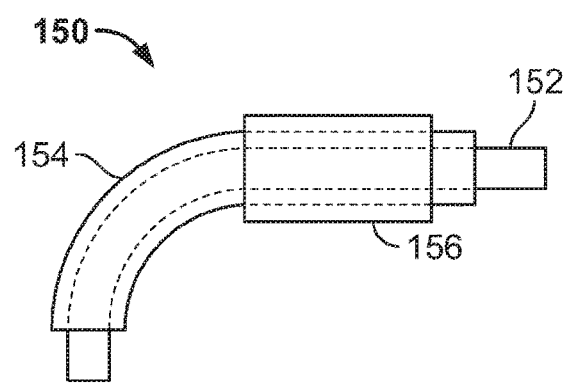
Figure 2E:
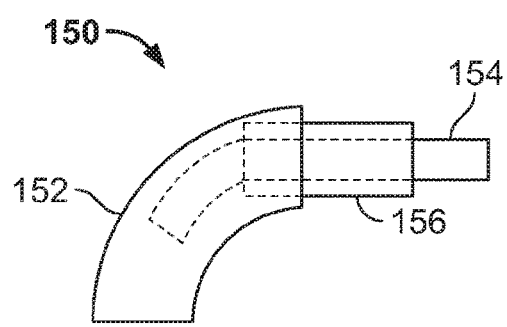
Figure 2F:
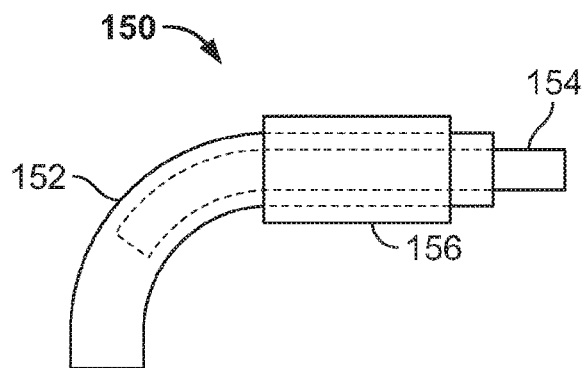

In the configuration of FIG. 2B, external tube 154 is the curved semi-rigid tube, middle tube 152 is the weak straight tube, and internal tube 156 is the strong straight tube. In the configuration of FIG. 2C, external tube 154 is the curved semi-rigid tube, middle tube 156 is the strong straight tube, and internal tube 152 is the weak straight tube. In the configuration of FIG. 2D, external tube 156 is the strong straight tube, middle tube 154 is the curved tube, and internal tube 152 is the weak straight tube. In the configuration of FIG. 2E, external tube 152 is the weak straight tube, middle tube 156 is the strong straight tube, and internal tube 154 is the curved tube. In the configuration of FIG. 2F, external tube 156 is the strong straight tube, middle tube 152 is the weak straight tube, and internal tube 154 is the curved tube.

Referring now to FIGS. 3A and 3B, two alternative embodiments of a distal portion of an access device 200 are illustrated. Access system 200 (which again may be used for accessing paranasal sinuses) may include an external sheath 208, a flexible member 202, a curved member 204, and a rigid member 206. The three supporters 202, 204, 206 pass slidably within external sheath 208 alongside each other (i.e., the supporters are co-linear). External sheath 208 mechanically couples supporters 202, 204 and 206. For example, external sheath 208 couples curved member 204 to rigid member 106, such that when they overlap, curved member 104 conforms to the straight shape of rigid member 106.

As in previous embodiments, the path (i.e., route) followed by access system 200 during insertion into the paranasal sinus includes a curve (i.e., a bend), which position and angle are controllable by an operator of access system 200. In a similar manner to articulation system 100 of FIGS. 1A-1D, the curve angle is set by the distance by which the distal end of curved member 204 extends beyond the distal end of rigid member 206.

External sheath 208 enfolds supporters 202, 204 and 206, and is made of a sealed material. Thereby, sheath 208 prevents contact between the supporters and the tissues of the patient. It is therefore not necessary to disinfect or to sterilize the supporters (and other tools and components which may reside within external sheath 208), for example, when being used among different patients. External sheath 208, which comes into direct contact with the tissues of the patient (e.g., nasal cavity and paranasal sinus) during use, is disposable. That is, external sheath 208 is a single use disposable element designed to enable the other components of access system 200 to be re-used for another patient by simply replacing external sheath 208. Alternatively, external sheath 208 is made from an easily disinfected or sterilizable material, and can be disinfected or sterilized when being used among different patients. Further alternatively, an additional single use elastic sheath may enfold 208. In addition, external sheath 208 is formed of a flexible material. Thereby, sheath 208 when extended distally beyond flexible member 202 functions as an atraumatic tip for gentle probing of sensitive anatomies.

Each of flexible member 202, curved member 204, and rigid member 206 can be bar shaped or tube shaped. The cross section of each of the supporters can be any closed shape, such as a circle, a rectangle, an ellipse and the like. In the case where two supporters or more are constructed as tubes they can be either concentric or run in parallel to each other.

With reference to FIG. 3A, flexible member 202, curved member 204 and rigid member 206 are colinear and are sliding along each other. With reference to FIG. 3B, flexible member 202 and rigid member 206 are tube shaped. Flexible member 202 slides within rigid member 206 (i.e., flexible member 202 and rigid member 206 are concentric). Curved member 204 is co-linear to flexible member 202 and rigid member 206 and slides alongside both. Alternatively, any couple of the supporters can be tube shaped and concentric while the third slides alongside both.

In accordance with another embodiment, external sheath 208 can replace flexible member 202 (i.e., such that flexible member 202 is omitted from the access system). Thereby, external sheath functions as both the flexible member and the external sheath isolating the access system from the surrounding tissues. The work channel of access system 200 can be defined as a lumen or a passage within external sheath 208.

Figure 4C:
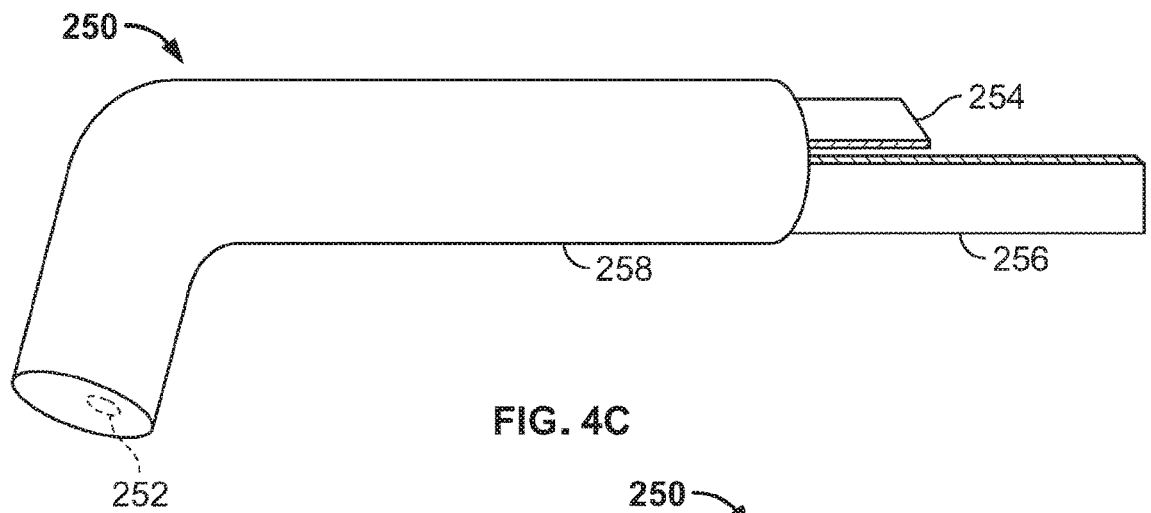
Figure 4D:
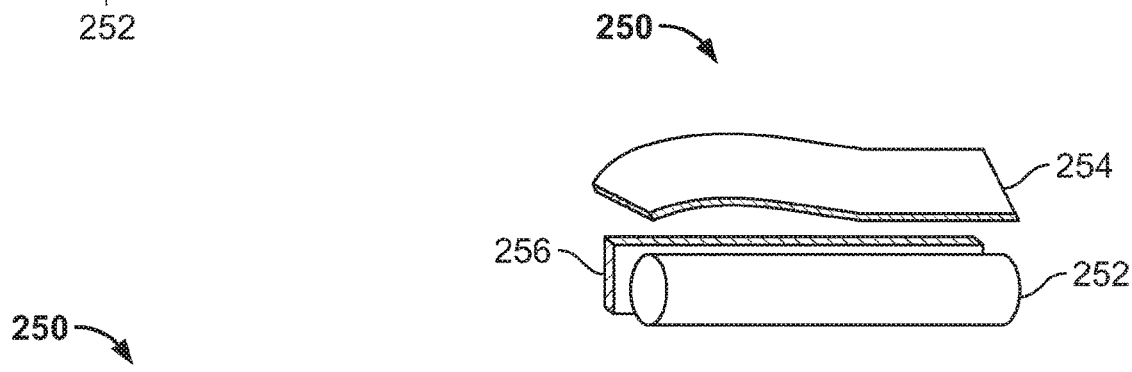
FIGS. 4D-4F are side perspective views of the access device of FIGS. 4A-4C, in which an external sheath is removed from the image to show the device's internal workings.
Figure 4E:
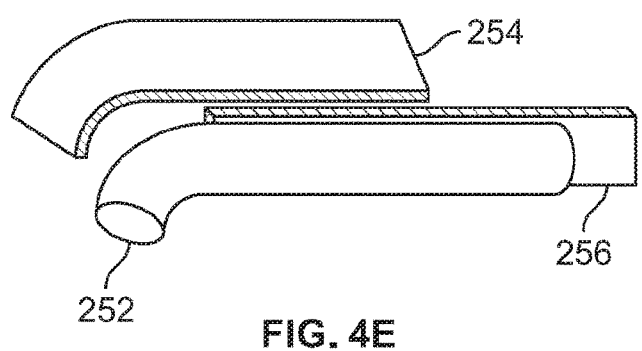
Figure 4F:
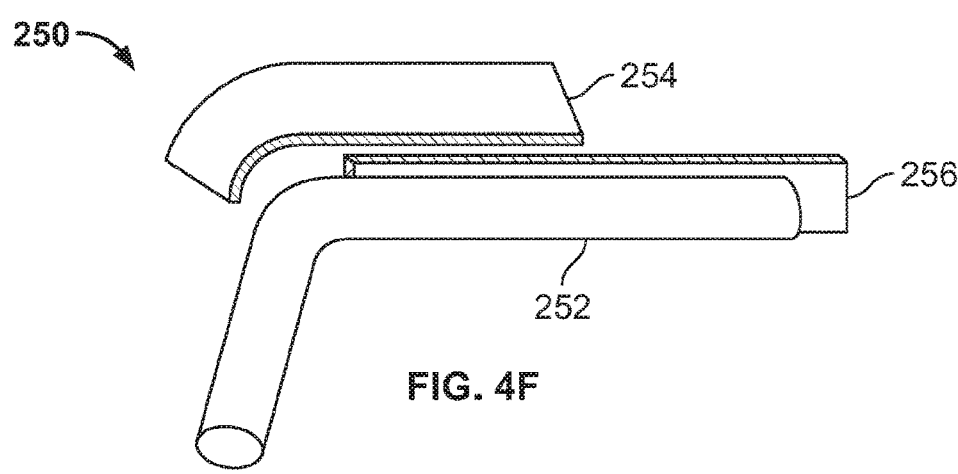

Reference is now made to FIGS. 4A-4F. FIGS. 4A-4C are schematic illustrations of a system, generally referenced 250, for accessing a paranasal sinus of a patient, according to another embodiment. FIGS. 4D-4F are schematic illustrations of the access system of FIGS. 4A-4C, in which the external sheath is removed from the image such that the internal portions of the access system are exposed to the viewer for better clarifying the operation thereof.

Access system 250 includes an external sheath 258, a flexible member 252, a curved member 254, and a rigid member 256. Each of flexible member 252, curved member 254 and rigid member 256 is similar in terms of rigidity and shape memory properties to each of flexible member 102, curved member 104 and rigid member 106 of FIGS. 1A-1D, respectively. Flexible member 252 is tube-shaped, and curved member 254 and rigid member 256 are both bar shaped. The supporters are co-linear.

Typical dimensions of an entry to a healthy sinus cavity are about 2 mm. Therefore, the maximal outer diameter of access system 250 is about 2.5 mm, and preferably a bit less, for example, 2.2 mm-2.4 mm for mitigating or preventing damage, pain, and inconvenience to the patient. However, it should also be noted, again, that dilation of the tissues being passed through may be desirable in certain circumstances.

With reference to FIG. 4A, another embodiment of an access system 250 is depicted in an initial configuration thereof, in which both rigid member 256 and curved member 254 are fully overlapping. In the initial configuration, rigid member 256 forces curved member 254 to conform to the straight shape of rigid member 256. The dotted lines in FIG. 4A indicate the distal tip of supporters 252, 254, and 256. Alternatively, the distal tip of each or some of the supporters is positioned proximally to the distal tip of sheath 258. Further alternatively, the distal tip of sheath 258 is occupied by a functional distal head, as detailed further herein below with reference to FIG. 5.

With reference to FIG. 4D, access system 250 is depicted with external sheath 258 being removed from the image, for exposing supporters 252, 254, and 256 to the viewer. As mentioned herein above with reference to FIG. 4A, and as can be seen in FIG. 4D, both curved member 254 and flexible member 252, when overlapping rigid member 256, conform to the straight shape of rigid member 256.

With reference to FIGS. 4B and 4E, an operator of access system 250 pushes curved member 254 and flexible member 252 in the distal direction (i.e., in the example set forth in FIGS. 4A-4F the distal direction is toward the left hand side of the Figure). Thereby, the overlap between rigid member 256 and curved member 254 becomes smaller, or even vanishes (i.e., depending on the distance by which curved member 254 and flexible member 252 are pushed by the operator). A portion of curved member 254 which is not overlapping rigid member 256 regains its curved shape and forces a corresponding portion of flexible member 252, to conform to the curved shape of curved member 254. Alternatively, the operator pulls rigid member 256 proximally for achieving the same effect and exposing at least a portion of curved member 254 from overlapping rigid member 256.

Shape memory materials can regain their original shape after being constrained to a different shape. However, the shape memory is not unlimited, and an element made of shape memory material which is highly deformed, may not fully regain its original shape. Curved member 254 is straightened by rigid member 256 when they are overlapping each other, and is thereby deformed from its original curved shape. For minimizing the deformation of curved member 254, curved member 254 is positioned furthest away from the direction of curve of access system 250 (i.e., at the extrados of the curved path of access system). As can be seen in FIGS. 4B and 4E, curved member 254 is positioned off-center within sheath 258. In particular, curved member 254 is positioned furthest away from the direction of curve of sheath 258 (i.e., and access system 250), thereby its radius of curvature is bigger than if it would have been concentric with sheath 258. Thus, by positioning curved member 254 off-center and away from the curve direction, the radius of curvature of curved member 254 is increased, for the same radius of curvature of sheath 258. The larger the radius of curvature of curved member 254 the less it is being deformed when straightened by rigid member 256.

With reference to FIGS. 4C and 4F, the operator of access system 250 further pushes flexible member 252 distally of both rigid member 256 and curved member 254. Thereby, flexible member 252 regains its straight shape. In the final configuration of access system 250, as depicted in FIGS. 4C and 4F, a proximal section of external sheath 258 (i.e., and accordingly of access system 250) is substantially in a straight shape. A middle section of external sheath 258, which is occupied by a portion of curved member 254 that is not overlapping rigid member 256, is in a curved shape. The section of external sheath 258 which is occupied by the portion of curved member 254 that is not overlapped by rigid member 256, is termed herein below as the "curved supported section" of external sheath 258. A distal section of external sheath 258, which is occupied solely by flexible member 252 is in a straight shape. The operator can further push distally only external sheath 258 which is floppy and functions as an atraumatic tip.

The length of each section of access system 250 is determined by the lengths of each of supporters 252, 254 and 256, and by their relative overlap, as determined by the distance each is pushed by the operator. The curve angle of access system 250 is determined by the radius of curvature of curved member 254, and by the length thereof that is not overlapping rigid member 256.

Alternatively, flexible member 252 is in the shape of an external sheath enfolding both curved member 254 and rigid member 256. In this manner, access system 250 includes only three elements, however the weak straight external sheath has to be disposed of, disinfected or sterilized, when being used among different patients.

By enfolding access system 250 with external sheath 258, the outer diameter of access system 250 is kept constant or at least continuous (i.e., the outer diameter does not change abruptly or forms a step). The continuous outer diameter stands in contrast to telescopic systems, which diameter differs for different sections thereof. The continuous external diameter reduces damage to the tissues surrounding the access system on the way to the sinus, and within the sinus itself. In some embodiment, the flexible member enfolds the other supporters and other components of the access system, thereby functioning as an external sheath or sleeve. In this case, the outer diameter of the enfolding flexible member is continuous for reducing the damage to the surrounding tissues.

In accordance with another embodiment, the access system further includes a locking mechanism (not shown), for locking all supporters together (e.g., straight flexible member, curved member and straight rigid member). In other words, the locking mechanism prevents relative movement between the supporters. Alternatively, the locking mechanism only locks two of the supporters together. For example, the locking mechanism locks the rigid member to the curved member such that relative movement is disabled (i.e., when moving one of the supporters, the other supporter is also moved in the same way). The locking mechanism is implemented, for example, by a wire coupled to both the distal end and the proximal end of the access system (i.e., or the housing). In the unlocked mode, the wire is untight (i.e., flabby), while in the locked mode the wire is stretched so that the supporters are fixed together and cannot be separately moved. Alternatively, other locking mechanisms can be employed, such as a locking sleeve, a locking component which changes its shape or rigidity when energy (e.g., thermal or electrical energy) or when pressure is applied thereto.

The locking mechanism can be either locked, such that the supporters are bound together, or unlocked such that each supporter can be moved separately. During insertion, or extraction, of the access system into, or out of, the paranasal sinus, the locking mechanism is unlocked. That is, relative movement between the supporters is enabled. Even when the locking mechanism is locked, the operator can further push or pull the supporters of the access system together (i.e., with substantially no relative movement between the supporters). When the distal tip of the access system is in the required position (e.g., at the desired location within the sinus cavity), the locking mechanism is locked, and relative movement between the supporters is disabled. Thus, for example, the access system is maintained in place while the operator retracts the system or carries out an operation (e.g., using a swab). In accordance with another example, the locking mechanism is locked prior to insertion of the access system to the body of the patient, until the rigid member is properly positioned in the vicinity of the paranasal sinus. Thereafter, the locking mechanism is released (i.e., unlocked), for allowing the rigid member to be retracted, or the curved member to be further advanced. In accordance with a further embodiment, the shape of the external sheath can be made tapering (e.g., conical) such that the cross section of the distal end thereof is smaller than the cross section of the proximal end thereof. Thereby, initial insertion of the access system is easier. Additionally, the tapering external sheath gradually dilates the anatomical path to the paranasal sinus and the paranasal sinus itself.

Alternatively, in case the access system does not include an external sheath, the access system housing, or otherwise the external-most component of the access system, is tapering. For example, in case the flexible member enfolds both the strong and the curved member, the flexible member is tapering.

In accordance with yet another embodiment, rotary or incremental encoders, or other sensors, are installed between the supporters of the access system for monitoring the relative movement between the supporters. Thereby, the position of the distal end of the access system is determined. Alternatively, the movements of the operating mechanism (not shown—e.g., levers and handles) the operator employs for operating the access system are monitored for determining the location of the distal end of the access system. Further alternatively, motion sensors (e.g., accelerometers and gyroscopes), or position detectors (e.g., ultrasonic or electromagnetic) are installed on, or in the vicinity of, the distal head of the access system for determining the position and orientation of the distal head of the access system.

The access system of the invention enables the operator to reach more than one sinus cavity (e.g., maxillary and frontal) with the same access system, and without retracting the system from the patient's body. For example, while the rigid member is maintained within the patient's nose, the operator can maneuver the access system among the different sinus cavities. Accessing two or more sinus cavities without fully retracting the access system saves time and effort to the operator, and reduces the inconvenience to the patient.

Figure 5:
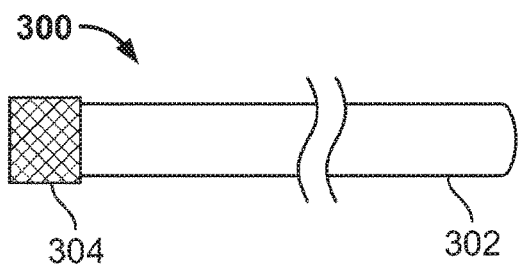
FIG. 5 is a side view of a distal portion of an external sheath of a paranasal sinus access device, according to yet another embodiment.

Reference is now made to FIG. 5, which is a schematic illustration of an external sheath 300 of a paranasal sinus access system, according to one embodiment. External sheath 300 includes a sheath body 302 and a functional distal head 304 (i.e. worktool). External sheath 300 is disposed around a sinus access system (e.g., access system 250 of FIGS. 4A-4F), which is employed for accessing a paranasal sinus of a patient. After insertion into the sinus cavity, the access system can be withdrawn from the body of the patient while external sheath 300 remains therein, for providing access therethrough for at least one tool into the sinus.

In the example set forth in FIG. 5, functional distal head 304 is a swab head 305. Swab head 305 is directed at acquiring a tissue sample or other sample from within the paranasal sinus of the patient. The operator rubs swab head 305 against the inner tissue of the sinus for acquiring tissue sample. Alternatively, functional distal head can include other tools for performing other actions within the sinus of the patient such as a dilation balloon, a camera, a heat source, a laser source, a light source, drainage nozzle, irrigation nozzle, injection element, and the like.

In accordance with another embodiment, the functional distal head of the system is rotatable (not shown). The rotatable head can be moved (e.g., rotated) separately from the supporters of the access system. Thereby, the rotatable functional distal head provides at least one additional degree of freedom to the access system. The movement of the rotatable head can be controlled, for example, by employing wires, applying thermal energy to shape memory materials or by other actuating mechanisms.

Once the access system is properly positioned within the sinus of the patient, the access system can be secured in place (e.g., by employing a locking mechanism or a balloon), such that only the functional distal head 304 can be rotated (i.e., or otherwise moved). When the rotatable head is also properly positioned at the desired location and orientation, it can be secured in place as well, and the operator can operate the functional element of the rotatable function distal head. Once the access system and the rotatable head are secured in place, at least some of the supporters can be retracted from the body of the patient.

For example, the rotatable functional distal head can include optical sensors and other optical components (e.g., lenses, prisms and mirrors) for enabling the operator to view (i.e., or to image) the interior volume of paranasal cavity. The rotatable head including the optical sensors can be rotated to enable the operator to examine different portions of the paranasal cavity.

In accordance with a further embodiment, the functional distal head includes at least one port (not shown). For example, the port can be configured as a port for transfer of fluids (e.g., gas or liquid) into or out of the sinus cavity (i.e., fluids port). The fluids port is coupled with a fluid passageway through which the fluids pass. For instance, in case the flexible member is tubular, its lumen can serve as the fluids passageway. Alternatively, the work channel of the access system can include, or can serve as, the fluid passageway.

The fluid port can be formed as an opening in the functional distal head enabling fluids passage through the distal head. The fluid passageway can be formed by a single channel (i.e., conduit), or a network of channels. The distal end of the fluid passageway (i.e., located out of the body of the patient) is connected to a fluid container and possibly to a fluid pumping mechanism (e.g., a syringe or a pump), for pumping the fluid through the fluid passageway into or out of the sinus cavity. The fluids can be, for example, saline, biological agents, chemical agents, drugs, antibiotics supporter, and the like. The fluids can be employed for irrigation, cleaning other components installed on the functional head (e.g., optical components such as a camera or illumination components such as a fiber bundle).

The fluid port, or the fluid passageway, can include a valve for regulating fluid passage therethrough. For example, the valve can be employed for switching fluid passage modes, such as switching between an irrigation mode, in which fluids are irrigating the sinus cavity, and between camera cleaning mode, in which fluids are directed toward the camera for cleaning it. The valve can be controlled by the fluid pressure or by another remote control mechanism, such as a pull wire, applying electrical energy to a piezoelectric element, and the like. The fluids pumped into the sinus cavity can be employed for collecting intracavity tissue, mucous and liquids samples by flooding the sinus cavity (e.g., with saline), collecting the flooding fluid, and filtering tissue, mucous and liquids samples therefrom.

The functional head can include several ports that can either be identical or different than each other. The ports can be formed and employed for different applications. The different ports can be coupled with separate fluid channels, containers and pumping mechanisms. The ports of the functional head can further include therapeutic or diagnostic probes (e.g., a laser source, an IR source, an ultrasound source). The ports can also include sensors, such as position sensors, velocity sensors, acceleration sensors, temperature sensors, pressure sensors, biological sensors, chemical sensors, force sensors, electro-optical sensors, and the like. For example, each image acquired by a camera installed on the functional head is associated with readings from a magnetic position sensor mounted on the head.

In accordance with yet another embodiment, the functional distal head of the access system is displaceable with respect to the access system. For example, the distal head is coupled to sheath body 302 (or to the flexible member—not shown) via a hinge. In this manner, the functional distal head can switch between a first position in which it seals the distal end of sheath body 302, and a second position in which the distal end of sheath body is open. For instance, when the operator pushes the access system into the body cavity, the distal head that includes a camera provides a frontal view of the passed through anatomy to the operator. Once the operator reaches the required location within the body cavity, the distal head is opened, thereby, enabling the operator to transfer a working tool via the body sheath.

Furthermore, the displaceable distal head may include back-to-back arrangement. In other words, a first side of the distal head includes a camera, and the other side includes a tissue sampling tool (e.g., a swab). Thus, the operator employs the camera for accessing the sinus cavity, and once positioned therewithin, the operator switches the sides of the functional head, and can employ the swab for sampling intracavity tissue, mucous and liquids. Alternatively, the back-to-back arrangement includes a first camera (and/or illumination) in a first side of the distal head, and a second camera (and/or illumination) in the other side. Thus, the operator employs the first camera for accessing the sinus cavity, and once positioned therewithin, the operator switches the sides of the functional head, and can employ the second camera while simultaneously employing a working tool within the sinus cavity.

In the examples set forth herein above with reference to FIG. 5, the functional distal head is coupled at the distal end of an external sheath. Alternatively, the functional distal head is coupled with the distal most element of the access system. For example, in case the flexible member enfolds the other supporters of the access system and functions as the external sheath, the functional distal head is coupled at the distal end of the flexible member.

Figure 6A:
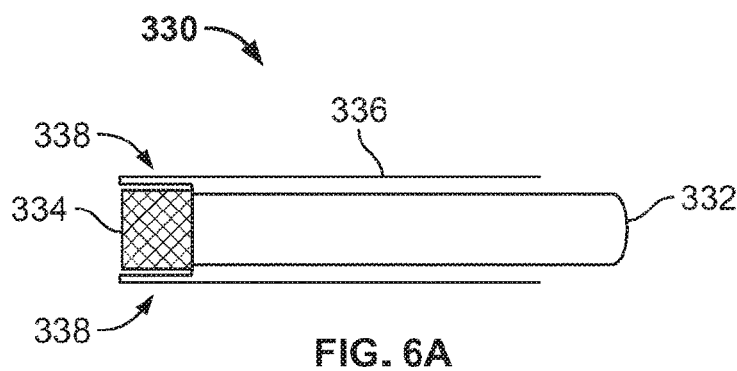
FIGS. 6A and 6B are side views of distal portions of a device for accessing a paranasal sinus cavity of a patient, according to yet another embodiment.
Figure 6B:
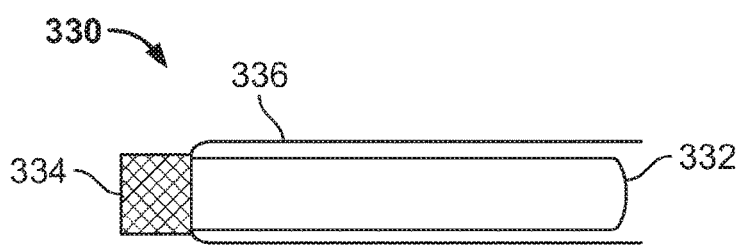

Reference is now made to FIGS. 6A and 6B, which are schematic illustrations of an external sheath 330 of a paranasal sinus access system, according to another embodiment. External sheath 330 includes a sheath body 332, a swab head 334, and a foldable sleeve 336. Foldable sleeve 336 includes an unstitched hem 338. Foldable sleeve 336 enfolds sheath body 332 and swab head 334. In particular, foldable sleeve 336 is coupled with sheath body 332 proximally to the distal end (not referenced) of swab head 334, such that unstitched hem 338 enfolds swab head 334. Each of sheath body 332 and swab head 334 is substantially similar to sheath body 302 and swab head 305 of FIG. 5, respectively.

Foldable sleeve 336 is sealed and prevents sheath body 332 and swab head 334 from coming into contact with the tissues of the patient during insertion of the access system and external sheath 330 into the paranasal sinus of the patient. Once swab head 334 is positioned within the sinus cavity, the operator may remove the access system from the body of the patient. When swab head 334 is positioned within the sinus cavity, the operator of the access system pulls foldable sleeve 336 proximally (i.e., in the example set forth in FIGS. 6A and 6B, the proximal direction is to the right hand side of the Figure) such that hem 338 is straightened, and swab head 334 is exposed. The operator rubs swab head 334 against the inner tissue of the sinus for acquiring tissue sample. The operator removes external sheath 330, including the tissue sample within swab head 334 for analyzing the sampled tissue. In this manner, the operator samples only the sinus tissue (i.e., and not other tissues on the way to the sinus tissue), thereby, increasing the accuracy of analysis of the tissue sample.

Sheath body 332 remains enfolded within sleeve 336 throughout the insertion of access system 330 into the sinus and therefore remains sterile. Therefore, the access system enfolded within external sheath 330 (i.e., in case it is not retracted by the operator) can be re-used for another patient, once sleeve 336 and swab head 334 are replaced (i.e., disposable elements), disinfected or sterilized. Sheath body 332 can further include a work channel. Thus, sheath body 332 can house at least one working tool, such as a camera. The camera can acquire images of the sinus cavity and throughout the insertion of the access system to the sinus. In a similar manner to the access system within sheath body 332, the camera is protected by sleeve 336 and is re-usable as well. Alternatively, sheath body 332 can contain other re-usable working tools, such as an ultra-sound imager, a heat source, or a laser source, as long as the tools are not required to come into contact with the sinus tissues.

Figure 7A:
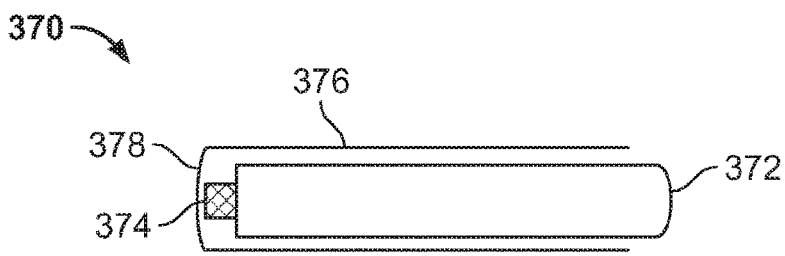
FIGS. 7A and 7B are side views of a device for accessing a paranasal sinus cavity of a patient, according to yet another embodiment.
Figure 7B:
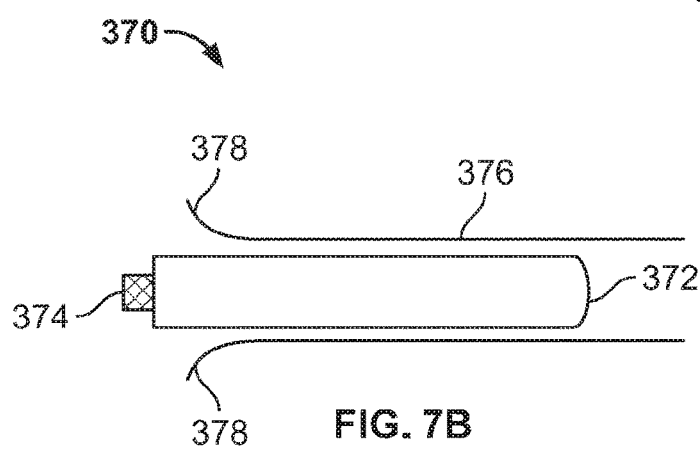

Reference is now made to FIGS. 7A and 7B, which are schematic illustrations of an external sheath 370 of a paranasal sinus access system, according to yet another embodiment. External sheath 370 includes a sheath body 372, a functional distal head 374, and a puncturable sleeve 376. External sheath 370 enfolds a paranasal sinus access system. Additionally, sheath body 372 can enfold other tools, such as a camera, or a laser source. Puncturable sleeve 376 enfolds sheath body 372 and functional distal head 374. Each of sheath body 372 and functional distal head 374 is substantially similar to sheath body 302 and functional distal head 304 of FIG. 5, respectively.

Puncturable sleeve 376 prevents sheath body 372 and functional distal head 374 from coming into contact with the tissues of the patient during insertion of the access system into the paranasal sinus of the patient. When functional distal head 374 is positioned within the sinus cavity, the operator of the access system pulls puncturable sleeve 376 proximally (i.e., in the example set forth in FIGS. 7A and 7B, the proximal direction is to the right hand side of the Figure) such that functional distal head 374 punctures the distal end of puncturable sleeve 376 and is thereby exposed. Alternatively, the operator pushes functional distal head 374 distally to puncture puncturable sleeve 376. The operator employs functional distal head for performing an action within the tissue of the patient, such as inflating a dilation balloon within the ostium of the sinus, acquiring tissue sample from the sinus, ablating tissues of the sinus, irrigating the sinus, draining fluids from the sinus, injecting substances into the sinus (e.g., localized drug delivery), and the like. Sheath 372 can either be re-usable upon disinfection or sterilization, or can be disposable. The access system sealed within the sheath body 372, as well as other working tools which are sealed within sheath body 372 (e.g., a camera) can be re-used for other patients.

Figure 8:
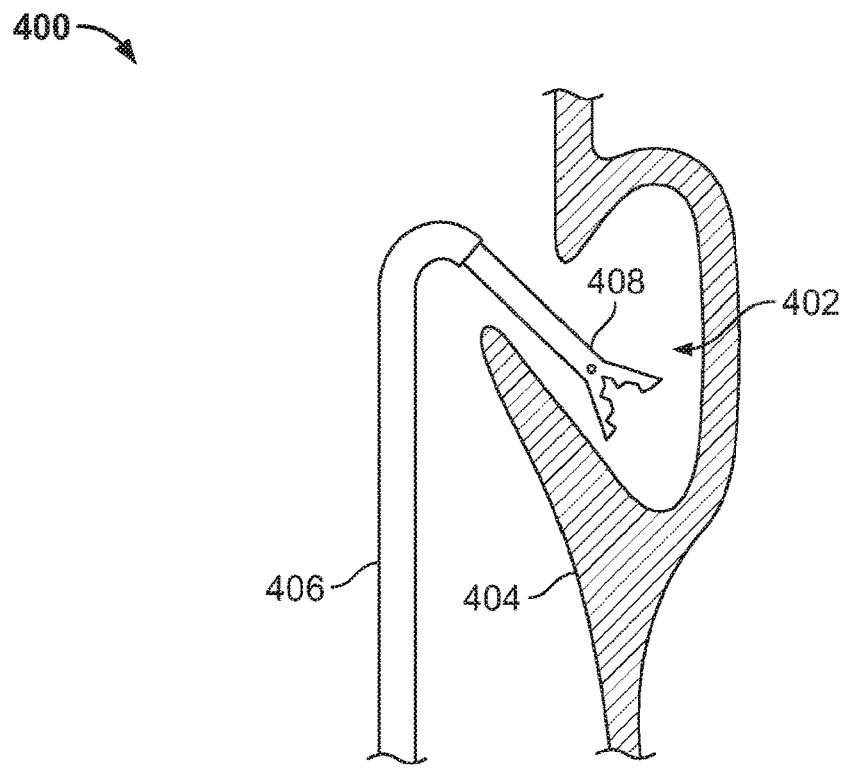
FIG. 8 is a side view of a paranasal sinus access device in position within a paranasal sinus, according to yet another embodiment.

Reference is now made to FIG. 8, which is a schematic illustration of a paranasal sinus environment, generally referenced 400, which is accessed by an access system, according to another embodiment. Sinus environment depicts a paranasal sinus cavity 402, a sinus cavity flap 404 (e.g., the uncinate process), an access system 406 and a working tool 408. Access system 406 is a paranasal sinus access system substantially similar to access system 250 of FIGS. 4A-4F. Access system 406 includes a work channel, through which an operator of access system 406 can insert working tool 408 into sinus cavity 402. Working tool 408 is a working, therapeutic or diagnostic tool for performing an action within cavity sinus 402. For example, working tool 408 can be a camera, a balloon catheter, a washing catheter, a draining catheter, a tissue ablating tool, a grasper, a biopsy collector, and the like.

As can be seen in FIG. 8, for accessing sinus cavity 402, access system 406 (i.e., and in particular the work channel within) have to maneuver around sinus cavity flap 404 and make a turn of an angle exceeding 90 degrees. Such an acute turn in a limited space as that of the anatomy of the nasal cavity and the paranasal sinuses, requires that access system 406 would maneuver to achieve a wide range of curve angles over a very small radius of curvature. In particular, for accessing sinus cavity 402, access system 406 should conform to a radius of curvature of between 2-5 mm, and achieve angles up to 180 or even greater than degrees.

As mentioned above with reference to FIGS. 4A-4F, shape memory elements regain their original shape after being deformed. However, the shape regaining is not unlimited and an element which is drastically deformed might not fully regain its original shape. With reference to FIGS. 4A-4F, curved member 254 is positioned off the center (not shown) of the cross section of sheath 258. In particular, curved member 254 is positioned at, or toward, the end of the cross section of sheath 258, which is furthest away from sinus cavity 404. That is, the curved member is positioned at, or toward, the extrados of the bend of the access system. Thereby, the radius of curvature of curved member 254 is larger than in case curved member 254 would have been positioned in the center of the cross section of sheath 258.

Additionally, curved member 254 is non-tubular, e.g., a bar shaped. A bar shaped shape memory element may withstand higher deformations than a tube shape element. Furthermore, a tube shaped element when deformed by a curvature may become oblate (i.e., its cross section becomes oval) thereby decreasing its diameter in one axis. Therefore, every element passing through curvedly deformed tube should have a diameter smaller than that of the tube for allowing for the oblation of the tube. For example, the diameter of working tool 408 should be sufficiently smaller than that of the work channel of access system 406, for allowing for the oblation of the work channel when curvedly deformed by the curved member.

In accordance with another embodiment, the curved member is formed by a wire made of shape memory material. The cross section of the wire can be of any shape, such as circular, oval, rectangular, hexagonal, and the like. Alternatively, the curved member is formed by more than a single wire. For example, the curved member is formed from two or more wires coupled together side by side. For instance, the wires can have a circular cross section, or a rectangular cross section (i.e., thereby forming together a bar shaped curved member).

In accordance with a further embodiment, the curved member is bar shaped and the rigid member is tube shaped. The rigid member includes a distal end configured to enable coupling (e.g., slidable coupling) between the two supporters. The distal end of the straight rigid member may include a curved member recess configured to receive the curved member, as depicted, for example, hereinafter in FIGS. 16A-18B. Additionally, the distal end enables the flexible member to smoothly move (e.g., slide) over the rigid member and the curved member, and in particular, over the end of the rigid member where the curved member is being curved.

Figure 9:
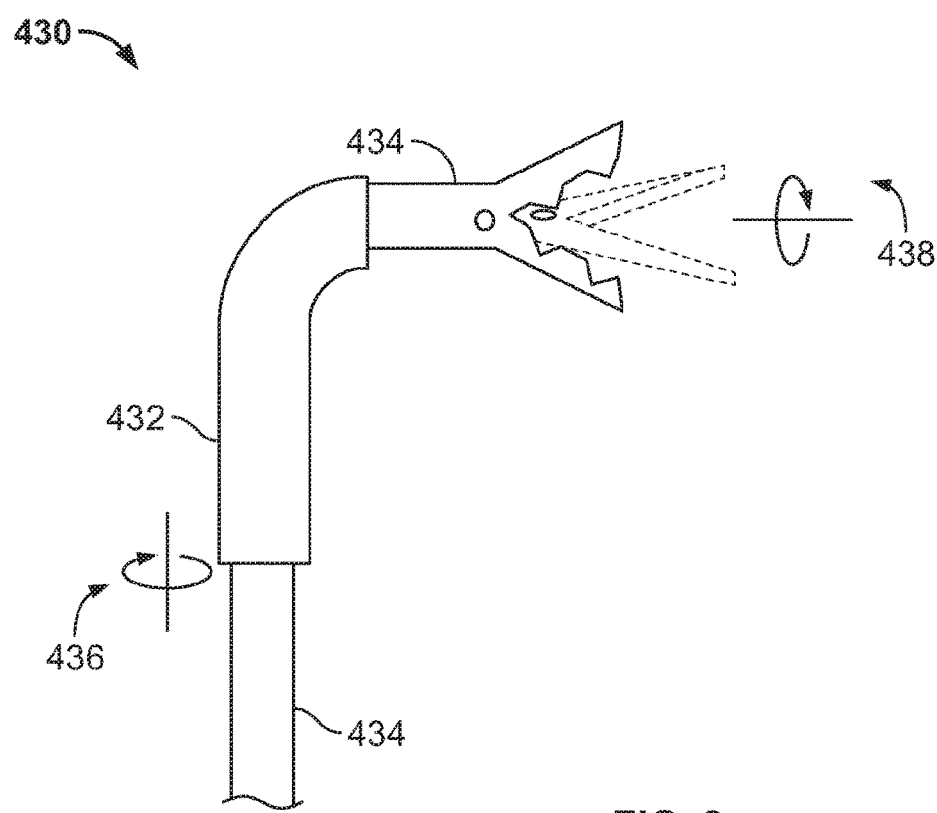
FIG. 9 is a side view of an access device, according to yet another embodiment.

Reference is now made to FIG. 9, which is a schematic illustration of an access system, generally referenced 430, constructed and operative in accordance with yet a further embodiment. Access system 430 includes an external sheath 432 and a working tool 434. Sheath 432 is substantially similar to sheath 402 of FIG. 8, and enfolds therewithin a flexible member, a curved member and a rigid member (all not shown). Working tool 434 slidably passes through a work channel (not shown) of sheath 432. As can be seen in FIG. 9, working tool 434 can be rotated around its central axis 438 without rotating sheath 432. In particular, working tool 434 rotates around axis 436 and 438 without moving sheath 432.

Figure 10:
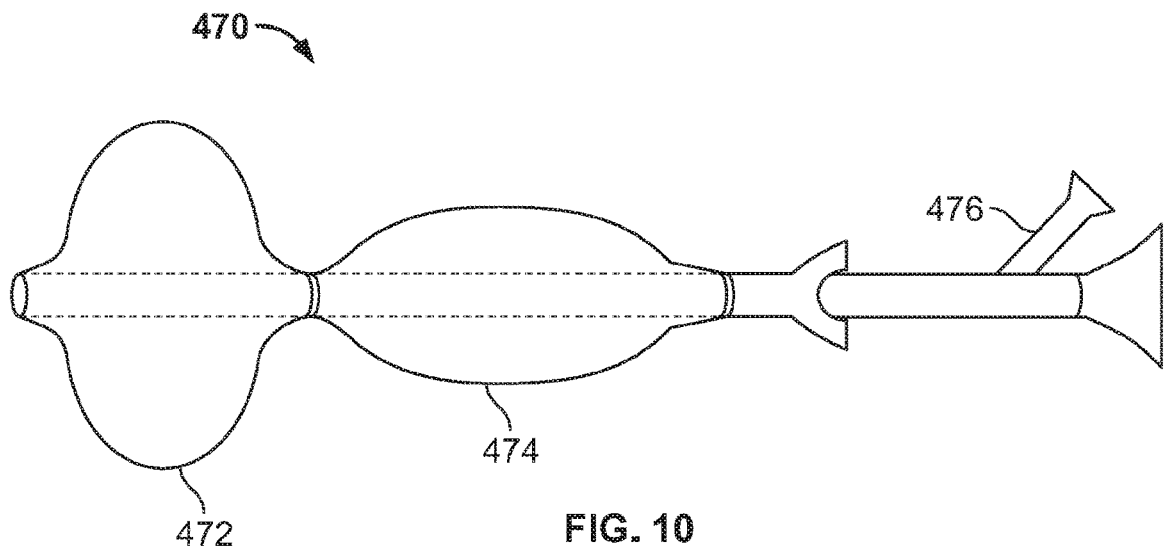
FIG. 10 is a side view of a balloon dilation catheter, according to one embodiment.

Reference is now made to FIG. 10, which is a schematic illustration of a balloon dilation catheter, generally referenced 470, according to another embodiment. Balloon dilation catheter 470 includes a first balloon 472, a second balloon 474, and a fluid channel 476. First balloon 472 and second balloon 474 are in fluid communication with each other. Fluid channel 476 is in fluid communication with both first balloon 472 and second balloon 474 for providing fluid (e.g., saline solution, air) to first and second balloons 472 and 474. Each of first balloon 472 and second balloon 474 can either be a compliant, semi-compliant or non-compliant balloon. In the example set forth in FIG. 10, first balloon 472 is a compliant or semi-compliant balloon, and second balloon 474 is a non-compliant balloon.

An operator of an access system (e.g., access system 250 of FIGS. 4A-4F) employs the access system for accessing a paranasal sinus of a patient. The operator inserts balloon dilation catheter 470 through a work channel of the access system. Alternatively, balloon catheter 470 is detachably mounted over the access system (e.g., similarly to external sheath 300 of FIG. 5).

Both first balloon 472 and second balloon 474 are deflated during insertion into the sinus cavity. The operator positions first balloon 472 within the sinus cavity of the patient, and positions second balloon 474 within the ostium of the sinus (i.e., the opening to the sinus cavity). The operator inflates both first balloon 472 and second balloon 474, for gradually broadening the ostium (i.e., increasing the diameter thereof). Second balloon 474 is constrained by the ostium and therefore can only inflate to a certain volume. First balloon 472, which is positioned within the sinus cavity, is not constrained and can be inflated to its maximal volume and stretch (i.e., in case of compliant or semi-compliant balloon).

As detailed above, first balloon 472 is in fluid communication with second balloon 474. Therefore, the pressure between balloons 472 and 474 is in equilibrium. Thus, compliant or semi-compliant first balloon 472, serves as a pressure reservoir for non-compliant second balloon 474. As second balloon 474 is pressed against the walls of the ostium of a sinus, any change in the dimensions of the ostium is compensated by a volume change of first balloon 472 for maintaining the pressure equilibrium.

First balloon 472 and second balloon 474 are maintained within the sinus cavity and the ostium of the sinus, respectively, for a period of time determined by the operator (e.g., one hour, one day or one week). The operator can remove the access system and balloon catheter 470, while maintaining balloons 472 and 474 in the sinus and ostium. After that period of time has ended, the operator removes both balloons from the sinus and ostium of the patient by re-employing the access system.

In accordance with an alternative embodiment, the access system (e.g., access system 250 of FIG. 4A) is coupled with a balloon. The operator of the access system can inflate and deflate the balloon, for example, for dilating sections of the anatomy of the patient on the way to the sinus cavity, or within the sinus cavity itself.

Further alternatively, the access system includes a dilating tube enfolding the access system. The dilating tube can be, for example, a sleeve having a tapering distal end, that enfolds the access system and that can be inflated and deflated by the operator for dilating sections of the anatomy of the patient. The dilating tube is coupled with a fluid channel running along, outside, or within, the access system. The fluid channel enables an inflating fluid (e.g., saline) to be pumped into or out of the dilating tube. The fluid channel is coupled with an inflating fluid reservoir on the proximal end of the access system, outside of the body of the patient. The dilating tube can enfold the entire length of the access system or only a section of the access system (e.g., enfolding the distal end of the access system or enfolding a section which is positioned proximally to the distal end). The operator can employ the dilating tube to dilate sections of the anatomy of the patient within the sinus cavity or on the way to the sinus cavity. Additionally, the operator can employ the dilating tube for anchoring the access system in place by inflating the dilating tube such that it snuggly fits the surrounding anatomy of the patient. Thereby the inflated dilating tube prevents the access system from sliding distally or proximally from its current location.

Figure 11:
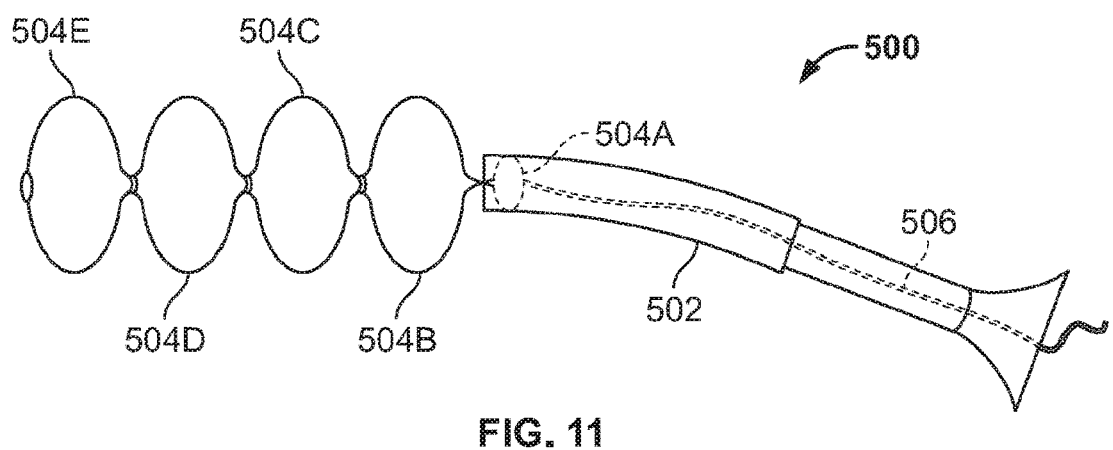
FIG. 11 is a side view of a balloon dilation catheter, according to another embodiment.

Reference is now made to FIG. 11, which is a schematic illustration of a balloon dilation catheter, generally referenced 500, constructed and operative in accordance with yet a further embodiment. Balloon dilation catheter 500 includes a balloon holding sleeve 502, a series of balloons 504A, 504B, 504C, 504D, and 504E, and a balloons inflation channel 506. Each of balloons 504A-504E is in fluid communication with adjacent balloons. Balloons inflation channel 506 is in fluid communication with balloons 504A-504E.

An operator inserts balloons 504A-504E into the ostium of a paranasal sinus of a patient by employing an access system (e.g., access system 250 of FIGS. 4A-4F). During insertion, balloons 504A-504E are enfolded by balloon holding sleeve 502, and are deflated. When arriving to the ostium, the operator pulls balloon holding sleeve 502 proximally to expose at least one of balloons 504A-504E. In the example set forth in FIG. 11, the operator exposes four balloons 504B-504E, while maintaining a single balloon 504A enfolded within balloon holding sleeve 502. Thereby, the operator controls the length of the balloon employed in the dilation procedure. Balloon dilation catheter 500 can include any number of balloon (e.g., two balloons or eight balloons).

Once balloons 504B-504E are positioned within the ostium of a sinus, the operator can remove the access system while maintaining balloons 504A-504E, balloon holding sleeve 502 and balloons inflation channel 506 within the patient. It is noted, however, that the proximal end of balloons inflation channel 506 remains outside of the body of the patient. The operator inflates balloons 504B-504E via balloons inflation channel 506 for applying pressure on the walls of the ostium for increasing the diameter thereof. After a period of time, the operator can deflate balloons 504B-504E, and remove balloons 504A-504E, holding sleeve 502 and balloons inflation channel 506 by employing the access system.

Figure 12A:
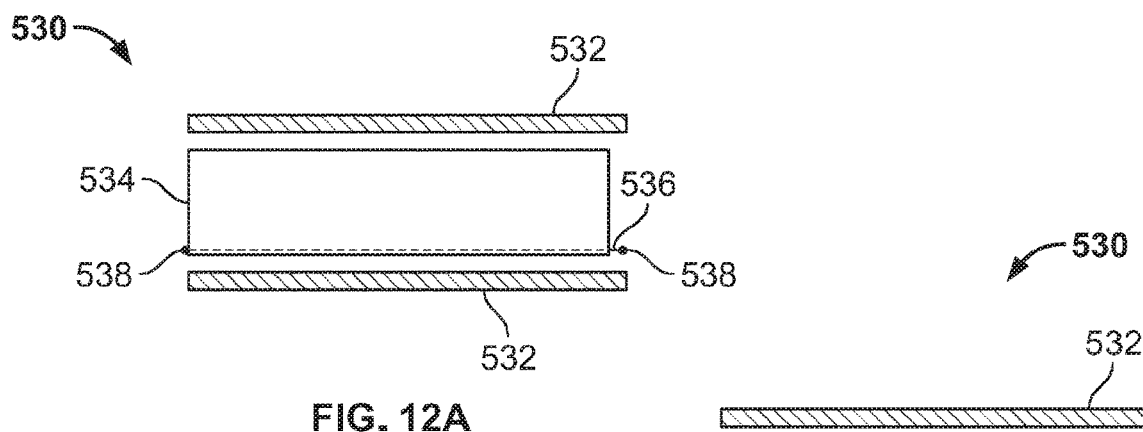
FIGS. 12A-12C are side, partial cross-sectional views of an articulating portion of an access device, according to another embodiment.
Figure 12B:
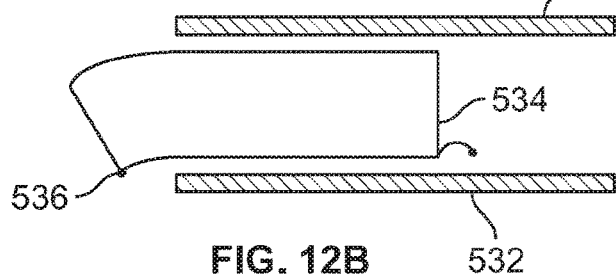
Figure 12C:
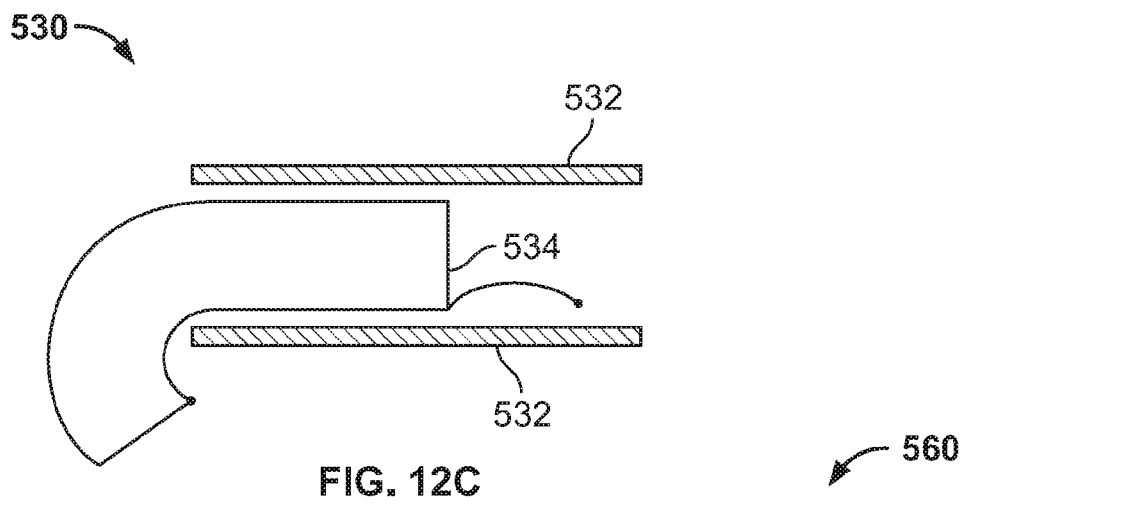

Reference is now made to FIGS. 12A-12C, which are schematic illustrations of a system for accessing a paranasal sinus of a patient generally referenced 530, according to another embodiment. Access system 530 includes an external sheath 532, an inner curving tube 534, and a pull wire 536. External sheath 532 enfolds inner curving tube 534. Pull wire 536 runs through a dedicated wire channel (not shown) on the perimeter of curving tube 534. Pull wire includes two restrain beads 538 at either end thereof. Sheath 532 is formed of a rigid material. Curving tube 534 is formed of a flexible material which can be flexed upon appliance of pressure. Additionally, system 530 can further include a straight semirigid supporter (i.e., a flexible member—not shown), slidably coupled within curving tube 534. Further additionally, a tool can also slide through curving tube 534 along the flexible member.

With reference to FIG. 12A, curving tube 534 is slidably coupled within sheath 532 and is pushed distally (i.e., in the example set forth in FIGS. 12A-12C the distal direction is toward the left hand side of the Figure) by an operator of access system 530. With reference to FIG. 12B, once the operator wants to curve access system 530 around an obstacle (e.g., sinus cavity flap 404 of FIG. 8), the operator pulls wire 536 while pushing curving tube 534 proximally, thereby, curving tube 534 begins to curve. With reference to FIG. 12C, the operator can control the curve angle of curving tube 534 by continuing to push curving tube distally, while pulling wire 536 proximally, until reaching the desired curve angle. It is noted, that the operator can pull wire 536, while curving tube is positioned within sheath 532. Thereby, sheath 532 would constrain curving tube 534 from curving in a similar manner to a rigid member.

Figure 13:
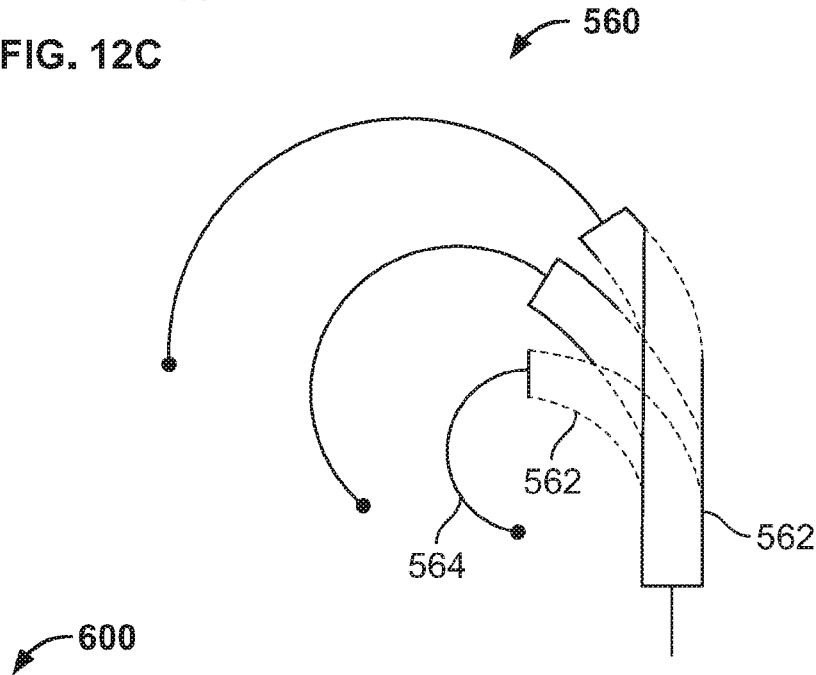
FIG. 13 is a schematic illustration of an articulating portion of an access device with a curved member, according to another embodiment.

Reference is now made to FIG. 13, which is a schematic illustration of a curved member producer, generally referenced 560, constructed and operative with yet a further embodiment. Curved member producer 560 includes a radius shaper 562 and a curved member 564. Radius shaper 562 is made of a shape memory material and is curved. Alternatively radius shaper 562 is a steerable sheath (e.g., curving sheath 534 of FIGS. 12A-12C, or other deflection mechanism). Radius shaper (i.e., in case it is made of shape memory material) 562 is more rigid than a flexible member (not shown) and is less rigid than a rigid member, both of an access system (e.g., system 100 of FIGS. 1A-1D). Thus, when radius shaper 562 extends beyond the rigid member, i.e. non-overlapping areas, radius shaper 562 regains its original curved shape. In the examples set forth in FIG. 13, three alternative radius shapers 562 are shown, having different curvatures. Curved member 564 is elongated shaped rigid material exhibiting plastic behavior. An operator of the access system pushes curved member 564 through radius shaper 562, and thereby bends curved member 564 at a radius determined by the radius of curvature of radius shaper 562. The operator determines the angle of curve of curved member by controlling the length of curved member extending through radius shaper 562.

Figure 14A:
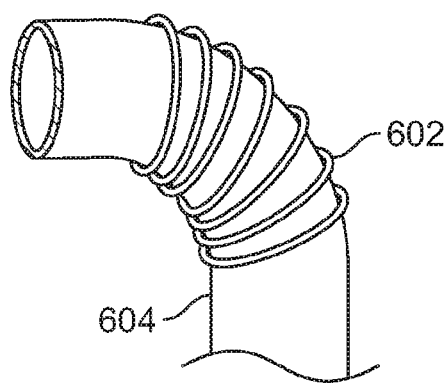
FIGS. 14A-14D are perspective views of articulating portions of an articulating device, where each embodiment has a curved member, according to four different alternative embodiments.

Reference is now made to FIGS. 14A, which is a schematic illustration of a curved member, generally referenced 600, constructed and operative with yet another embodiment. Curved member 600 includes a shape memory portion 602 and a flexible portion 604. Shape memory portion 602 regains its original shape after being deformed and thereby gives curved member 600 its curved shape when not overlapping with a rigid member of an access system. In the example set forth in FIG. 14A, flexible portion 604 is in the shape of a tube, and shape memory portion 602 is in the form of a curved helical wire. Shape memory portion 602 is wound around flexible portion 604.

Figure 14B:
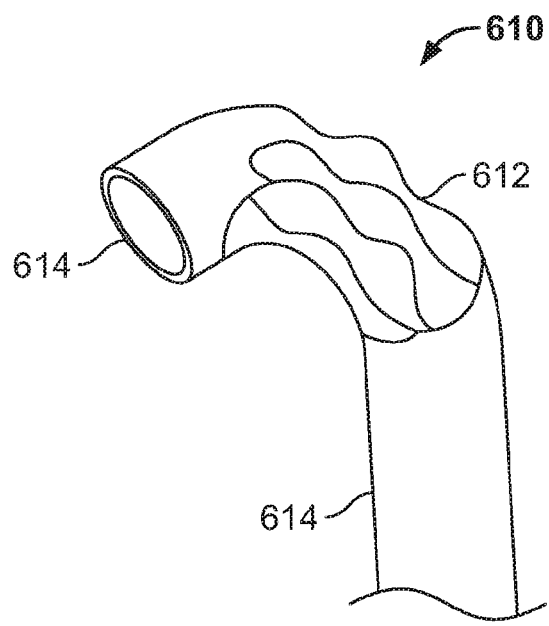

Reference is now made to FIGS. 14B, which is a schematic illustration of a curved member, generally referenced 610, constructed and operative with yet a further embodiment. Curved member 610 includes a shape memory portion 612 and a flexible portion 614. In the example set forth in FIG. 14B, flexible portion 614 is in the shape of a tube, and shape memory portion 612 is in the shape of a closed shape cut pattern having a curved shape memory.

Figure 14C:
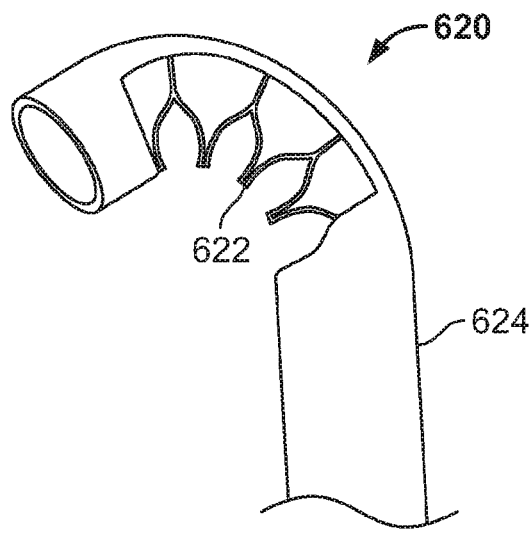

Reference is now made to FIGS. 14C, which is a schematic illustration of a curved member, generally referenced 620, constructed and operative with yet another embodiment. Curved member 620 includes a shape memory portion 622 and a flexible portion 624. In the example set forth in FIG. 14C, flexible portion 624 is in the shape a tube having a strip-shaped cut pattern, and shape memory portion 622 is in the form of a strip-shaped wire mesh completing the tube shape of (i.e., filling the cut pattern of) flexible portion 614.

Figure 14D:
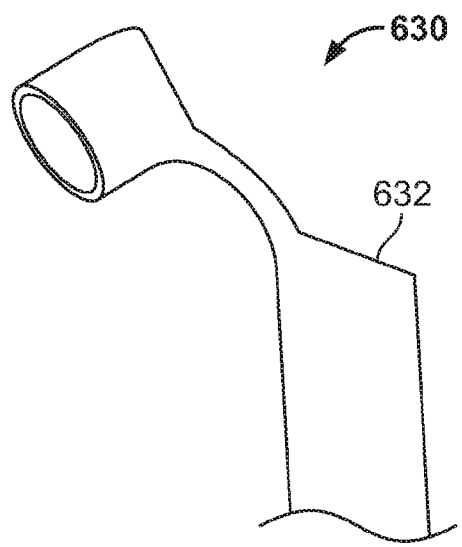

Reference is now made to FIGS. 14D, which is a schematic illustration of a curved member, generally referenced 630, constructed and operative with yet a further embodiment. Curved member 630 is made of a shape memory material and is in the form of an incomplete tube.

Figure 15:
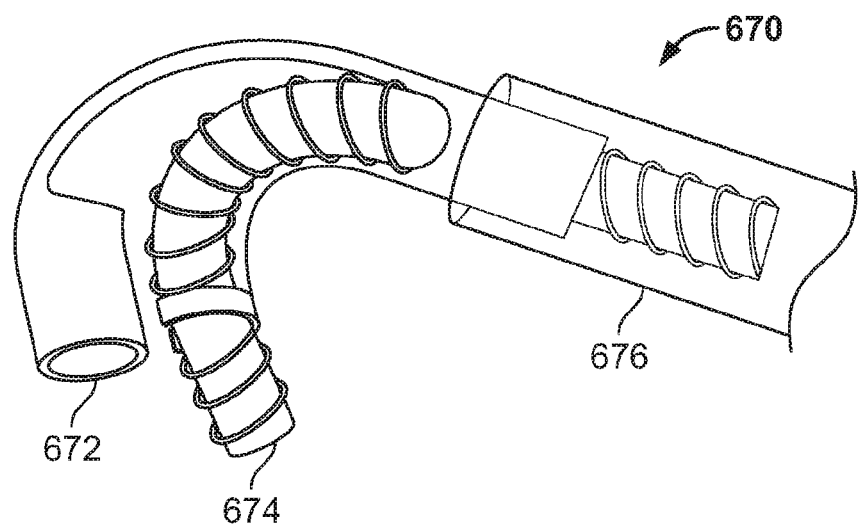
FIG. 15 is a side view of a split working tool, according to one embodiment.

Reference is now made to FIG. 15, which is a schematic illustration of a split working tool, generally referenced 670, constructed and operative with yet another embodiment. Split tool 670 is inserted into the sinus of a patient by employing an access system (e.g., system 250 of FIG. 4A-4D) via lumen 676 of the access system (i.e., lumen 676 defines a work channel of the access system). Split tool includes a bifurcated distal head tool 672 and a bifurcated proximal tool 674. Distal head tool 672 occupies the distal end of split tool 670 and is substantially short (e.g., a camera, a laser source and the like). Proximal tool is positioned proximally to distal head tool 672 (i.e., concentric with distal head tool 672) and can either be short or elongated (e.g., an irrigation or drainage catheter). When split tool 670 extends distally to lumen 676, split tool 670 splits such that both distal head tool 672 and proximal tool 674 are parallel to each other.

Figure 16A:
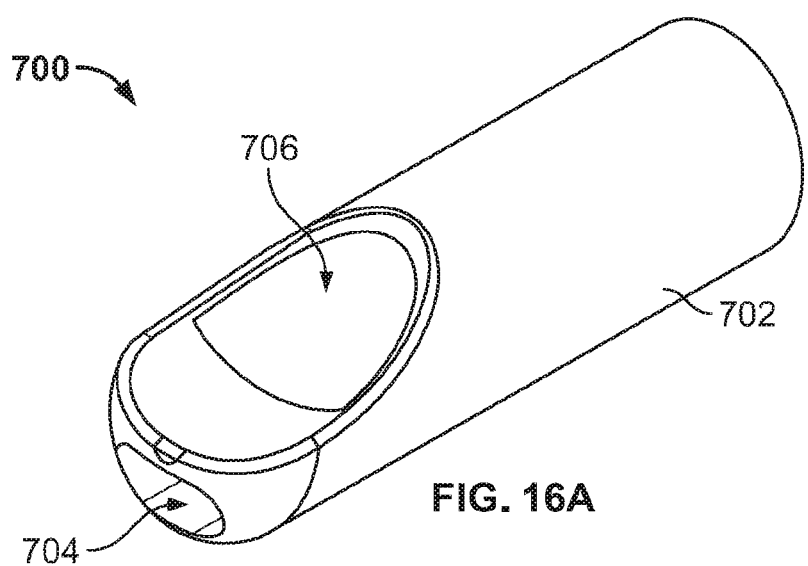
FIGS. 16A and 16B are perspective and front views, respectively, of a distal end of a rigid member, according to one embodiment.
Figure 16B:
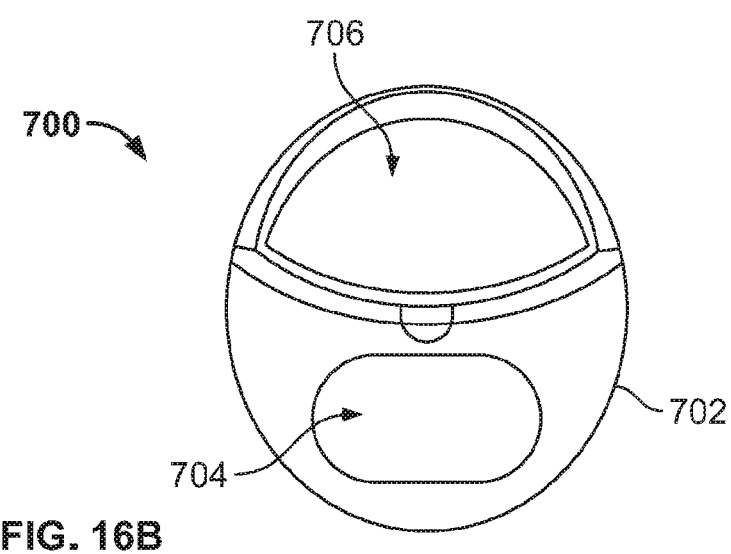

Reference is now made to FIGS. 16A and 16B, which are detail schematic illustrations of distal end 702 of a rigid member, generally referenced 700, constructed and operative with yet a further embodiment. FIG. 16A depicts the distal end of rigid member 700 from an isometric perspective. FIG. 16B depicts the distal end of rigid member 700 from a front view perspective. Rigid member 700 together with a flexible member and a curved member (both not shown) form together a sinus access system (not shown—e.g., access system 250 of FIG. 4A). Rigid member 700 includes a distal end 702, a curved member recess 704 and a work channel recess 706.

Distal end 702 (or at least its proximal side) of rigid member 700 has the same cross section as the rest of rigid member 700 such that rigid member 700 forms a continuous elongated body. As can be seen, for example, in FIGS. 16A and 16B, rigid member 700 and distal end 702 thereof are tube shaped defining a lumen (not referenced) running therethrough.

Curved member recess 704 is an opening at the distal end of rigid member enabling the curved member to pass therethrough. The cross section of curved member recess 704 snugly matches the cross section of the curved member. In the example set forth in FIGS. 16A and 16B, the cross section shape of curved member recess 704 (and of the curved member itself) is rectangular bar shaped having rounded corners.

The cross section of the curved member corresponds to that of curved member recess 704. In case the operator of the access system rotates any one of rigid member 700 or the curved member, the other one is rotated as well. That is, when a torsional force is applied to either one of rigid member 700 and the curved member, the supporter on which the torsional force is applied applies the same force on the other supporter via the snug coupling of the supporters. Thus, torsional deformation of the bar shaped curved member is prevented (or at least reduced).

As can be seen, in the example set forth in FIGS. 16A and 16B, curved member recess 704 is positioned off the central longitudinal axis of rigid member 700 (i.e., non-concentric). In other words, curved member recess 704 is located at the periphery of the cross section of distal end 702 of rigid member 704. As mentioned above (with reference to FIGS. 4B, 4E and FIG. 8), by being positioned off center, at the opposite direction from the bending direction of the access system (i.e., at the extrados), the curved path of the curved member has a larger radius of curvature than that of the longitudinal axis of the access system. Thereby, the strain applied onto curved member when extending beyond the length of rigid member 700 is reduced.

Work channel recess 706 is another opening at the distal end 702 of rigid member 700. Work channel recess 706, together with the lumen defined within rigid member 700, are part of the work channel of the access system, through which access is provided into and out of the sinus cavity.

For example, the work channel can provide access to a working tool, such as an optical sensor and an illumination fiber bundle, into the sinus cavity of the patient. The work channel can also enable fluids to be pumped into or out of the sinus cavity. The fluids go through the lumen of rigid member 700, along the curved member, and through work channel recess 706. Thus, the internal volume of rigid member 700 is used (i.e., for slidably passing the curved member, and for enabling a working tool or fluids, to pass therethrough), and thereby the dimensions of the access system can be reduced.

In this manner, fluids that pass through work channel recess 706 can then pass through the flexible member and exit from the access system into the sinus cavity through a port in the distal end of the flexible member. Thus, fluids can be passed from a container (i.e., located outside of the patient's body) into the target location at the sinus cavity (or from the target location to a container outside of the patient's body) through the access system while the access system is maintained in place. In other words, the operator does not have to insert and/or retract one or more supporters, tools or any other instruments into (or out of) the patient's body multiple times in order to pass the fluids.

In accordance with an alternative embodiment, rigid member 700 includes therewithin two separate channels (i.e., lumens). The first lumen enfolds the curved member of the access system, and ends at curved member recess 704. The second lumen defines the work channel and ends at work channel recess 706. In this manner, the curved member is separated from the working channel for preventing the working tool, or the fluids, passing through the work channel from coming into contact with the curved member.

Figure 17A:
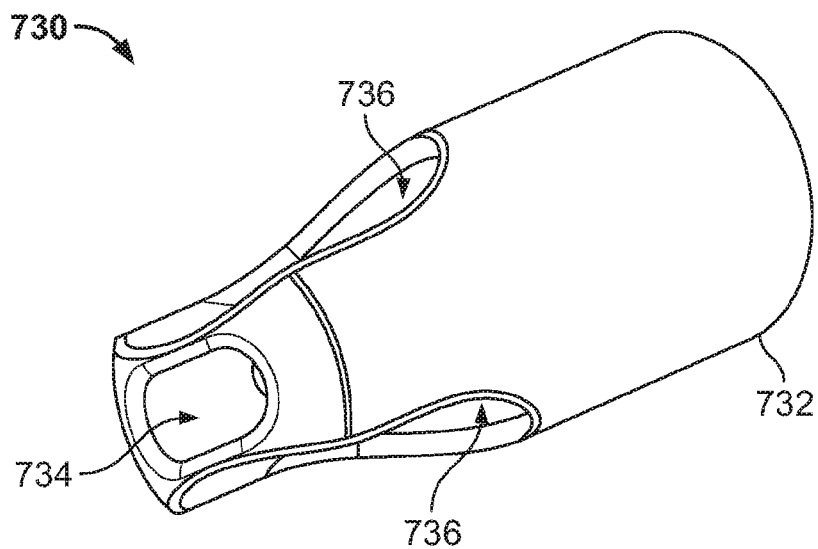
FIGS. 17A-17C are perspective, front and perspective views, respectively, of a distal end of a rigid member, according to another embodiment.
Figure 17B:
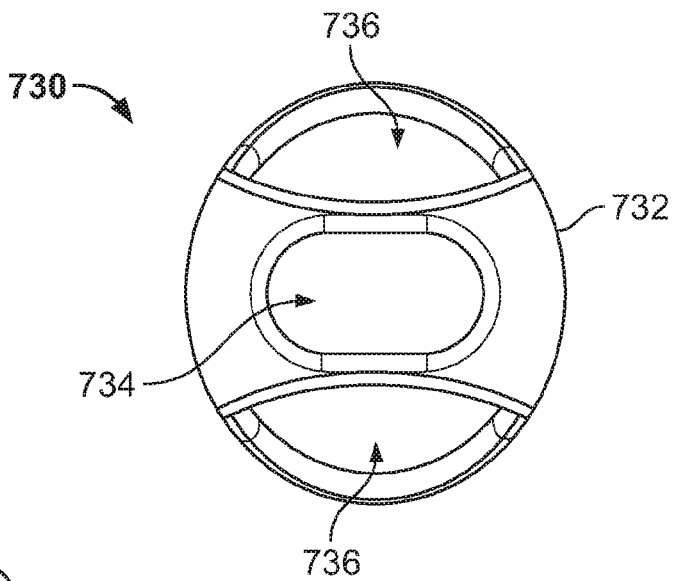
Figure 17C:
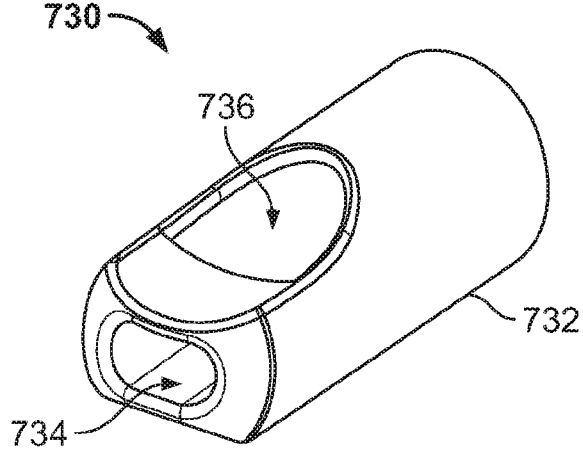

Reference is now made to FIGS. 17A, 17B and 17C, which are schematic illustrations of a distal end of a rigid member, generally referenced 730, constructed and operative with yet another embodiment. FIG. 17A depicts the distal end of rigid member 730 from a top view perspective. FIG. 17B depicts the distal end of rigid member 730 from a front view perspective. FIG. 17C depicts the distal end of rigid member 730 from an isometric perspective. Rigid member 730 together with a flexible member and a curved member (both not shown) form together a sinus access system (not shown—e.g., access system 250 of FIG. 4A). Rigid member 730 includes a distal end 732, a curved member recess 734 and two work channel recesses 736.

In a similar manner to distal end 702 of FIGS. 16A and 16B, distal end 732 (or at least its proximal side) of rigid member 730 has the same cross section as the rest of rigid member 730 such that rigid member 730 forms a continuous elongated body. As can be seen in FIGS. 17A-17C, rigid member 730 and distal end 732 thereof are tube shaped defining a lumen (not referenced) running therethrough. Curved member recess 734 is substantially similar to curved member recess 704 of FIGS. 16A and 16B in terms of functionality. It is noted however, that curved member recess 734 is concentric with rigid member 730 (i.e., is not located off-center).

In the example set forth in FIGS. 17A-17C, distal end 732 of rigid member 730 includes two work channel recesses 736 positioned at opposite sides of distal end 732. Each of the work channel recesses 736 enables passage of a different working tool. For example, one work channel recess 736 enables a camera to pass through the access system, and the other work channel recess 736 enables an illumination fiber bundle to pass through the access system.

Each of the work channel recesses 736 can also enable fluids to be pumped into or out of the sinus cavity. The fluids go through the lumen of rigid member 730, along the curved member, and through the work channel recesses 736. Thus, similarly to the internal volume of rigid member 700 depicted in FIGS. 16A-16B, the internal volume of rigid member 730 is used (i.e., for slidably passing the curved member, and for enabling a working tool or fluids, to pass therethrough), and thereby the dimensions of the access system can be reduced. In this manner, fluids that pass through the work channel recesses 736 can then pass through the flexible member and exit from the access system into the sinus cavity through a port in the distal end of the flexible member. Thus, fluids can be passed from a container (i.e., located outside of the patient's body) into the target location at the sinus cavity (or sucked from the target location to a container outside of the patient's body) through the access system while the access system is maintained in place. In other words, the operator does not have to insert or retract one or more supporters, tools or any other instruments to or from the patient's body multiple times in order to pass fluids thereto and/or therefrom.

As mentioned above, in some embodiments of the invention the flexible member enfolds (surrounds) the other supporters of the access system. The weak distal end of the flexible member can also be coupled with (or include) a functional distal head similar in structure and functionality to those described hereinabove with reference to FIGS. 16A-B and 17A-C. Furthermore, the functional distal head described in conjunction with FIG. 5 can also be structurally and functionally similar to the functional distal heads of FIGS. 16A-B and 17A-C.

Reference is now made to FIGS. 18A and 18B, which are detail schematic illustrations of a distal end of a rigid member, generally referenced 760, constructed and operative with yet a further embodiment. FIG. 18A depicts the distal end of rigid member 760 from an isometric perspective. FIG. 18B depicts the distal end of rigid member 760 from a front view perspective. Rigid member 760 together with a flexible member and a curved member (both not shown) form together a sinus access system (not shown—e.g., access system 250 of FIG. 4A). Rigid member 760 includes a distal end 762, a curved member recess 764 and a plurality of radial protrusions 766.

Radial protrusions 766 extend radially from the external surface of rigid member 760. The flexible member (not shown) slidably enfolds rigid member 760 and slides along radial protrusions 766. In this manner, an inner volume (i.e., intra-supporter volume) is formed between the internal surface of the flexible member and the external surface of rigid member 760. In other words, in case for example the flexible member is in form of a coil, it enfolds (i.e., and hugs) the rigid member and the radial protrusions, thereby an intra-volume is formed between the flexible member and the rigid member. The size of the intra-supporter volume is determined by the height (i.e., the length of the radial extension of the protrusions) of the radial protrusions.

The formed intra-supporter volume can be employed as a work channel or for enabling passage for fluids, into and out of, the sinus cavity. In the example, set forth in FIGS. 18A and 18B, the radial protrusion are fin shaped. Alternatively, any radial protruding element can function as the radial protrusions 766. The radial protrusions 766 can be elongated and run along the length of the rigid member 760, or can be short, as seen in FIG. 18A. The access system can include several sets of radial protrusions supporting the flexible member that enfolds the rigid member along the length of the rigid member.

In this manner, fluids that pass through the intra-supporter volume can then further pass through the flexible member (i.e., beyond rigid member 760) and exit from the access system into the sinus cavity through a port in the distal end of the flexible member. Thus, fluids can be passed from a container (i.e., located outside of the patient's body) into the target location at the sinus cavity (or from the target location to a container outside of the patient's body) through the access system while the access system is maintained in place. In other words, the operator does not have to insert and/or retract one or more supporters, tools or any other instruments to and/or from the patient's body multiple times in order to pass fluids thereto and/or therefrom.

As described herein above, according to some embodiments, the access system includes three supporters that form together a tortuous path (e.g., curved path), enabling the access system to access the sinus cavity of the patient. All supporters are advanced together until a first desired location, at which the access system should curve around anatomical obstacles for reaching the sinus. At the first desired location, the rigid member is stopped, and the curved and flexible members are advanced further. When the curved member extends beyond the rigid member it regains its original curved shape, thereby producing the curved path of the access system. The radius of curvature of the path of the curved member might be different than that of the flexible member. Therefore, the length of the path followed by each supporter (i.e., curved and weak) is different for completing the same curved angle. For example, due to different diameters of the supporters, or because of the different locations of the supporters within the access system (e.g., the curved member is at the extrados of the bend and the flexible member is at the intrados). This can be analogized to athletes running around a circular (or oval) ring. An athlete running at the inner lane covers less distance than an athlete running at the outer lane.

In case the operator advances the curved member and the flexible member the same distance together (e.g., by pushing only one of the supporters), a compensating element can be coupled between the supporters for coordinating their advancement along the curved path, such that both supporters complete the same curve angle together. Reference is now made to FIG. 19, which is a schematic illustration of an access system, generally referenced 800, constructed and operative with yet another embodiment. Access system 800 includes a rigid member 802, a curved member 804, a flexible member 806, a housing 808, a compensating element 810, and a curved member coupler 812. Rigid member 802, curved member 804 and flexible member 806 are slidably coupled with each other. In a folded configuration of access system 800, housing 808 houses (at least in part) supporters 802, 804 and optionally 806. Supporters 802, 804 and 806 can extend distally out of housing 808 when inserted into the body of the patient. Compensating element 810 is coupled between curved member 804 and flexible member 806. In the example set forth in FIG. 19, one end of compensating element 810 is coupled with flexible member 806, and the opposite end of compensating element 810 is coupled with curved member 804, via curved member coupler 812.

Compensating element 810 can be for example, a coil, a biasing spring, or a stretchable wire. Alternatively, the compensating element can be formed from other components and elements for coordinating the movement of the curved member and the flexible member across the curved path (e.g., gears). Alternatively, the compensating element can be accommodated in the housing 808. In the example set forth in FIG. 19, compensating element 810 is a spring (i.e., compensating spring 810). Compensating spring 810 enables simultaneous and coordinated movement of both curved member 804 and flexible member 806.

Initially, when all supporters are overlapped (i.e., in a straight position), compensating spring 810 is loaded (i.e., preloaded). As curved member 804 advances distally, compensating spring 810 becomes unloaded, enabling the simultaneous and coordinated movement of the two supporters (i.e., curved and weak). As mentioned above, when both curved member 804 and flexible member 806 are pushed together, each follows a different path and therefore, covers a different distance (i.e., for the same curve angle). Thereby, by pushing both supporters, one would advance further than the other. Compensating spring 810 compensates for the different paths followed by the supporters and enables both supporters to be advanced in a coordinated fashion. In summation, the function of the compensating element can be analogized to the function of a car differential that coordinates the rotations of the wheels during turns, thereby compensating for the different distances covered by the wheels during turns.

When the operator completes the curving of the access system, and wishes to advance the flexible member beyond the curved member, the operator employs a release mechanism (not shown) for releasing compensating spring 810 from at least one of the supporters, thereby enabling advancement of only the flexible member. The release mechanism can be formed of components, such as wires, piezoelectric elements, and the like.

With reference to FIGS. 20-35, various embodiments of a modular access device, system and method are described below. The embodiments generally include a handle and a sinus access member (which may also be called a "steerable work tool positioning member" or simply an "access member"). The described embodiments may be used for providing access to, and in some cases guiding one or more work tools to, a treatment area in a human or animal body. As mentioned above, the clinical example used in describing FIGS. 20-35 will be accessing and guiding work tools to a paranasal sinus, but this is only one example and is not intending to be limiting. The system, device and method embodiments described below generally include a rigid straight member, a curved shape memory member that is less rigid than the rigid straight member, and a flexible straight member that is less rigid than the curved member. At least two of these three members are slidably coupled to the other members, so that by advancing and retracting relative to one another they allow the access device to steer through tight anatomical passageways and thus treat difficult to access cavities and other treatment areas. Again, the example used below is navigation through the nasal cavity to access the paranasal sinuses for treatment of the sinuses. The embodiments described below may use any one or more of the embodiments and/or features described above for providing articulation/steering of a device or the like.

Figure 20:
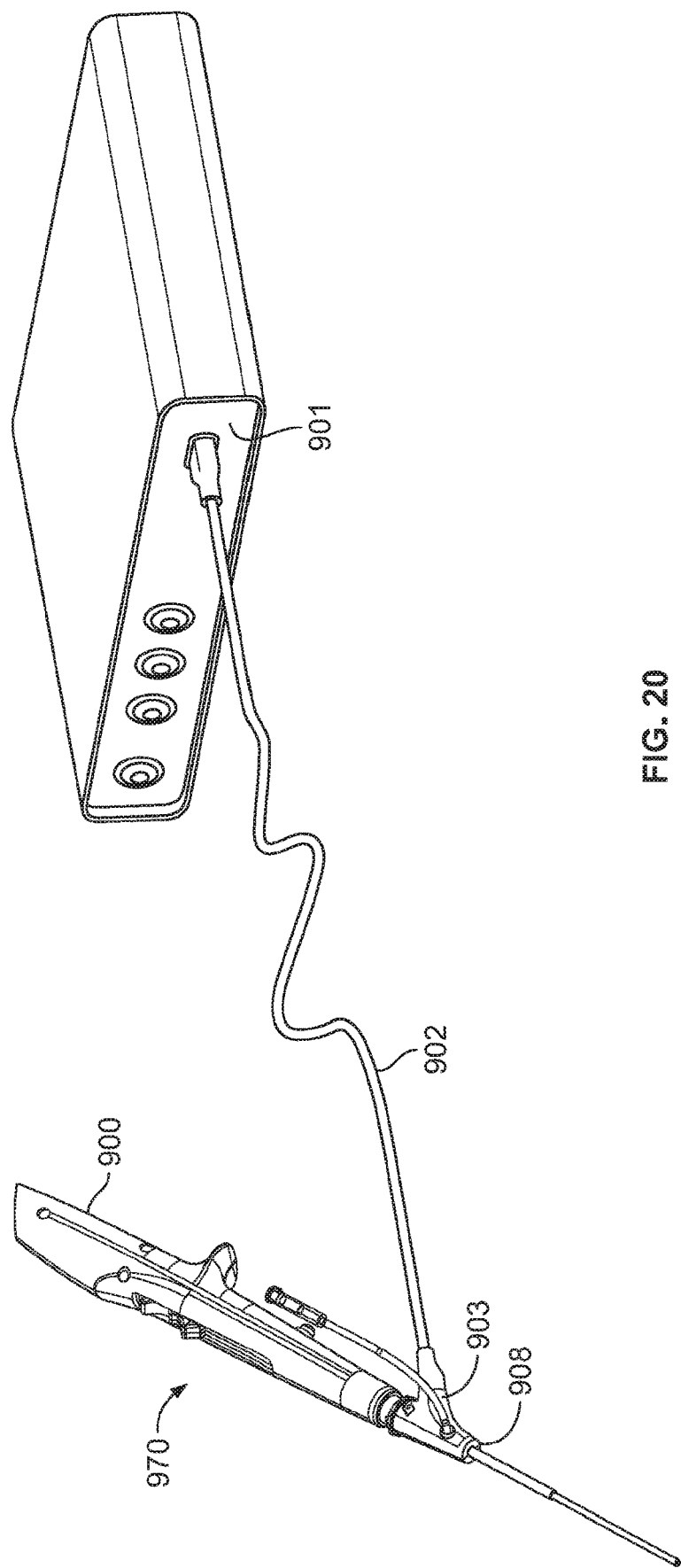
FIG. 20 is a perspective view of a modular cavity access system, according to one embodiment.
Figure 21A:
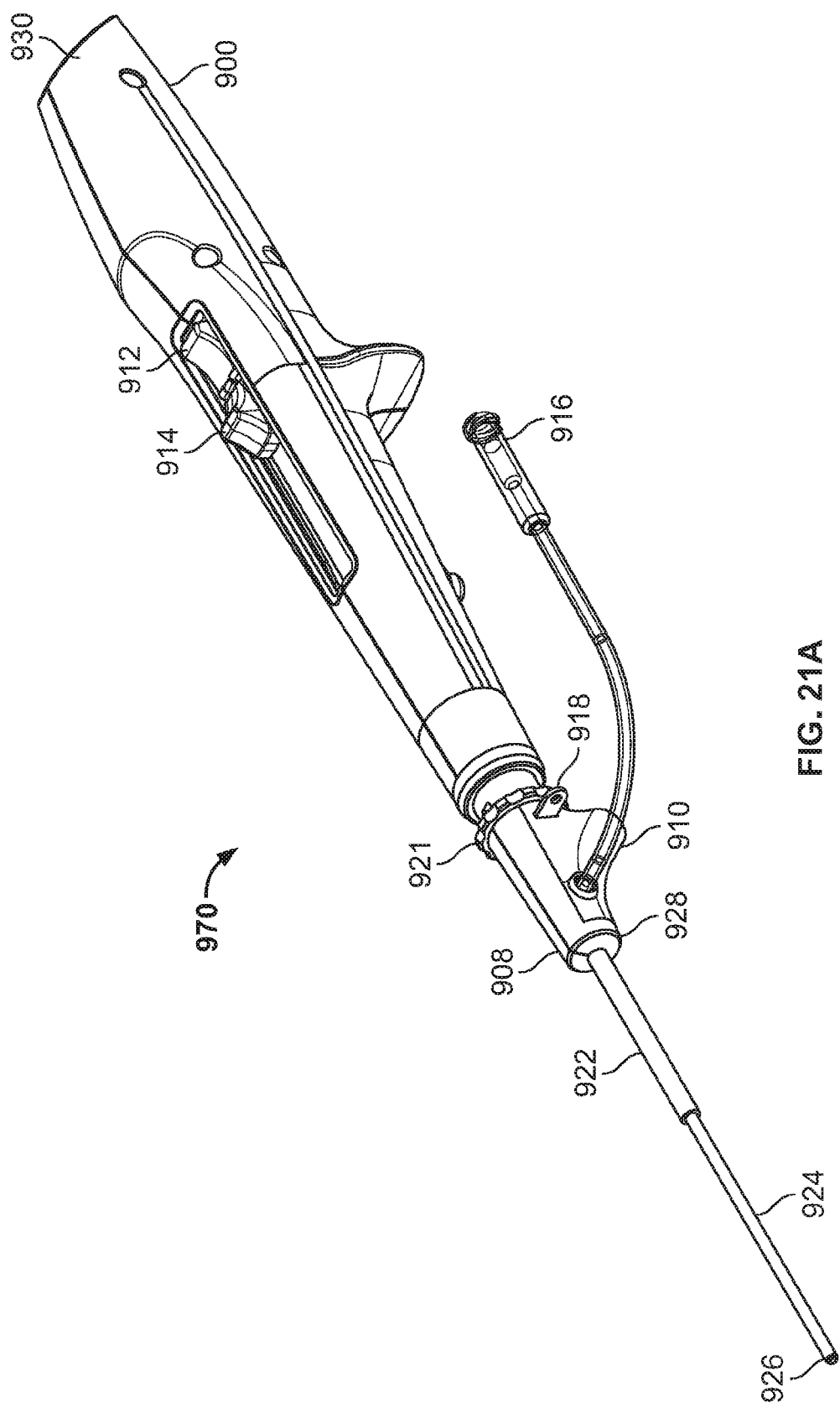
FIG. 21A is a perspective view of the access device portion of the access system of FIG. 20, including a control handle and a mechanically steerable worktool positioning member, according to one embodiment.
Figure 21B:
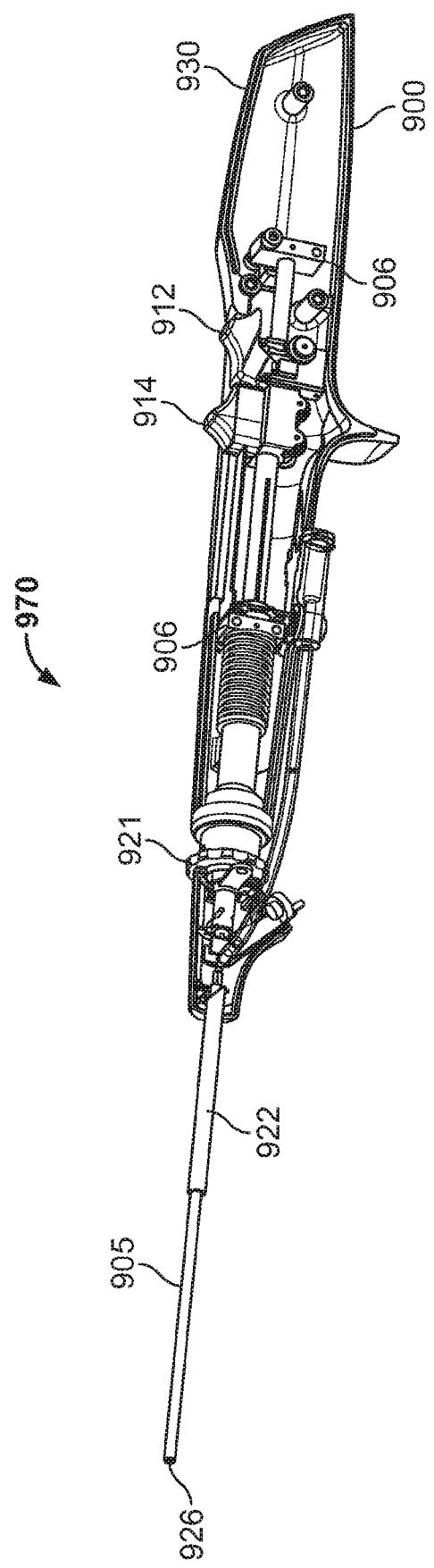
FIG. 21B is a side view of the access device of FIG. 21A, with half of the handle removed to show the inside of the handle.
Figure 22A:
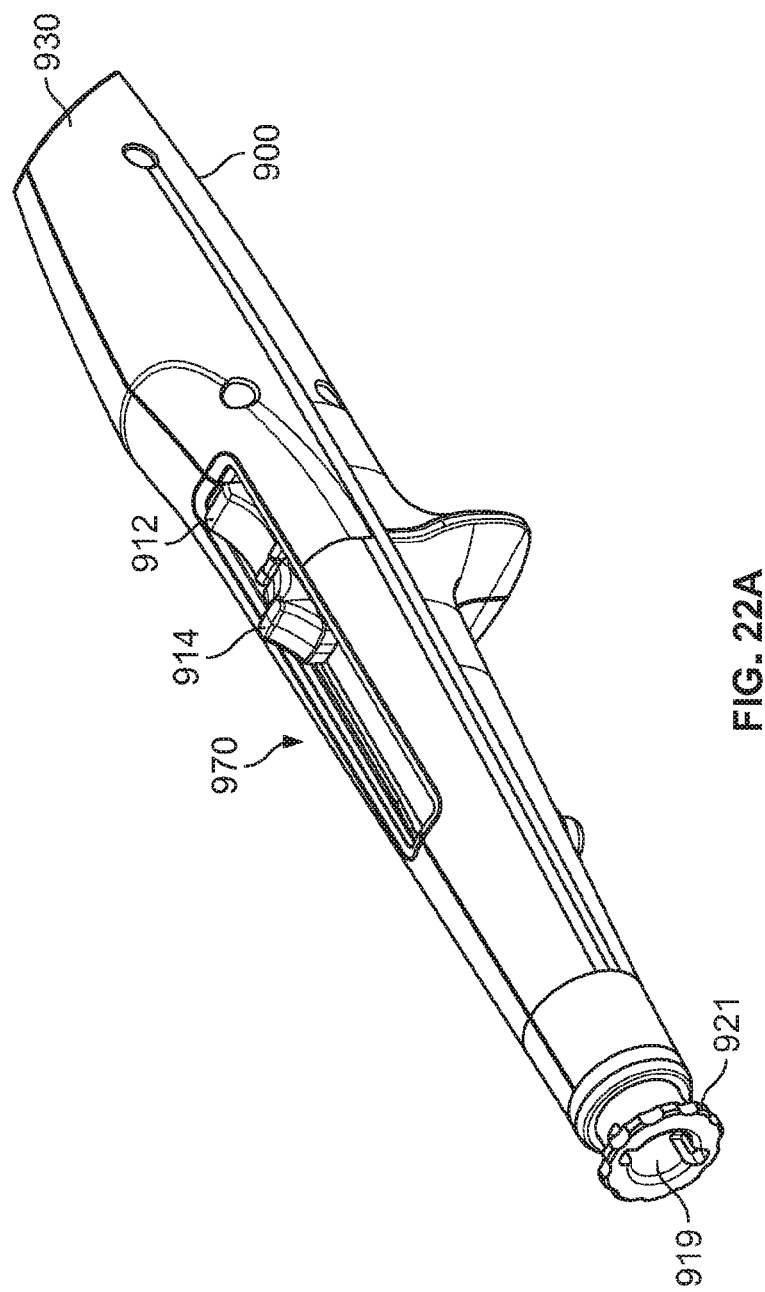
FIG. 22A is a perspective view of the handle of the access device of FIGS. 21A and 21B.
Figure 22B:
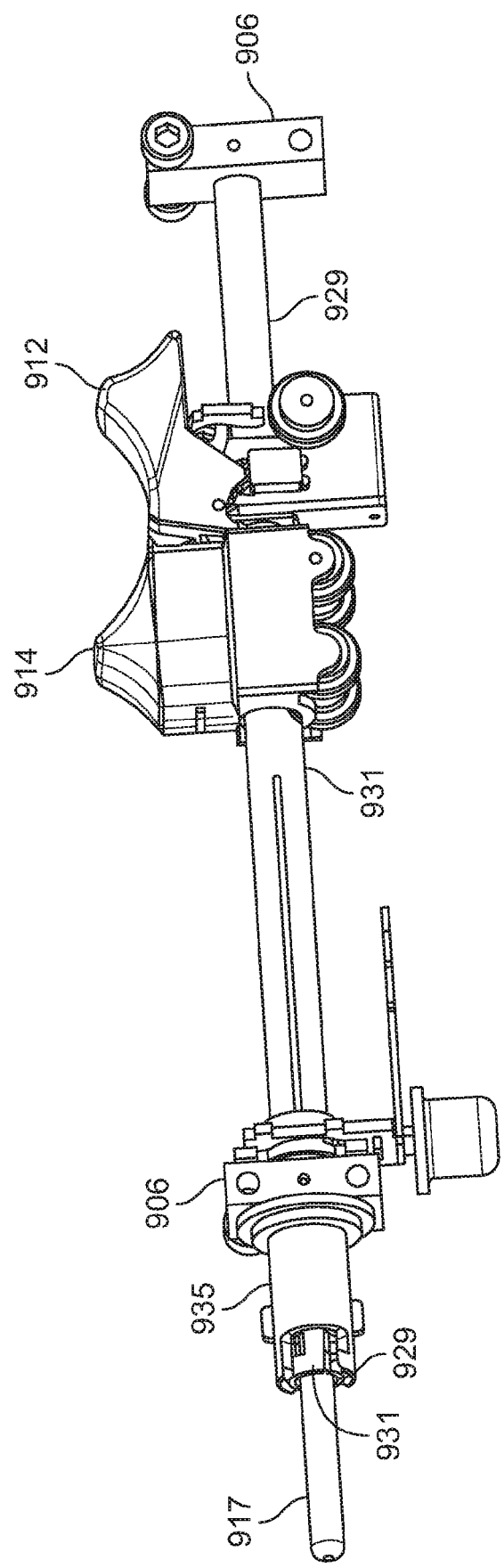
FIG. 22B is a perspective view of a component of the handle of FIG. 22A.
Figure 23A:
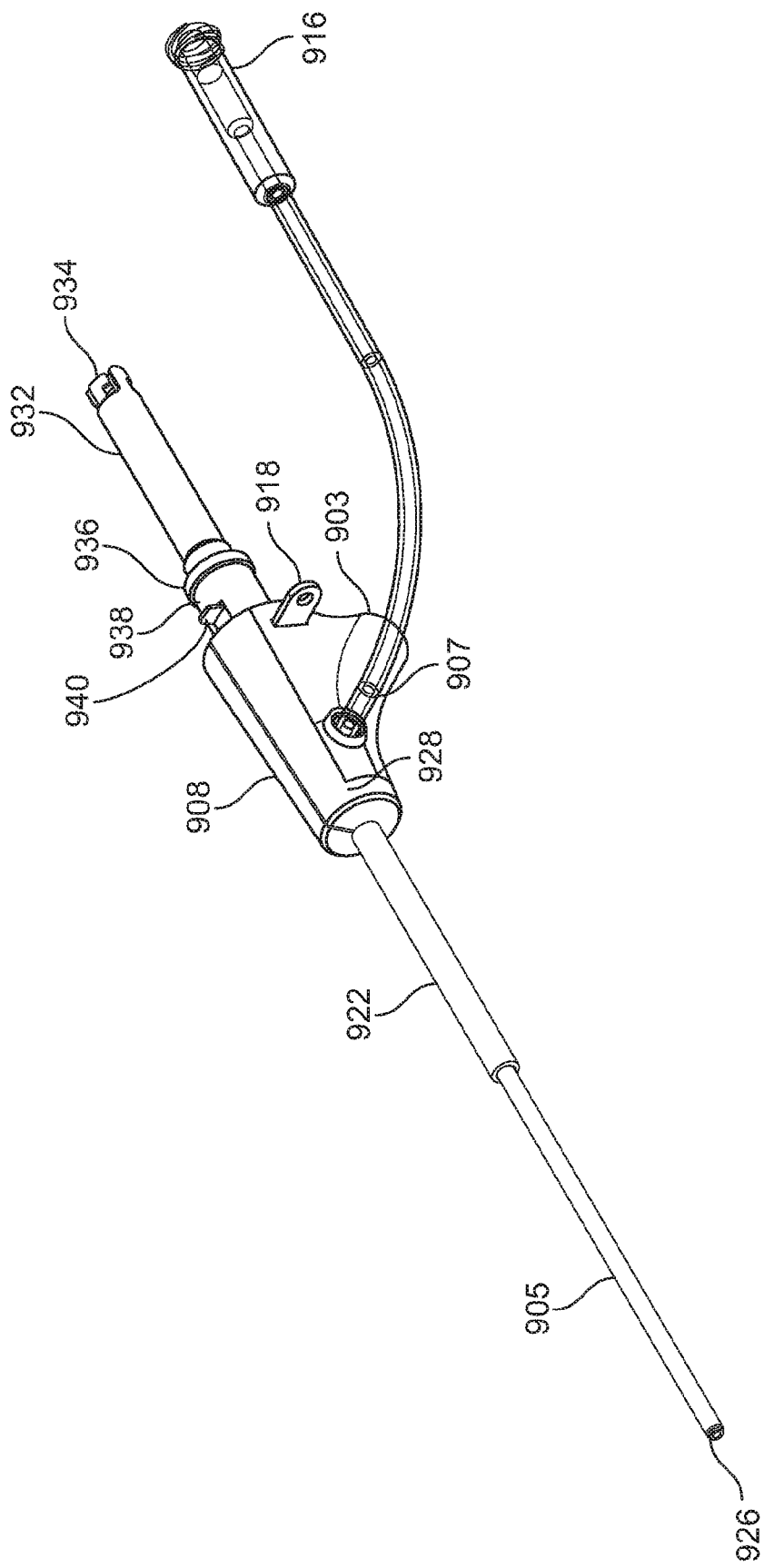
FIG. 23A is a perspective view of the steerable worktool positioning member of FIGS. 21A and 21B, which is attachable to the handle of FIG. 22A.
Figure 24A:
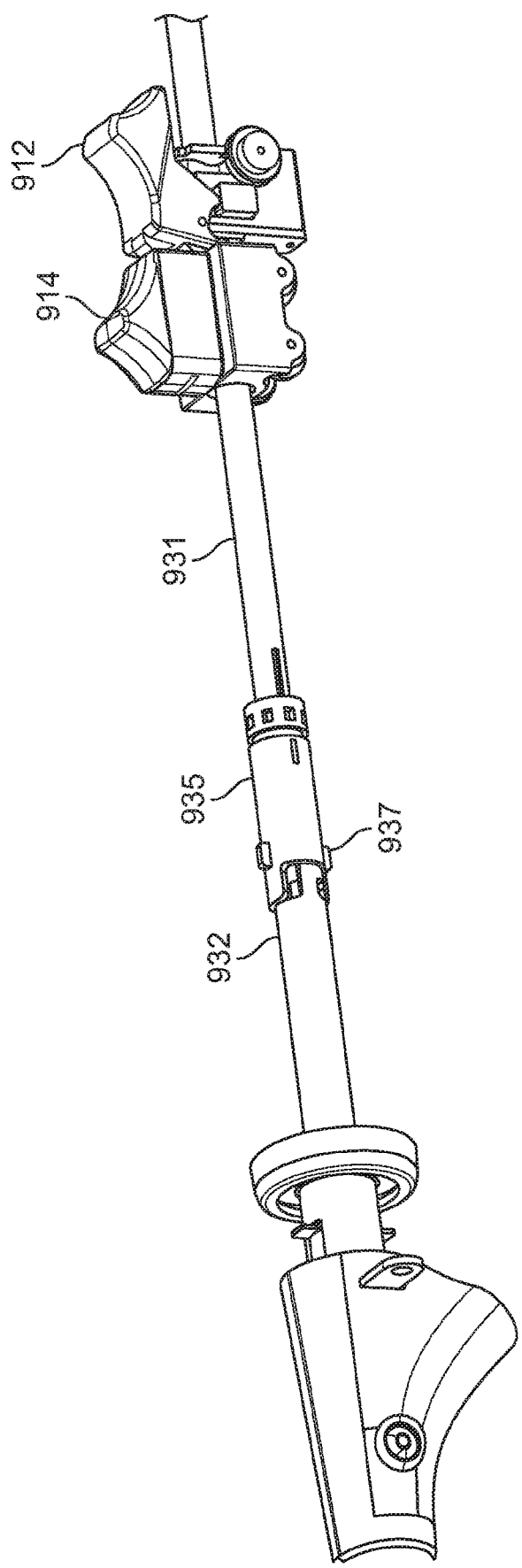
Figure 24D:
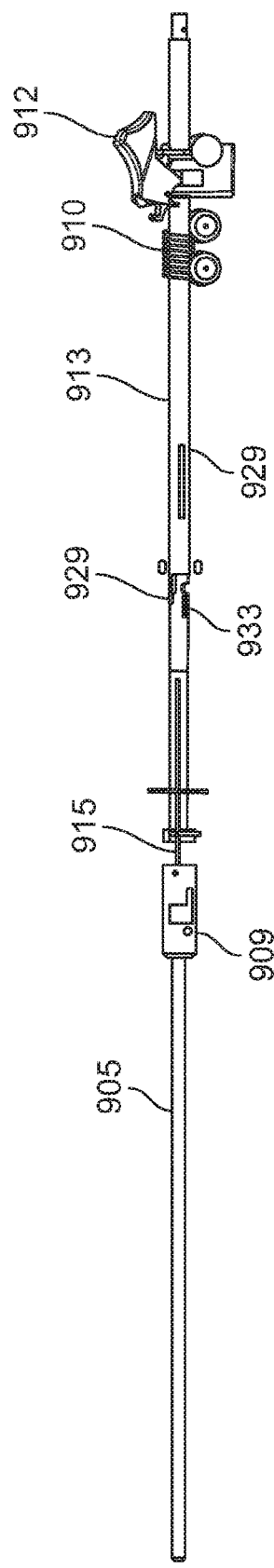
Figure 24E:
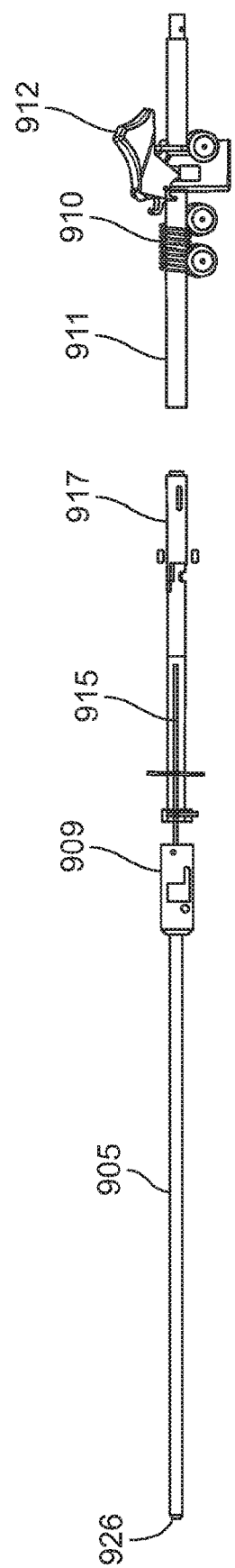

Referring to FIG. 20, a modular body cavity access system 970 is illustrated, connected to a camera control unit 901. In some embodiments, access system 970 may also include control unit 901 or another embodiment of a control unit, but for the purposes of simplicity, access system 970 will generally be described herein as not including camera control unit 901. The illustrated embodiment of access system 970 is for accessing human paranasal sinuses, but as mentioned previously, access system 970 may be used or modified for use in other parts of the body and for other purposes. In general, access system 970 includes a handle 900 at its proximal end and a steerable paranasal sinus access member 908 at its distal end. System 970 may optionally be wirelessly or physically connected to camera control unit 901 via a power and data cable 902 to a power-data port 903, which may be part of sinus access member 908. In one embodiment, the distal end of handle 900 is removably connected to sinus access member 908. In such an embodiment, handle 900 may be reusable, and sinus access member 908 may be disposable. This two-part embodiment of access system 970 may be referred to as "modular," in that it includes a handle "module" and a working end or sinus access end "module." In alternative embodiments, handle 900 and sinus access member 908 may be permanently attached.

Referring to FIGS. 21a, 21b, 22a, and 22b, the handle 900 of the access system 970 is described in more detail. In this embodiment, handle 900 includes a handgrip housing 930 (or simply "a housing"), a curving actuator 912 and a worktool extension actuator 914. The curving actuator slides back and forth, relative to housing 930, to advance and retract the curved shape memory member (for example, a terminal section of nitinol 927 attached to the distal end of curving member extension rod 915) and thus adjust the overlap of the curved shape memory member 927 and a rigid member 920 (or "relatively stiffer straight structural support," see FIG. 23C), to allow for curving and straightening of the distal end of the access system 970. The extension actuator 914 acts through B-connector 931 to advance and retract a flexible extension tube 923 (or "flexible straight member" or "flexible tube") beyond the curved shape memory member 927 and/or beyond the rigid member 920. The rigid member 920 is, in some embodiments, fixedly attached to the housing 930, so that it does not move. The curved member 927 and the flexible member 923 slide longitudinally relative to one another and relative to the rigid member 920, to provide curving and extension of the access system 970, thus providing steering. In some embodiments, the curving actuator 912 and the extension actuator 914 may be combined into one sliding button (or "sliding actuator") or attached together. In one embodiment, the curving actuator 912 function may be actuated by pressing down on the one sliding button and advancing or retracting it, while the extension actuator 914 function may be actuated by sliding the one sliding button without pressing down on it. An alternative embodiment may include the opposite pressing/sliding configuration.

In this description, the curved member 927 is generally referred to with the number label 927, although the term "curved member 927" generally refers to the entire part that includes the distal curved portion 927 and the proximal straight portion or "rod" 915. Similarly, the term and number label "flexible member 923" is used to refer to the entire part that includes the proximal portion 923 and the distal spring portion 924. This terminology is used to simplify the description, so that the curved member 927 and the flexible member 923 can be referred to as one part apiece, rather than describing their multiple portions or parts at each mention.

Handle 900 may also include a rotational indexing mechanism 921 for synchronously, controllably rotating all of the slidably-coupled and extendible structural support members in unison in sinus access member 908 around the longitudinal axis, either in small, controlled increments or continuously. Handle 900 may also include a spring-loaded sinus access member port 919 for detachably receiving and engaging a substantially cylindrical and concentrically arranged D-connector 932, C-connector 934 and worktool inner connector 933 of sinus access member 908, whereby the distal spring portion 924 of flexible member 923 and the distal portion of curved member 927 that has been received in and engaged with port 919 are independently steerable and independently extendable beyond the curvature point by actuating curving actuator 912 and extension actuator 914.

Figure 25A:
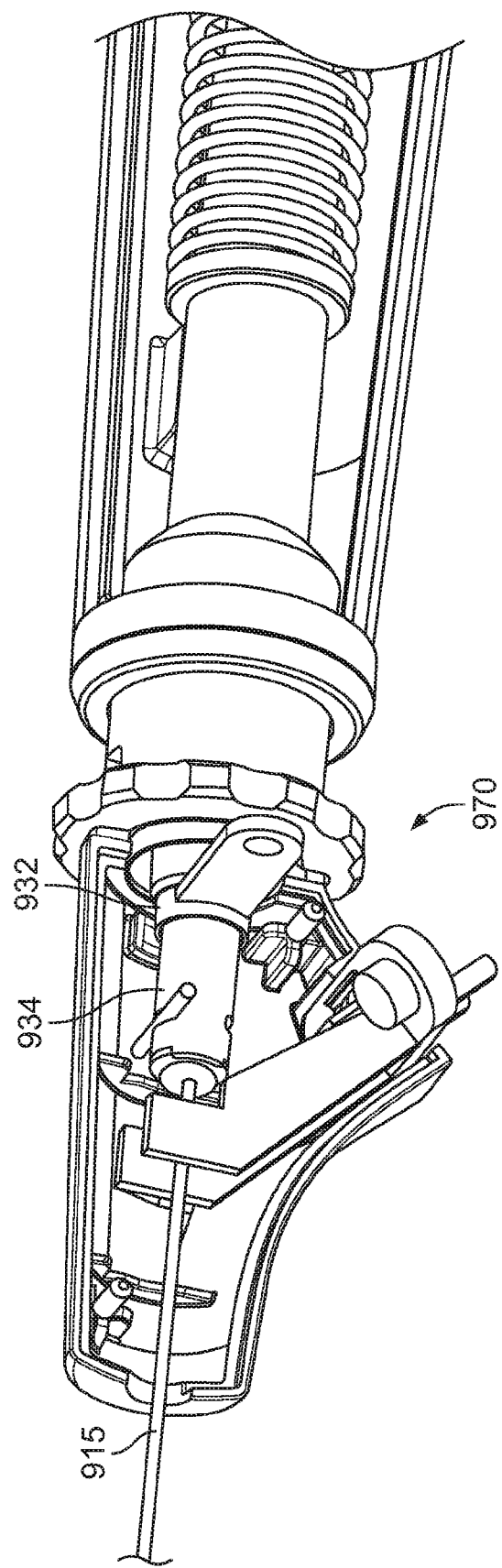
FIGS. 25A and 25B are perspective views of a portion of the access device of FIGS. 20-24G, with a portion of the handle removed to show internal components.
Figure 25B:
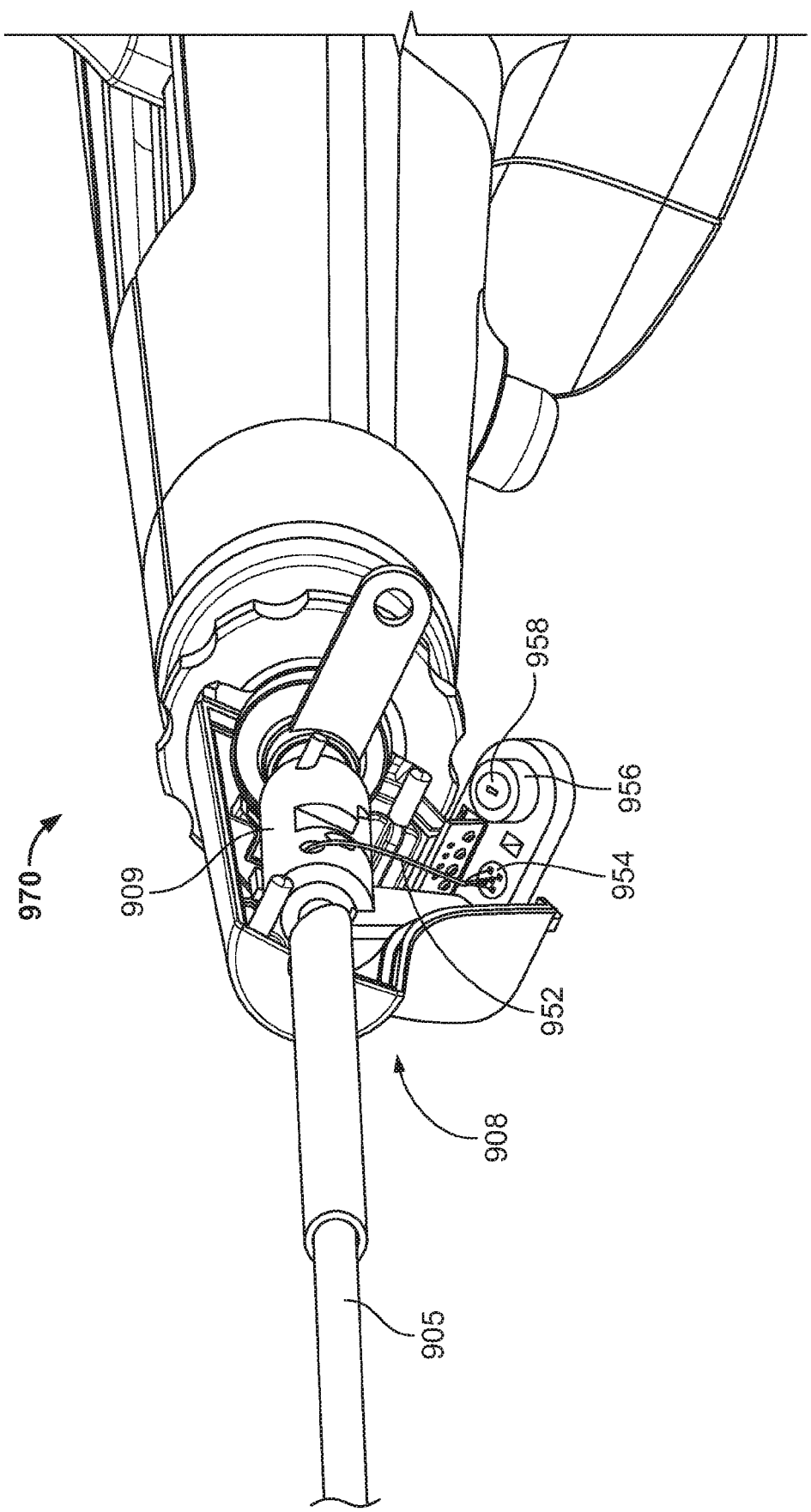
Figure 26:
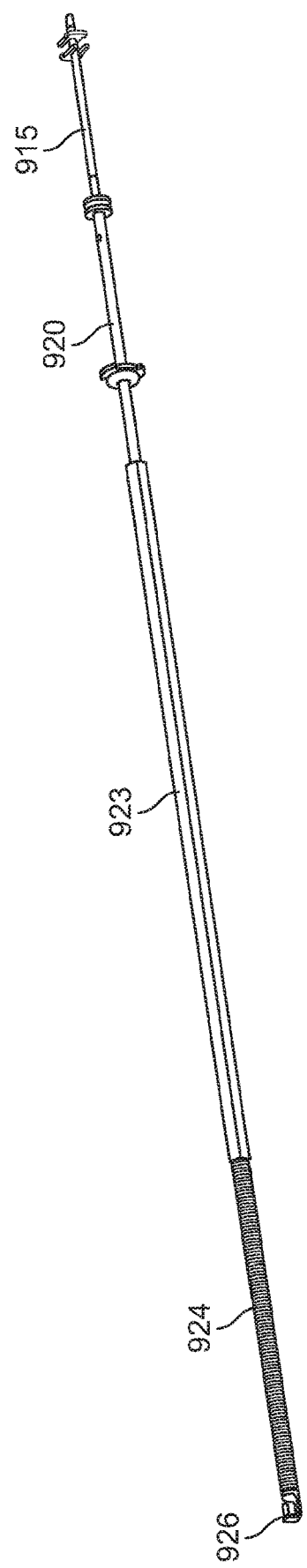
FIG. 26 is a perspective view of a distal portion of the support members of the access device of FIGS. 20-25.
Figure 27:
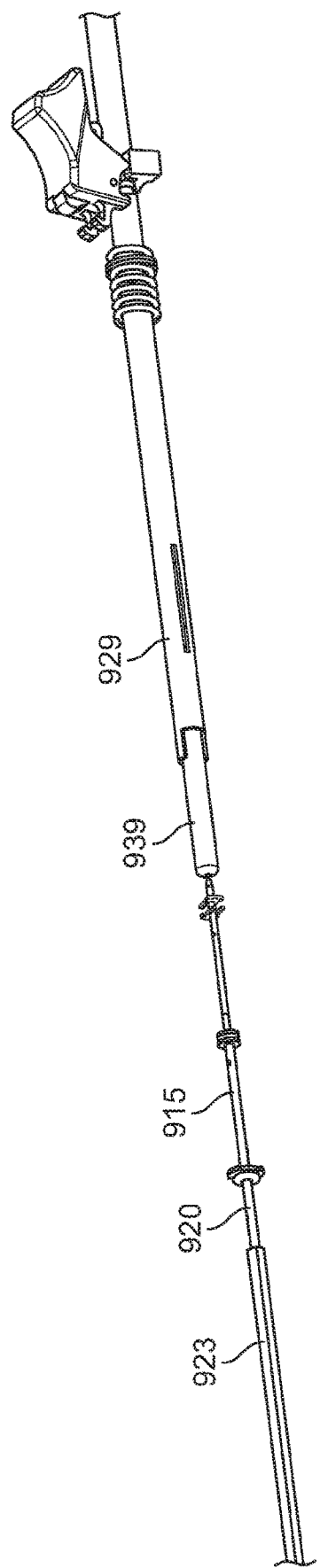
FIG. 27 is a perspective view of a distal portion of the support members of the access device of FIGS. 20-26.
Figure 29:
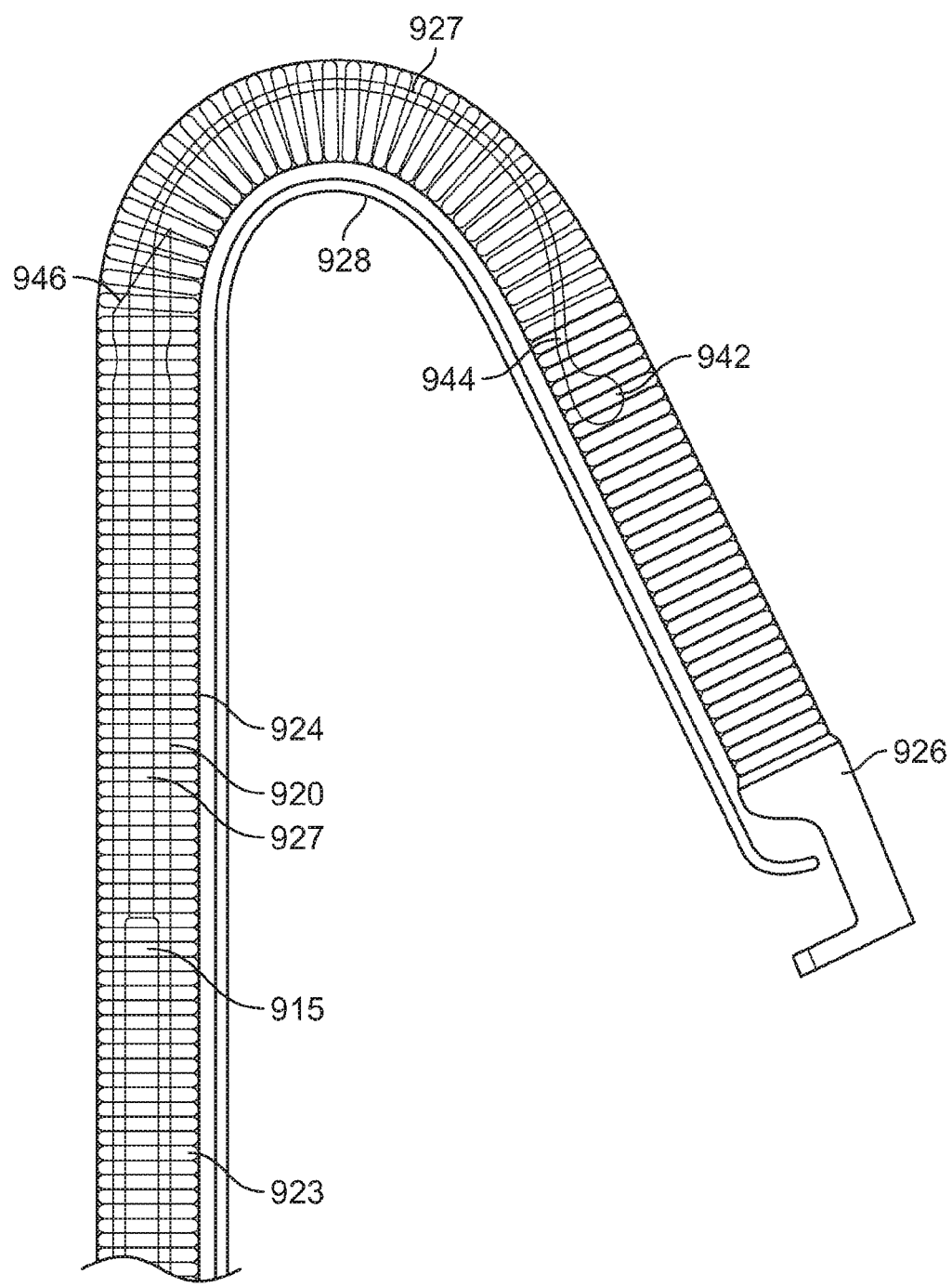
FIG. 29 is a side view of a distal portion of a worktool positioning member, according to one embodiment.
Figure 30C:
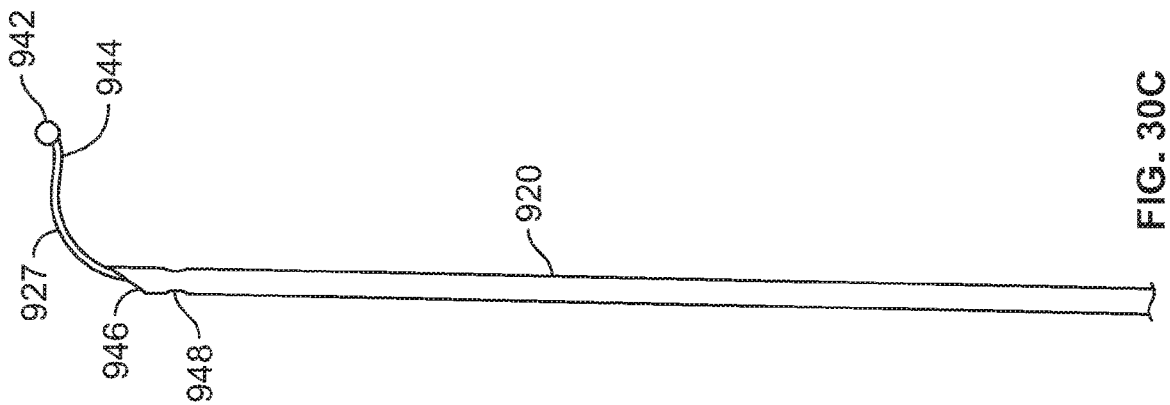
FIGS. 30A-30F are side views of a worktool positioning member, illustrated in a sequence showing the changing curve of a shape memory portion as it moves from a fully extended position (FIG. 30A) to a fully retracted position (FIG. 30F)
Figure 30B:
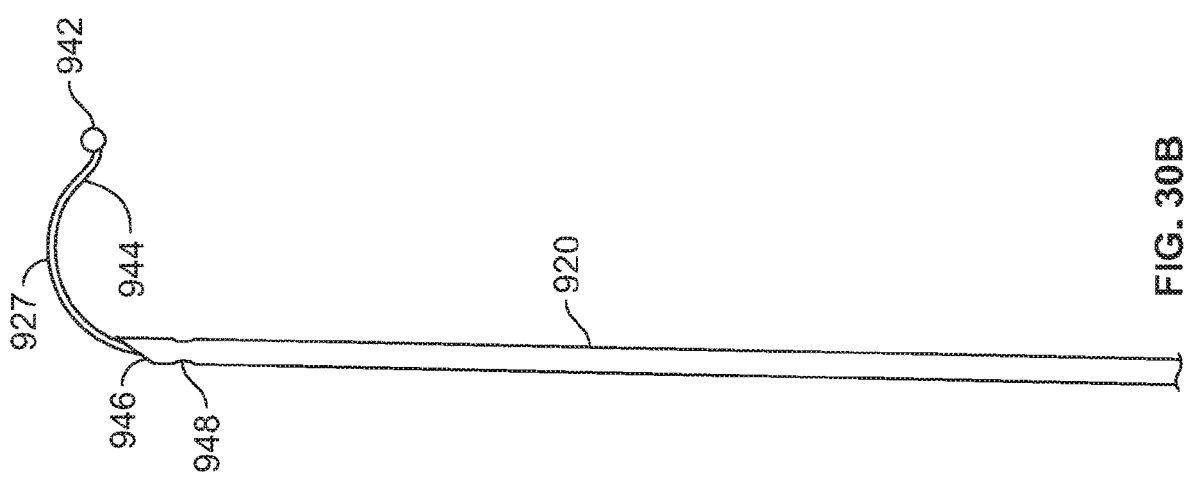
Figure 30A:
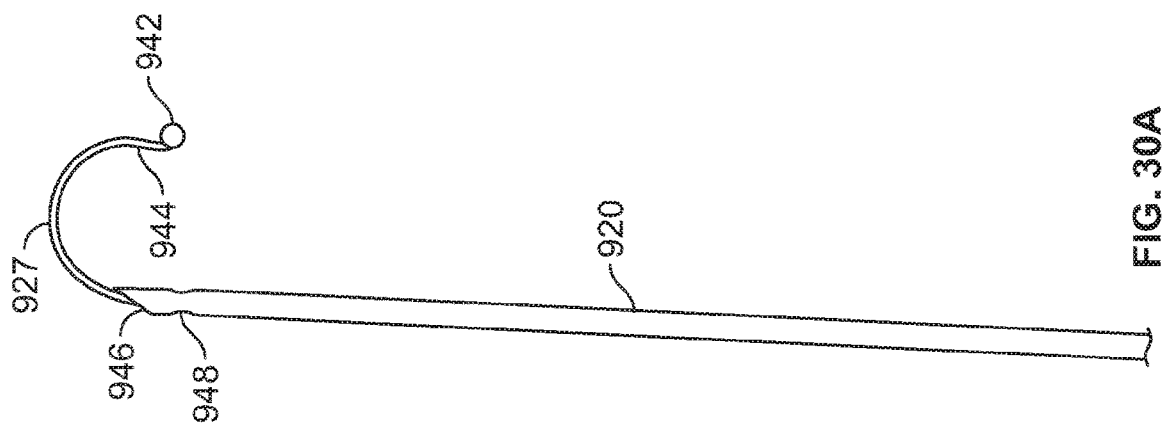
Figure 30F:
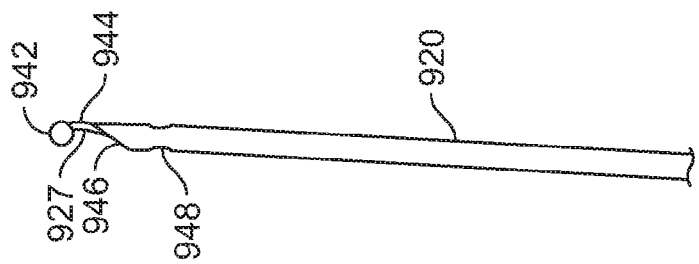
Figure 30E:
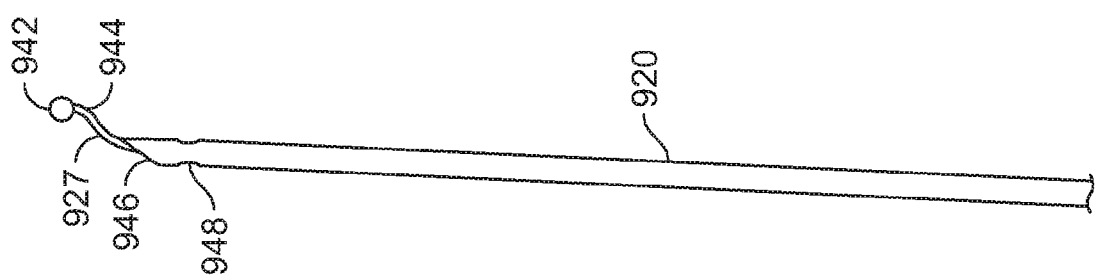
Figure 30D:
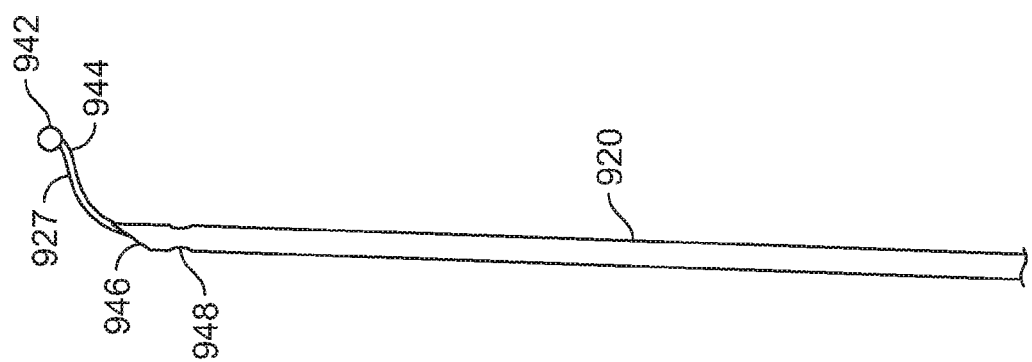
Figure 31F:
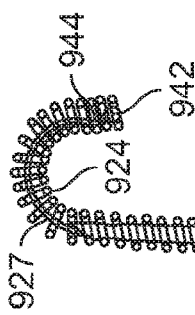
FIGS. 31A-31F are side views of a worktool positioning member, illustrated in a sequence showing the changing curve of a shape memory portion as it moves from a straight configuration (FIG. 31A) to a curved configuration (FIG. 31F)
Figure 31E:
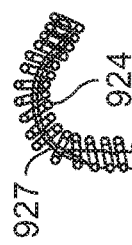
Figure 31D:
Figure 31C:
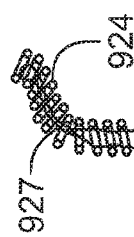
Figure 31B:
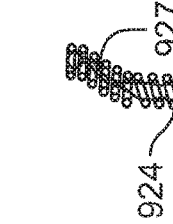
Figure 31A:
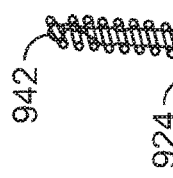
Figure 34D:
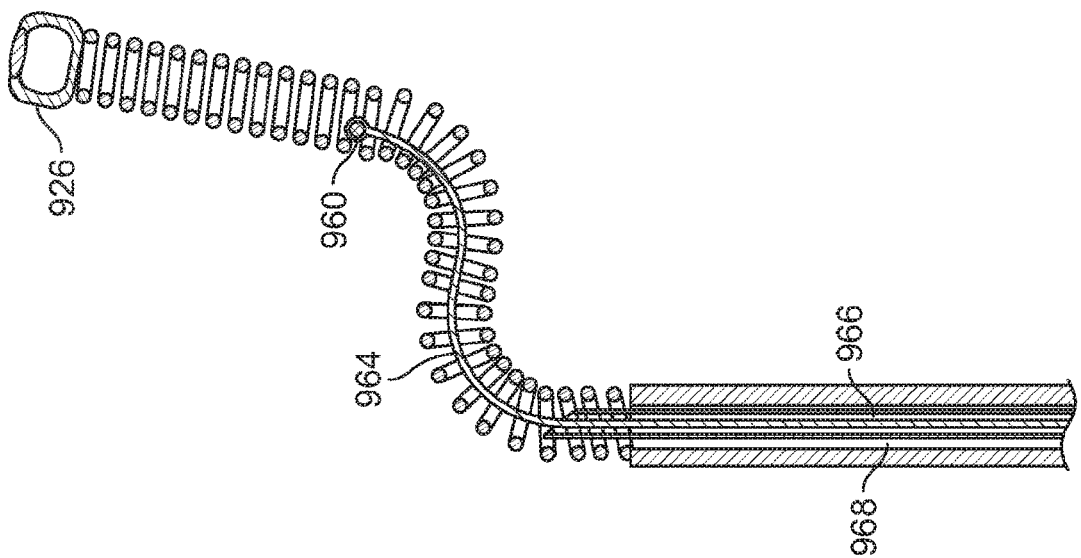
FIG. 34A-34D are partial cross-sectional views of an articulating distal portion of an access device, according to another embodiment.
Figure 34C:
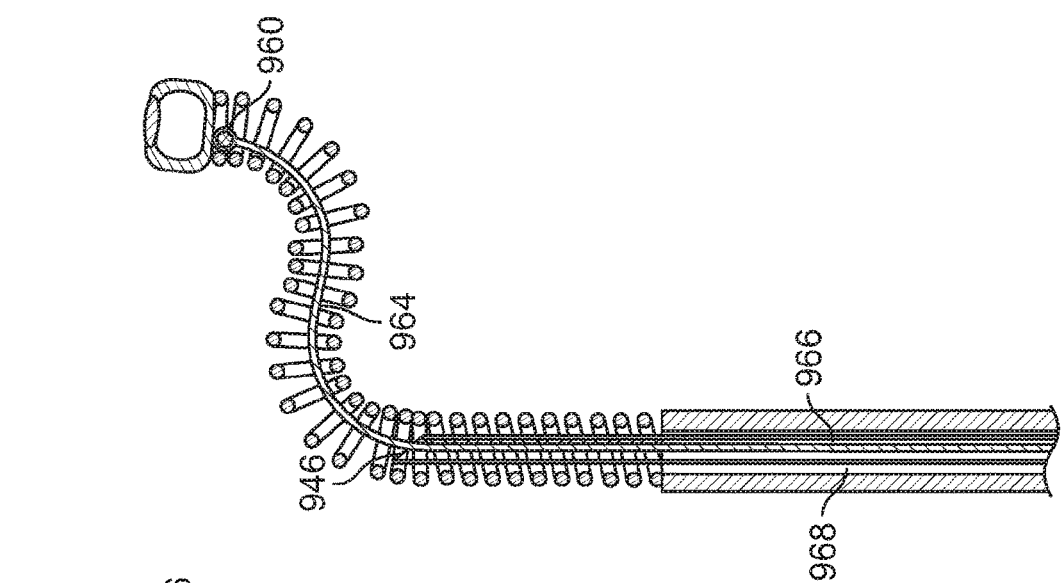
Figure 34B:
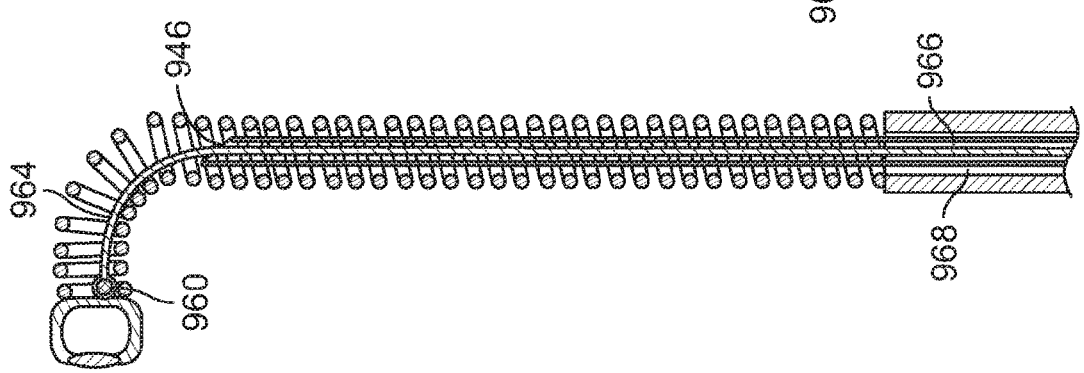
Figure 34A:
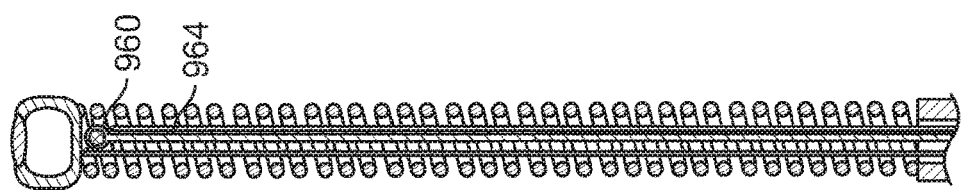

Referring to FIG. 25B, in one embodiment, the access system 970 may include a power cell 956 for providing a power supply and a wireless data transfer for transferring data to and from a working tool 926 (FIG. 26). Thus, such an embodiment of access system 970 may be wire-free. The access system 970 may also include a light source 954 in the proximal portion of sinus access member 908. The light from light source 954 is transmitted to the distal end 926 of the sinus access member 908 via optical fibers 952 routed through a hub 909 and to a distal end of the camera 926 through work channels provided, for example, in the rigid member 920 or wrapped under a layer of ePTFE 905 on the outside of the flexible straight support member 923. Alternatively, a light source, wireless or Bluetooth radio transmitter and power source may all be incorporated in the handle 900. In this case, optical and electrical interfaces would be included in control handle 900, and correspondingly in sinus access member 908.

In some embodiments, the mechanically-steerable tool-positioning mechanism is imbued with a capacity to aim the distally placed tool, such as a camera, in a direction at an angle of at least 90 degrees, preferably greater than 120 degrees, more preferably greater than 140 degrees and even possibly at least 180 degrees, to the general direction of the longitudinal axis and insertion of the worktool, in as many as three degrees of freedom or spatial planes X-Y, Y-Z and X-Z.

Referring to FIGS. 24B-24G, 26, 27 and 28, various views illustrate the linear arrangement of rigid member 920, curved member 927 (including its proximal portion 915) and flexible member 923 (including its distal spring portion 924), relative to one another. In these figures, the distal end is to the left side of the figure, and the proximal end is to the right side. Beginning at the far distal end of sinus access member 908 in FIG. 26, a camera 926 is mounted and attached to a spring portion 924 which, in this tubular or cylindrical exemplary embodiment, is the most flexible portion of flexible member tube 923. In alternative embodiments, the camera 926 may any other suitable work tool, and it is shown here as a camera 926 for illustrative purposes only. Straightener tube 920, over which flexible member tube 923 can slide when actuated, comprises the distal-most portion of rigid, (least flexible, strong) support member 20. Extending into and substantially through straightener tube 920, there can be seen curving member extension rod 915, at least a distal-most portion of which is made of a curving shape memory material. At its proximal coupling end, when the sinus access member 908 is coupled with the handle 900, curved member extension rod 915 is received and centered into a distal receptacle in the inner rod 939.

Referring now to FIGS. 24A-24G and 26-28, what in earlier exemplary embodiments were shown as at least two slidably-coupled elongate support members, are now each attached at their proximal ends to a series of interconnected slidable couplers, at least partially cylindrical concentrically arranged tubes, locking and unlocking mechanisms and sliding actuators. Sinus access member 908 has at its proximal end a largely concentric arrangement of rods, tubes and semi-cylindrical connectors, including C-connector 934, worktool inner connector 933 and D-connector 932, which cooperate as and with B-connector 931, A-connector 929, inner rod 939, centering rod 917, connector engagers, extensor-retractor elements and alignment and stabilizing elements, for ensuring a properly aligned fit with port 919 of handle 900, and for permitting the necessary stable and smooth translation of a user's input on actuators 912 and 914 into the extension or retraction of a tool such as camera 926 located at its distal end.

Referring to FIGS. 24A-28, the curving actuator 912, which slides back and forth on sliding rod 911 when released, is connected via A-connector 929 (FIGS. 24D and 27) to worktool inner connector 933, with which it is coupled. Worktool inner connector 933 is connected at its distal end to curved member extension rod 915, which has connected at its distal end a shape-memory nitinol portion 927.

Extension actuator 914, which initially is advanced simultaneously with curving actuator 912, also slides along sliding rod 911 and is riding on and attached to differential compensation spring 910 (FIGS. 24D-G). Differential compensation spring 910 compensates for slackness caused by nonlinearity in travel of the most distal end of flexible member 924, and camera 926 at its end, as compared with the distal curving nitinol portion 927 at tear-drop ball-end 925 or offset bead 942. Too much slackness or space between ball-end 925 or offset bead 942 and camera 926 can lead to undesirable, uncontrolled motion, potential complications thereof including inability to retract the camera 926 or unintentional puncture by advancing worktool in a slack environment. On the other hand, if the camera 926 is not permitted a small amount of free motion, then it might force through and damage tissue rather than yield. Differential compensation spring 910 works to continuously maintain a balance between desired tension and flexibility, either in advancing or retracting a worktool, between the distal terminal ends 926 and 925, 927 or 942. Differential compensation spring 910 is connected to cylindrical coupler B-connector 931 which is interlocked and pushes/pulls cylindrical coupler C-connector 934 in the sinus access member. C-connector 934 is connected at its distal end to hub 909 which in turn is connected to most flexible least rigid extension tube 923 which is connected at its distal end to coil spring 924 which has camera 926 attached at its most distal end.

Anchoring the sliding members, from proximal to distal, are the sliding rod 911, joined by a frame (not shown) between frame blocks 906 (FIG. 21B) to cylindrical E-connector 935 which is coupled to cylindrical D-connector 932 in sinus access member 908. D-connector 932 is connected at its distal end to straightener tube 920. At the center of the arrangement, seen best in FIGS. 24B-24F and 26, and 27, is the curving member extension rod 915 and at its distal terminus the shape-memory curving support member 904 which is both flexible yet semi-rigid, midway in flexibility and rigidity between most rigid structural support member 922 and least rigid extension tube 923.

The present exemplary embodiments illustrated in FIGS. 20-35 also include features for easily and accurately directing wires, fibers and fluids of various kinds through the access system 970 into the distal end of the worktool itself, or into cavities, sinuses and other areas that are being accessed. Luer 916 provides a connecting structure to which known medication delivery systems may be attached, and fluids may be directed through channel input 907, which leads into hub 909, where the lumen of flexible tube 923 is open to receive the fluid and transmit it to the distal terminus. Hub 909 is a moving chamber, and as its name implies, it is a hub of activity and access for fluids and control wires and fibers. At its proximal end, hub 909 is connected to C-connector 934, hence the linkage to extension actuator 914. At its distal end, hub 909 receives the proximal end of flexible member 923.

Referring now to FIGS. 29-31F and 33A-34D, the distal end of sinus access member 908 shows the nitinol portion 927 extending beyond and out of the straight, rigid tube 920. A bead 942 (or "ball tip" or "rounded distal tip") is sized and angled away from the overall curve of the programmed shape memory curving. The bead 942 is designed to spread any pressure applied against the inner walls of spring 924 and reduce the risk of puncturing or getting stuck on or in between coils, even where curvature spreads the coils slightly. Additionally, a dog-leg 944 (or "curve") is outwardly angled, opposite the general inward curve of the main nitinol portion 927, directly adjacent to the offset bead 942. In this way, as the nitinol portion 927 emerges beyond the overlap at the slash cut end 946, and starts to curve, it does so while always maintaining a shallow attack angle and presenting a broad contact surface against any part of the inner wall of the spring portion 924 with which it makes contact. In this way, the outward force of the nitinol portion 927 is no longer perpendicular to inside wall of spring portion 924, more nearly parallel thereto, and more widely distributed against and easily deflected by the inner wall of the spring portion 924, thus reducing the chance of puncture on extension and/or snagging on retraction.

Referring to FIGS. 30A-30G, the illustrations show curved nitinol portion 927 being retracted back into straightener tube 920. This further makes clear how the dog-leg 944, combined with the angle of bead 942, tends to counter the major curvature of nitinol portion 927.

Referring now to FIGS. 31A-31F, spring portion 924 shows the interaction of the general curvature of nitinol portion 927 and counter curving nitinol terminus dog-leg 944 and bead 942 components. Another feature also demonstrated by the exemplary embodiment, and particularly with reference to FIGS. 30 and 31A-31F, is the use of the offset teardrop-ball end design of bead 942, which is oriented to be biased outwardly, away from the general direction of curvature of curved nitinol 927, to prevent bead 942 from snagging against, or being inserted in between, the coils of spring 924 inner wall surfaces. Finally, most clearly seen in FIG. 34A, the direction at which centered and ball-shaped bead 960 projects from the nitinol terminus 964 is such that when fully retracted it is largely seated into the V-shaped recess formed by slash-cut 946 at the distal open end of rigid support member 920; the partially exposed top portion of the bead 960 being effective to prevent any interstices between the coils of spring 924 from snagging on the distal most extreme tip of rigid straight supporter as the worktool is retracted back into the starting fully retracted position.

Referring to FIGS. 30A-30F and 32A-32C, it was noted earlier herein that providing the nitinol shape-memory portion 927 with a non-rounded cross-sectional profile permits adaptations for ease of control to prevent unwanted rotation, twisting or torqueing of the shape-memory support member. A further structural configuration to further reduce any possibility of longitudinal rolling of the nitinol shape memory portion 927 comprises providing it with a non-rounded profile and providing rigid straightener tube 920 with at least one narrowing, stricture or crimp 948 immediately adjacent to slash cut end 946. Examples of non-round cross-sectional profile shapes for ensuring the correct orientation of the nitinol shape memory portion 927 include: ellipses, polygons, semi-cylindrical, oblong and many others. FIG. 33A further illustrates an embodiment wherein the sinus access member is inserted into an outer flexible sheath 954, optionally having an open or perforated distal end (not shown) which can remain in place after sinus access member 908 is retracted and withdrawn from a body cavity. Sheath 954 can remain in place and function like a catheter, a drain, an irrigation tube for flushing or draining or introducing contrast media for imaging, or to reintroduce a different sinus access member into the same location for further procedures.

Referring now to FIGS. 32A-32C, one embodiment includes an ePTFE film 905 wrapped about spring portion 924 and flexible member 923. In one embodiment, the orientation of the wrap of the ePTFE film 905 may be perpendicular to the longitudinal axis of tube 923, providing a smooth surface to the stainless steel chassis, as well as desirable structural reinforcement and fluid containment, to help prevent accidental puncture of tube 923 or snagging of the nitinol shape memory member in deformations, collapse, non-longitudinal expansion or separation of the coils of spring 924.

With reference to FIGS. 32A-32C, windings of ePTFE film 905 may be applied in several thickness patterns, for example with a conical profile, or capsular or any other desired contour, and that adds any desired thickness, for example from 0 mm to 2 mm of radius, or total cross-sectional diameter increasing from an unwrapped 2 mm to a wrapped 6 mm or more. Wires 928 and/or optic fibers can be routed to a camera 926, such as a camera, by being run along the outside inner curvature (or "intrados") of flexible support members 923 and 924, and the wires 928 may be held in place under the ePTFE 905 windings. Alternatively, bundles or sheath protected optic fibers can be routed outside or inside rigid straight support member 920 alongside nitinol extension rod 915. Another preferable exemplary embodiment provides a work channel formed in nitinol extension rod 915 or in the outer surface of support member 920 through which fibers and fluids may be routed.

Figure 35:
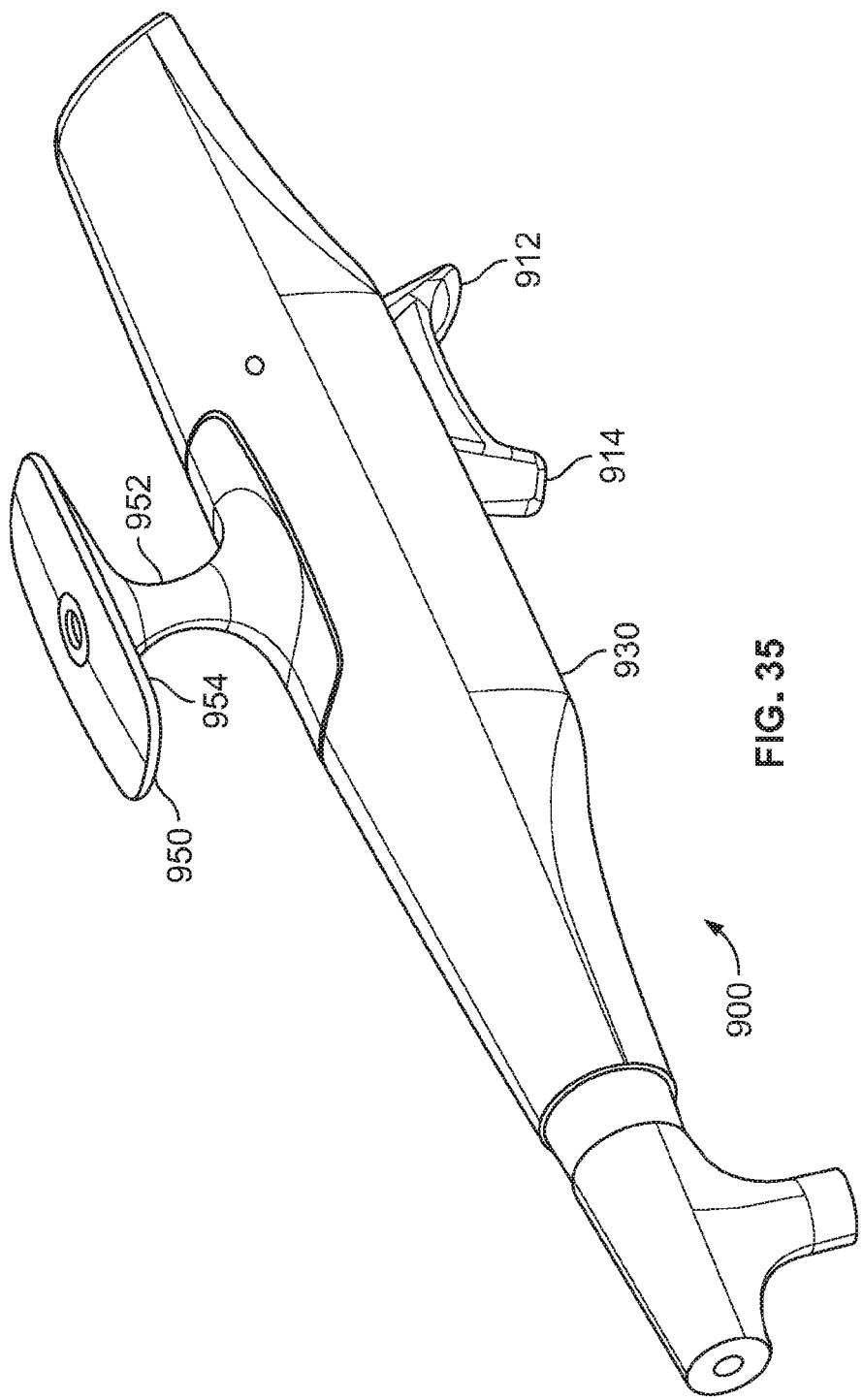
FIG. 35 is a perspective view of control handle having an ergonomic outer housing, according to one embodiment.

With reference to FIG. 35, an alternative embodiment of a handle 900 may include T-shaped knuckle-guard-like finger grip 950 extending outwardly from the housing on the side opposite the actuators 912 and 914. In practice, a user may grasp the handgrip housing 930, palm down, such that the thumb is in position to slide the actuators 912 and 914, and with the stalk 952 of finger grip 950 between two fingers and the underside of the T-top crossbar 954 against or adjacent the back of the fingers. Thus, the handle 900 can be permitted to "hang" from the fingers while manipulated one-handed by the user. Alternatively, a user can hold the handle in a pencil-like grip.

The embodiments described herein provide a paranasal sinus access system having a reusable handle proximally and a disposable sinus access member distally. According to the teachings herein, a significant portion (e.g., the entire sinus access member) of the access system can now be made economically as a disposable piece. The teachings herein have rendered the sinus access member to be a disposable alternative, to be disposed of after each use, and yet just as, if not more so, utilitarian and reliable as was previously known.

In accordance with another embodiment, the access system (i.e., including the rigid, curved and flexible members) may be accommodated within a housing (not shown) so that its components would be concealed from the patient. The housing includes a distal port through which the access system exits the housing and can be inserted into the body of the patient. The operator places the housing such that the distal port thereof is located adjacent to the nostril of the patient, and the access system can be pushed via the nostril into the sinus cavity of the patient. When the procedure is done, the operator retracts the access system into the concealing housing, and only then the operator removes the housing from the patient. In this manner, an awake patient can only see the concealing housing, thus potentially reducing patient anxiety.

In accordance with a further embodiment, and as mentioned above, a camera is coupled with the access system. The camera can be coupled at the distal end of the access system (e.g., coupled to the functional distal head of the access system—e.g., functional head 304 of FIG. 5). In this manner, the operator can view the route ahead of the access system during the procedure. The camera dimensions can be, for example, about 1.5 (length×1×1 mm. Alternatively, the camera can be coupled proximally (e.g., a few millimeters) of the distal end of the access system. The access system can include more than a single camera for covering a wider field of view (e.g., imaging opposite directions), or for stereoscopic imaging. The camera is coupled to a plurality of wires (e.g., electrical wires) configured to transfer signals from the camera to other electrical components, located proximally to the camera and possibly outside of the patient (e.g., a processor and a sampler).

The access system can further include illumination means (i.e., illumination devices) for illuminating the surrounding of the access system for the camera. The illumination devices can be, for example, optical fibers coupled to an external light source. The flexibility of the optical fiber enables it to conform to the bent path of the access system. According to some embodiments, the illuminating devices can further include lenses, prisms, reflectors, deflectors, optical couplers, and other optical components that can transmit light from an external light source through the access system.

For example, the access system can include a distal camera and two fiber bundles position on either side. The camera wiring and the illumination bundles are passing via the work channel of the access system (i.e., or via separate work channels). The optical fibers can be made of plastic (e.g., PMMA). The diameter of the optical fibers may be in the range of about 150 μm-500 μm, and preferably of about 250 μm.

The optical fibers and the camera wires are arranged so that they are not harmed (e.g., stretched, torn, broken) during the insertion and flexion of the access system. The optical fibers and the camera wires are preferably located at the side of the access system that is close to the bend in the access system for shortening their path, and avoiding unnecessary stretch. That is, the optical fibers and the camera wires are passed along the shortest peripheral curvature (i.e., internal curvature) of the access system. Coupling the camera wires along this internal curvature may provide further mechanical strengthening to the supporters' structure. For example, the un-stretchable camera wires limit the bending of the access system. In other words, the optical fibers and the camera wires are preferably positioned at, or toward, the intrados of the bend of the access system.

Alternatively, the optical fibers can be positioned toward the extrados of the curved path of the access system. In this manner, the radius of curvature of the optical fibers is enlarged for the same curved path of the access system. Thereby, the amount of light that escapes the optical fibers at the curve is decreased. In other words, the flexion of the optical fibers is reduced for reducing the amount of escaping light. For allowing the optical fibers to be positioned toward the extrados, without stretching the fibers, the fibers may be loose when the curved member is overlapped with the rigid member and is straightened thereby.

In accordance with yet another embodiment, the camera (i.e., or cameras or other optical sensors) can be coupled to one or more image processors for handling the acquired image signals. For example, the image processor can compensate for the maneuvers of the access system (i.e., and therefore of the camera) by rotating the image, inverting the image, transposing the image, and the like. For instance, when the operator pushes the curved member beyond the rigid member such that the access system bends at an angle of 120 degrees, and the camera is therefore partially inverted, the image processor can perform image inversion for compensating for the camera inversion.

According to some embodiments, the handling of the acquired image signals may be carried out automatically or semi-automatically (i.e., the operator is partially involved in operation), for example, based on additional signals generated by one or more sensors (e.g., an accelerometer or a position sensor located in the access system). Alternatively, the image handling may be controllable by the operator (i.e., manual handling). The handling of the image may further include controlling the illumination devices (e.g., controlling the amount of light). Controlling any of the camera, image signals and illumination may be carried out (at least partially) via a user interface (e.g., button, switch, knob, touch-sensitive screen) located in a housing (e.g., handle) of the access system.

In accordance with yet a further embodiment, additional devices can be externally coupled to the access system and thereby be guided toward, or into, the sinus cavity (i.e., add-on devices). The add-on devices can be coupled, for example, distally to (or at the vicinity of) the distal head of the access system. The add-on device can be coupled, for example, by employing a grip. The add-on devices can be, for example, a swab for collecting tissues, a needle for injecting a fluid (e.g., therapeutic fluid or a drug), a pincer-like head for inserting or removing pads or bandages into the patient's body, and the like. The add-on devices can be employed for performing actions on the way to the sinus cavity, such as local anesthetic injection, or placement or removal of bandages.

In the examples set forth herein above, various access systems were presented. The access systems are directed at accessing the nasal cavity and paranasal sinuses of a patient. Additionally, the access systems can be employed for inserting a working tool via the access system.

In the exemplary embodiments, steering, or aiming, is accomplished by using the general method described earlier of overlapping members having different rigidities and with at least one member having a shaped memory that permits controlled formation of a desired angle, or shape. In the exemplary embodiments, determination of where the angle will form is largely dependent on where the shaped memory curving support member extends beyond the more rigid support member to which it is slidably coupled. Where the curving portion of the shaped-memory curving support member no longer overlaps the more rigid support member, it starts to resume its memorized curved shape. Once the desired angle has been attained, and optionally a lock has been engaged to maintain that position, the flexible member can be slidably extended beyond the distal curved portion to bring the worktool into the desired position.

One or more structural modifications may be made to some of the embodiments described here, to enhance safety, ease of use and/or utility and/or to reduce cost of manufacture and operation of the access system. For example, in one embodiment, the end of the shape-memory curving support member may be given an off-set teardrop or centered ball shape, which may enhance the extension/retraction of the shape-memory curving support member as well as the least rigid straight support member which carries the worktool at its distal end, that will prevent the end of the shape memory curving support from locking up against, or poking through protective coverings, if any, of the least rigid straight support member as they move against one another, whether in extension or retraction. Some embodiments may include external wrapping of oriented ePTFE film (commonly referred to as "plumber's tape") about the outermost support member, which may serve to reinforce the cross-sectional integrity of that portion of the least rigid straight support member which must slide over and past the extended angled section of the shape-memory curving member, without compromising the required flexibility. In some embodiments, sufficient wrappings of ePTFE may be used to change the effective cross-sectional diameter, thereby imparting, for example, a conical, frustoconical or capsular outer shape which can dilate the passages it is pushed through while not compromising flexibility. Some embodiments may include shaping the distal end of the tubular rigid support member with a slash cut to nestingly receive the teardrop- or ball-shaped distal end of curving support member such that it is only minimally and glancingly contacted in any substantial manner by any part of flexible member, thereby also preventing it from being retracted too far back into the rigid straight support member and its partial nesting of the ball-end decreasing any possibility of the rigid support member from snagging coils of a spring-shaped section of most the flexible support member. Having a slant cut at the end of the rigid straight support also provides for a smooth, no-step, transition when the spring portion of the flexible member is retracted back over the still-extended curving support member and rigid support member; when the curving support member is extended, its inner curvature is pulled into tight contact with the tip of the slant cut and the spring cannot get stuck there; however, when retracting the spring, it tends to move closer to the outer curvature of the curved nitinol (see FIG. 29) and would get stuck as it transits from the outer radius of the curved nitinol section 927 to the distal end of the most rigid support member 946, had it been left rectangular and not been slanted (i.e. had it been a step). Providing the handle 900 with an outer ergonomic shape and arrangement of controls may facilitate single-handed operation by a skilled operator.

In the above description, the access system was employed for accessing the nasal and sinus cavities of a patient. As mentioned previously, alternative embodiments may be employed for accessing other cavities within the body of a patient, or other cavities in other environments, which can only be accessed via a curved tortuous path. For example, other areas of the ear, nose and throat, abdominal cavities, thoracic cavities, reproductive system, urinary system, gastric system, brain tissue, and the like.

It will be appreciated by persons skilled in the art that the invention is not limited to what has been particularly shown and described hereinabove. Rather the scope of the invention is defined only by the claims, which follow.

We claim:

1. An endoscope device for accessing and visualizing a paranasal sinus cavity of a patient, the endoscope device comprising:
    a shaft, comprising:
        a middle rigid support tube;
        an inner curved shape memory member slidably disposed at least partially within the middle rigid support tube, wherein a distal portion of the inner curved shape memory member assumes a default curved shape when advanced out of a distal end of the middle rigid support tube, and wherein the distal portion of the inner curved shape memory member in the default curved shape comprises:
            a proximal inward curve facing in a first direction;
            a distal outward curve facing in a second direction opposite the first direction; and
            a bead at a distal end of the distal portion; and
        an outer flexible tube slidably disposed over the middle rigid support tube and the inner curved shape memory member, wherein a distal portion of the outer flexible tube assumes the default curved shape of the distal portion of the inner curved shape memory member when the outer flexible tube resides over the distal portion of the inner curved shape memory member and assumes a default straight shape when advanced beyond the distal portion of the inner curved shape memory member;
    a handle coupled with a proximal end of the shaft, the handle comprising:
        a housing;
        at least one slider movably coupled with the housing for advancing and retracting the inner curved shape memory member and the outer flexible tube relative to the middle rigid support tube; and
    a camera attached to the distal portion of the outer flexible tube.

2. The endoscope device of claim 1, wherein the at least one slider comprises:
    a curving slider movably coupled with the housing and with a proximal end of the inner curved shape memory member for advancing and retracting the inner curved shape memory member through the distal end of the middle rigid support tube; and
    an extension slider movably coupled with the housing and with a proximal end of the outer flexible tube for extending and retracting the outer flexible tube over the inner curved shape memory member and the middle rigid support tube,
    wherein the curving slider and the extension slider are releasably coupled together, and
    wherein the curving slider, when disconnected from the extension slider, is locked in position relative to the handle while the extension slider is free to slide back and forth.

3. The endoscope device of claim 2, wherein the curving slider and the extension slider are releasably coupled together via a spring clutch.

4. The endoscope device of claim 1, wherein the handle further comprises an electronics port for providing at least one of power or data transfer to the handle.

5. The endoscope device of claim 1, wherein the shaft is removable from the handle.

6. The endoscope device of claim 1, wherein the handle further comprises at least one additional feature selected from the group consisting of a battery housing, a wireless data transmitter, a fluid delivery port and a light source.

7. The endoscope device of claim 1, wherein the shaft is configured to rotate relative to the handle about a longitudinal axis drawn through the shaft and the handle.

8. The endoscope device of claim 1, wherein at least the distal portion of the inner curved shape memory member has a non-round cross-sectional shape that causes the distal portion to curve in only one plane.

9. The endoscope device of claim 1, wherein the shaft further comprises a working tool channel configured for passage of a working tool or irrigation fluid therethrough.

10. The endoscope device of claim 9, wherein the working tool is selected from the group consisting of cameras, optical fibers, textile threads, metal threads, light sources, swabs, tweezers, sample collection containers, sample collection devices, suction tubes, irrigation tubes, injection tubes, balloons, dilation tools, ultrasound probes, ultrasound waveguides, infrared imaging devices, probes, sensors, stylets, and guide wires.

11. The endoscope device of claim 9, wherein the working tool channel comprises a lumen in the outer flexible tube.

12. The endoscope device of claim 1, wherein a radius of curvature of proximal inward curve of the distal portion of the inner curved shape memory member in the default curved shape is between 2 millimeters and 5 millimeters.

13. The system of claim 1, wherein the outer flexible tube comprises a shape memory material.

14. The endoscope device of claim 1, wherein the outer flexible tube comprises a spring wrapped in polytetrafluoroethylene (PTFE) perpendicularly to a longitudinal axis of the outer flexible tube.

15. The endoscope device of claim 1, further comprising a distal head coupled with a distal end of the outer flexible tube, wherein the distal head comprises the camera and at least one light source.

16. The endoscope device of claim 15, wherein the at least one light source comprises at least one light-emitting diode (LED).

17. The endoscope device of claim 16, wherein the at least one light source comprises at least one illuminating fiber coupled with the distal head and extending proximally along an inner curvature of the outer flexible tube.

18. The endoscope device of claim 1, wherein the bead comprises an offset bead facing in the second direction, wherein the distal outward curve is adjacent the offset bead.

19. The endoscope device of claim 1, wherein the distal end of the middle rigid support tube comprises a beveled end, and wherein an opening of the middle rigid support tube at the beveled end faces outward, away from the proximal inward curve of the distal portion of the inner curved shape memory member.

20. The endoscope device of claim 1, further comprising a control unit removably coupled with the handle for providing at least one of power or data signals to the device.

* * * * *